United States Patent
Neville et al.

(10) Patent No.: US 11,697,669 B2
(45) Date of Patent: Jul. 11, 2023

(54) HEMI-CITRATE SALTS OF GABA-A POSITIVE ALLOSTERIC MODULATOR AND CRYSTALLINE FORM THEREOF

(71) Applicant: Praxis Precision Medicines, Inc., Boston, MA (US)

(72) Inventors: Doris Neville, Boston, MA (US); Ahmad Hashash, Boston, MA (US); Karl Hansen, Boston, MA (US); Johann Chan, Boston, MA (US)

(73) Assignee: PRAXIS PRECISION MEDICINES, INC., Boston, MA (US)

( * ) Notice: Subject to any disclaimer, the term of this patent is extended or adjusted under 35 U.S.C. 154(b) by 0 days.

(21) Appl. No.: 17/824,205

(22) Filed: May 25, 2022

(65) Prior Publication Data

US 2022/0289789 A1    Sep. 15, 2022

Related U.S. Application Data

(63) Continuation of application No. PCT/US2022/016612, filed on Feb. 16, 2022.

(60) Provisional application No. 63/150,782, filed on Feb. 18, 2021.

(51) Int. Cl.
  *C07J 43/00* (2006.01)
  *A61K 9/20* (2006.01)
  *A61K 45/06* (2006.01)

(52) U.S. Cl.
  CPC .......... *C07J 43/003* (2013.01); *A61K 9/2013* (2013.01); *A61K 9/2095* (2013.01); *C07B 2200/13* (2013.01)

(58) Field of Classification Search
  CPC .... C07J 43/003; A61K 9/2013; A61K 9/2095; A61K 45/06; A61K 9/20; A61K 9/2027; A61K 9/2018; A61K 9/2054; C07B 2200/13
  See application file for complete search history.

(56) References Cited

U.S. PATENT DOCUMENTS

| | | |
|---|---|---|
| 10,562,930 B1 * | 2/2020 | Olivier .................... A61K 9/20 |
| 2006/0074059 A1 | 4/2006 | Goliber et al. |
| 2009/0131383 A1 | 5/2009 | Woodward |
| 2020/0071350 A1 | 3/2020 | Olivier et al. |

FOREIGN PATENT DOCUMENTS

WO    2004072079 A1    8/2004

OTHER PUBLICATIONS

Rodriquez, Kari (Authorized Officer), International Search Report and Written Opinion issued in International Patent Application No. PCT/US2022/016612 dated May 4, 2022, (8 pages).

* cited by examiner

*Primary Examiner* — John M Mauro
(74) *Attorney, Agent, or Firm* — MH2 Technology Law Group, LLP

(57) ABSTRACT

Disclosed herein are hemi-citrate salts of Compound 1, crystalline forms thereof, methods of their preparation, pharmaceutical compositions thereof, and methods of their use.

28 Claims, 21 Drawing Sheets

HEMI-CITRATE SALTS OF GABA-A POSITIVE ALLOSTERIC MODULATOR AND CRYSTALLINE FORM THEREOF

CROSS-REFERENCE TO RELATED APPLICATIONS

This application is a continuation application of International Application No. PCT/US2022/016612, filed on 16 Feb. 2022, which claims priority to U.S. Provisional Patent Application No. 63/150,782, filed Feb. 18, 2021, which is incorporated herein by reference in its entirety.

TECHNICAL FIELD

The present disclosure relates to hemi-citrate salts of 3α-hydroxy-3β-methoxymethyl-21-(1'-imidazolyl)-5α-pregnan-20-one, crystalline forms thereof, and processes for preparing such salts and crystalline forms, as well as pharmaceutical compositions thereof and methods of their use.

BACKGROUND

3α-Hydroxy-3β-methoxymethyl-21-(1'-imidazolyl)-5α-pregnan-20-one (Compound 1) is a synthetic neuroactive steroid. Its primary molecular target is the γ-aminobutyric acid type A (GABA-A) receptor, where it acts as a positive allosteric modulator (PAM) of channel function. The structural formula of Compound 1 appears below.

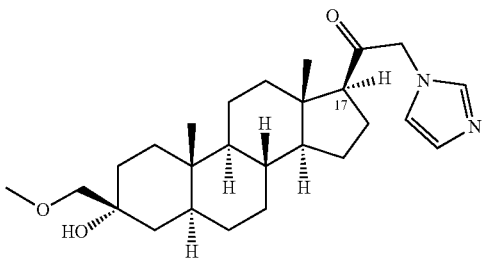

Neuroactive steroid GABA-A PAMs have demonstrated clinical efficacy in epilepsy, post-partum depression, and major depression.

The synthesis of Compound 1 is described in U.S. Application Publication Nos. 2004/0034002 and 2009/0118248; a crystalline form of Compound 1 free base is described in U.S. Application Publication No. 2006/0074059; pharmaceutical compositions containing Compound 1 are described in U.S. Application Publication No. 2009/0131383; and crystalline polymorphs of salts of Compound 1 are described in U.S. Application Publication No. 2020/0071350, all of which are hereby incorporated by reference in their entirety for all purposes.

Compound 1 is poorly soluble at the pH found in the lower GI tract, which may limit the oral bioavailability of Compound 1. To achieve improved solubility, various salt forms of Compound 1 and polymorphic forms of these salts were developed and tested, as described in, for example, U.S. Application Publication No. 2020/0071350. As disclosed in U.S. Application Publication No. 2020/0071350, mono-citrate salts of Compound 1 were determined to have favorable overall properties, including improved stability, improved crystalline properties, and improved dissolution. The mono-citrate salt of Compound 1 has a molar ratio of 3α-Hydroxy-3β-methoxymethyl-21-(1'-imidazolyl)-5α-pregnan-20-one to citrate of 1:1.

Nonetheless, formulation of mono-citrate salts of Compound 1 proved to be challenging, particularly as tablets ("mono-citrate tablets") for oral administration. For successful therapeutic utility, it is important that the physiochemical properties of an active compound are known or can be reasonably predicted throughout the manufacturing and pharmaceutical processing procedures as well as during storage, shipping, and its eventual therapeutic use. While some therapeutic compounds can exhibit desirable therapeutic properties, it is not always possible to translate these therapeutic properties into a suitable pharmaceutical composition because the therapeutic compound may have undesirable physiochemical properties, such as poor chemical or processing properties.

Accordingly, there is a need for improved formulations of Compound 1 salts and processes for making the same, wherein the Compound 1 salts have both desirable therapeutic utility and physiochemical properties.

SUMMARY

The present disclosure provides a hemi-citrate salt of Compound 1, crystalline forms thereof, and methods of making and using such a salt and crystalline forms. The disclosure also provides pharmaceutical compositions comprising a hemi-citrate salt of Compound 1.

In accordance with the disclosure, it has now been discovered that hemi-citrate salt forms of Compound 1 show surprisingly improved characteristics relative to other salt forms, including the mono-citrate salts described in U.S. Application Publication No. 2020/0071350. Such improved properties include, but are not limited to, enhanced chemical and physical stability, longer storage shelf-life, improved processing properties, and improved dissolution profiles. Additionally, as set forth herein, Compound 1 hemi-citrate salts are more amenable for developing oral formulations, particularly in the form of tablets, than other salt forms, including the mono-citrate salts.

In one aspect, the present disclosure provides a substantially pure hemi-citrate salt of Compound 1, wherein the molar ratio of 3α-Hydroxy-3β-methoxymethyl-21-(1'-imidazolyl)-5α-pregnan-20-one to citrate is about 2:1. In some embodiments, the present disclosure provides a substantially pure hemi-citrate salt of Compound 1 having the formula:

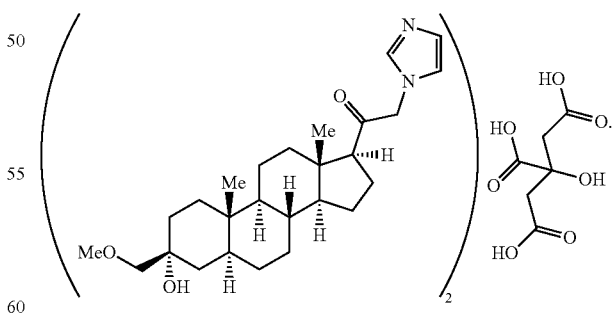

In some embodiments, the hemi-citrate salt of Compound 1 disclosed herein is substantially free of a mono-citrate salt of Compound 1. In some embodiments, the hemi-citrate salt of Compound 1 disclosed herein contains less than about 5% by weight of a mono-citrate salt of Compound 1. In some embodiments, the hemi-citrate salt of Compound 1 disclosed herein is a hydrate. In some embodiments, the hemi-citrate salt of Compound 1 disclosed herein is a channel hydrate. In some embodiments, the hemi-citrate salt of Compound 1 disclosed herein has a water content from about 0% to about 5% by weight.

In some embodiments, the hemi-citrate salt of Compound 1 disclosed herein is a monohydrate. In other embodiments, the hemi-citrate salt of Compound 1 disclosed herein includes less than one molecule of water for every molecule of Compound 1. In some embodiments, the hemi-citrate salt of Compound 1 disclosed herein is a dehydrated hydrate. In other embodiments, the hemi-citrate salt of Compound 1 disclosed herein is anhydrous. In some embodiments, the hemi-citrate salt of Compound 1 disclosed herein is a sesquihydrate.

In some embodiments, the present disclosure provides a crystalline form of the hemi-citrate salt of Compound 1. In some embodiments, the crystalline form of the hemi-citrate salt of Compound 1 is crystalline Form I, as disclosed herein. In some embodiments, the crystalline Form I has a water content of about 4.4% by weight, and in some embodiments, the crystalline Form I exhibits a differential scanning calorimetry (DSC) thermogram having a first peak value at about 65.2±2.0° C. and a second peak value at about 126.3±2.0° C. In some embodiments, the crystalline Form I exhibits a thermogravimetric analysis (TGA) thermogram with a weight loss of about 0.0% to 4.4% in the temperature range of 25 and 125° C.

In some embodiments, the crystalline Form I of the hemi-citrate salt of Compound 1 is a channel hydrate Form IA. In some embodiments, the crystalline Form IA exhibits an X-ray powder diffraction (XRPD) pattern comprising at least one of the following peaks at the diffraction angle 2-theta: 5.3±0.2, 10.6±0.2, 14.5±0.2, 15.9±0.2, 17.2±0.2, 17.6±0.2, 21.0±0.2, and 25.5±0.2, and in some embodiments, the crystalline Form IA exhibits an X-ray powder diffraction (XRPD) pattern comprising at least three of the following peaks at the diffraction angle 2-theta: 5.3±0.2, 10.6±0.2, 14.5±0.2, 15.9±0.2, 17.2±0.2, 17.6±0.2 20.5±0.2, 21.0±0.2, and 25.5±0.2. In some embodiments, the crystalline Form IA exhibits an X-ray powder diffraction (XRPD) pattern comprising the following peaks at the diffraction angle 2-theta: 5.3±0.2, 14.5±0.2, and 25.5±0.2. In some embodiments, the crystalline Form I exhibits an X-ray powder diffraction (XRPD) pattern that is substantially similar to FIG. 1 (Form IA).

In some embodiments, the crystalline Form I of the hemi-citrate salt of Compound 1 is a channel hydrate Form IB. In some embodiments, the crystalline Form I exhibits an XRPD pattern that is substantially similar to FIG. 2 (Form IB). In some embodiments, the crystalline Form IB exhibits an XRPD pattern comprising at least one of the following peaks at the diffraction angle 2-theta: 5.4±0.2, 10.9±0.2, 14.5±0.2, 16.3±0.2, 17.1±0.2, 17.5±0.2, 21.0±0.2, and 25.5±0.2, and in some embodiments, the crystalline Form IB exhibits an X-ray powder diffraction (XRPD) pattern comprising at least three of the following peaks at the diffraction angle 2-theta: 5.4±0.2, 10.9±0.2, 14.5±0.2, 16.3±0.2, 17.1±0.2, 17.5±0.2, 20.3±0.2, 21.0±0.2, and 25.5±0.2. In some embodiments, the crystalline Form IB exhibits an X-ray powder diffraction (XRPD) pattern comprising the following peaks at the diffraction angle 2-theta: 5.4±0.2, 14.5±0.2, and 25.5±0.2. It has been discovered that Form IB is surprisingly stable and does not readily revert to forms with increased hydration (e.g., Form IA), even under conditions of high humidity.

In certain embodiments disclosed herein, the hemi-citrate salt of Compound 1 is defined by unit cell parameters substantially similar to the following: a=34.7 Å, b=8.3 Å, c=31.7 Å, α=90°, β=108.5°, γ=90°, Space group C2, and Molecules/asymmetric unit 2, wherein the crystalline form is at about 173 K.

In certain aspects, disclosed herein are pharmaceutical compositions comprising crystalline Form I of the hemi-citrate salt of Compound 1, wherein the weight ratio of crystalline Form IB to crystalline Form IA is greater than about 5:1, greater than about 10:1, greater than about 20:1, greater than about 50:1, or greater than about 100:1. In certain embodiments, the pharmaceutical compositions of the disclosure comprise channel hydrate Form IB of the hemi-citrate salt of Compound 1 and is substantially free of channel hydrate Form IA of the hemi-citrate salt of Compound 1.

The present disclosure further provides a pharmaceutical composition comprising a hemi-citrate salt of Compound 1 having the formula:

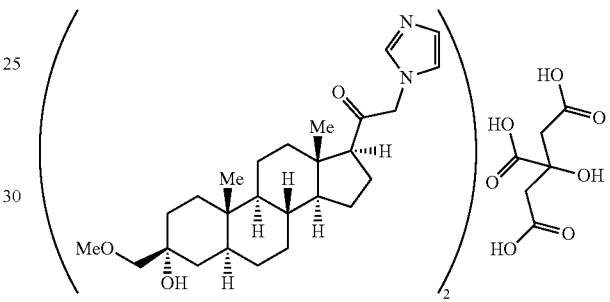

and a pharmaceutically acceptable excipient, wherein the composition is substantially free of a mono-citrate salt of Compound 1. In particular embodiments, the pharmaceutical composition is an oral dosage form, such as a tablet. In some embodiments, the pharmaceutical composition comprises channel hydrate Form IA of the hemi-citrate salt of Compound 1. In other embodiments, the pharmaceutical composition comprises channel hydrate Form IB of the hemi-citrate salt of Compound 1. In other embodiments, the pharmaceutical composition comprises a mixture of channel hydrates Form IA and Form IB of the hemi-citrate salt of Compound 1. In certain embodiments, after the pharmaceutical composition is stored at about 40° C. and 75% relative humidity for about 6 months, the chemical purity of the hemi-citrate salt of Compound 1 in the composition is at least about 98%, and in certain embodiments, the pharmaceutical composition comprises no more than about 0.5% by weight of a C-17 epimer of Compound 1 after the composition is stored at about 40° C. and 75% relative humidity for about 6 months, based on the total weight of Compound 1 in the composition.

In some embodiments, the disclosure provides pharmaceutical compositions comprising a hemi-citrate salt of Compound 1 and a lubricant, such as magnesium stearate, wherein the percentage of the lubricant in the pharmaceutical composition is less than about 4% by weight, such as less than about 3%, less than about 2.5%, or less than about 2% by weight. In some embodiments, the pharmaceutical compositions comprise from about 0.5% to about 3%, such as from about 1% to about 2%, of a lubricant, such as magnesium stearate, by weight (e.g., about 0.5%, about 1%, about 1.5%, about 2%, about 2.5%, or about 3% magnesium stearate by weight). In some embodiments, the pharmaceutical composition further comprises crospovidone, and in certain embodiments, the percentage of crospovidone in the pharmaceutical composition is from about 3% to about 8% by weight. In certain embodiments, the pharmaceutical composition comprises about 25% hemi-citrate salt of Compound 1 by weight, about 2% magnesium stearate by weight, and about 7% crospovidone by weight.

In some embodiments, the disclosure provides a pharmaceutical composition comprising a hemi-citrate salt of Compound 1 that does not gel or precipitate upon contacting an acidic solution. Without being bound by theory, it is believed that the stability of hemi-citrate salts of Compound 1 in acidic media minimizes unintended gelling of Compound 1, which gelling could result in a reduction of bioavailability.

In some embodiments, the disclosure provides pharmaceutical compositions that comprise about 20% to about 30% (e.g., about 20%, about 22%, about 25%, about 27%, about 28%, about 29% or about 30%) by weight of a hemi-citrate salt of Compound 1 and from about 1% to about 3%, from about 1.5% to about 2.5%, or from about 1.75% to about 2.25% magnesium stearate by weight. In some embodiments, the Compound 1 hemi-citrate salt in the pharmaceutical composition is a channel hydrate Form IA. In other embodiments, the Compound 1 hemi-citrate salt in the pharmaceutical composition is a channel hydrate Form IB. In some embodiments, the Compound 1 hemi-citrate salt in the pharmaceutical composition is a mixture of channel hydrate Form IA and channel hydrate Form IB. In certain embodiments, the pharmaceutical composition contains less than 5% of a mono-citrate salt of Compound 1 by weight.

In some embodiments, the pharmaceutical composition disclosed herein is formulated for oral delivery, and in some embodiments, the pharmaceutical composition is a tablet. In some embodiments, the disclosure provides tablets comprising a hemi-citrate salt of Compound 1 and magnesium stearate, wherein the tensile strength of the tablets is at least about 1.7 megapascals (MPa). In some embodiments, the tablets have a tensile strength from about 1.7 MPa to about 4.5 MPa. In some embodiments, the tablets have a tensile strength from about 1.7 MPa to about 3.5 MPa. In some embodiments, the tablet has a disintegration time of less than about 2.5 minutes.

In another aspect, the present disclosure provides a method of preparing a hemi-citrate salt of Compound 1. In some embodiments, the method comprises: (a) dissolving a mono-citrate salt of Compound 1 in a $C_1$-$C_2$ alcohol to produce a solution; and (b) adding the solution to water to provide the hemi-citrate salt of Compound 1. In some embodiments, the method comprises: (a) suspending a mono-citrate salt of Compound 1 in water; and (b) isolating the hemi-citrate salt of Compound 1. In some embodiments, the method further comprises isolating and drying the hemi-citrate salt of Compound 1. Also disclosed herein is a hemi-citrate salt of Compound 1 prepared according to the methods disclosed herein.

In yet another aspect, the present disclosure provides methods of administering a hemi-citrate salt of Compound 1. In some embodiments, the hemi-citrate salt of Compound 1 is orally administered. The present disclosure also provides methods of treating a disease, disorder, or condition comprising administering to a patient in need thereof a therapeutically effective amount of a hemi-citrate salt of Compound 1. In certain embodiments, the disease, disorder, or condition is selected from epilepsy, post-partum depression, major depressive disorder, bipolar disorder, treatment resistant depression, and anxiety.

BRIEF DESCRIPTION OF THE DRAWINGS

The present application can be understood by reference to the following description taken in conjunction with the accompanying drawings.

DETAILED DESCRIPTION

I. Definitions

Figure 1:
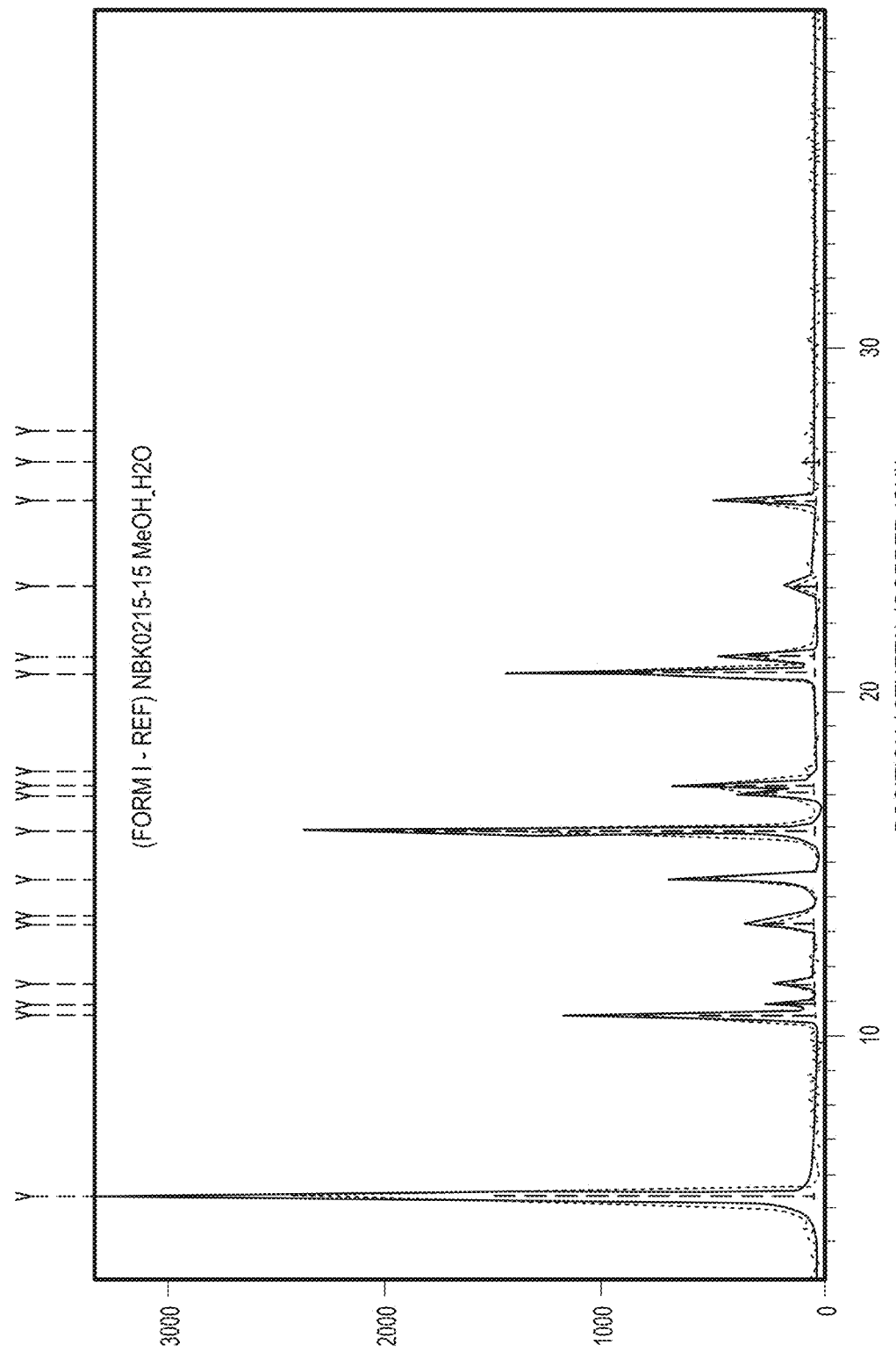
FIG. 1 shows an X-ray powder diffraction (XRPD) pattern of a channel hydrate of Form I of the Compound 1 hemi-citrate salt at about 90% relative humidity (Form IA) (high humidity pattern).

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For instance, where a range of values is provided, it is understood that each intervening value, to the tenth of the unit of the lower limit, unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure. In some embodiments, two opposing and open-ended ranges are provided for a feature, and in such description it is envisioned that combinations of those two ranges are provided herein. For example, in some embodiments, it is described that a feature is greater than about 10 units, and it is described (such as in another sentence) that the feature is less than about 20 units, and thus, the range of about 10 units to about 20 units is described herein.

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example, in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

The terms "aprotic solvent," "nonprotic solvent" or "non-protic solvent" as used herein refer to an organic solvent or a mixture of organic solvents that is not readily deprotonated in the presence of a strongly basic reactant. Non-limiting examples of non-protic solvents include ethers, dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, methyl isobutyl ketone, hexachloroacetone, acetone, ethyl methyl ketone, methyl ethyl ketone (MEK), ethyl acetate, isopropyl acetate, sulfolane, N,N-dimethylpropionamide, tetramethylurea, nitromethane, nitrobenzene, or hexamethylphosphoramide, diethoxymethane, tetrahydrofuran, 1,3-dioxane, 1,4-dioxane, furan, diethyl ether, tetrahydropyran, diisopropyl ether, dibutyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, and the like.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

The term "Compound 1," as used herein, refers to 3α-hydroxy-3β-methoxymethyl-21-(1'-imidazolyl)-5α-pregnan-20-one having the formula:

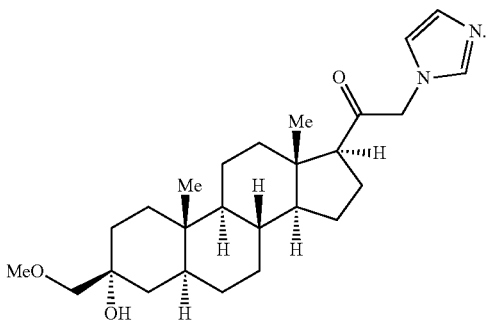

Compound 1 may be in any form, including amorphous, crystalline, salt form, free base, hydrated, anhydrous, and/or solvated.

The terms "Compound 1 hemi-citrate salt" and "hemi-citrate salt of Compound 1" are used herein interchangeably and refer to a salt of Compound 1 having a molar ratio of 3α-Hydroxy-3β-methoxymethyl-21-(1'-imidazolyl)-5α-pregnan-20-one to citrate of about 2:1 with the formula:

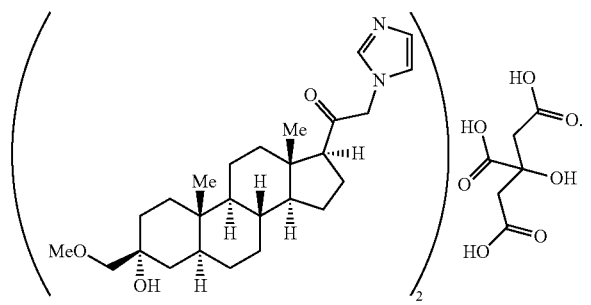

The terms "Compound 1 mono-citrate salt" and "mono-citrate salt of Compound 1" are used herein interchangeably and refer to a salt of Compound 1 having a molar ratio of 3α-Hydroxy-3β-methoxymethyl-21-(1'-imidazolyl)-5α-pregnan-20-one to citrate of 1:1 with the formula:

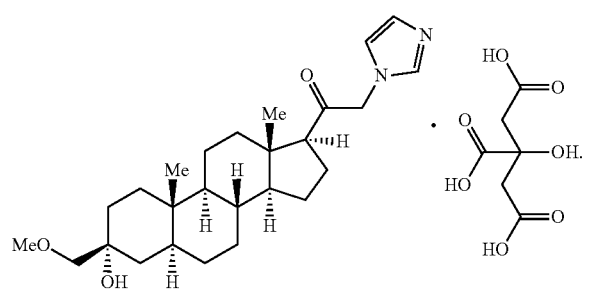

Mono-citrate salts of Compound 1 have been previously disclosed in, for example, U.S. Application Publication No. 2020/0071350, the entire content of which is incorporated herein by reference. As used herein, "Form A" of the Compound 1 mono-citrate salt refers to Form A of the Compound 1 mono-citrate salt as disclosed in U.S. Application Publication No. 2020/0071350.

As used herein, the term "polymorph" refers to a crystallographic form of a chemical substance. Polymorphism can be characterized as the ability of a compound to crystallize into different crystalline forms while maintaining the same structural formula (i.e., the covalent bonds in the compound are the same in different crystal forms). A crystalline polymorph of a given drug substance is chemically identical to any other crystalline polymorph of that drug substance in containing the same atoms bonded to one another in the same way, but differs in its crystal forms, which can affect one or more physical properties, such as stability, solubility, melting point, bulk density, flow properties, etc., or pharmacological properties such as bioavailability, etc.

As used herein, the term "channel hydrate" refers to a crystalline form of a compound capable of incorporating a variable number of water molecules into its crystal lattice. As such, the crystal lattice contains void volumes, or channels, into which the water molecules may by incorporated. In certain embodiments, the channel hydrate may contain 0% to 5% water by weight, and in certain embodiments, change in water content (e.g., a loss of water) may be fully reversible. In certain embodiments, the channel hydrate may be a sesquihydrate, and in certain embodiments, the channel hydrate may be dehydrated. A crystalline channel hydrate of a given drug substance may have an identical or a similar crystal structure to any other crystalline channel hydrate of the same drug, but may differ in physical properties, such as stability, solubility, melting point, bulk density, flow properties, etc., or pharmacological properties such as bioavailability, etc.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound, or a salt, solvate or ester thereof, that, when administered to a patient, is capable of performing the intended result. For example, an effective amount of a hemi-citrate salt of Compound 1 is that amount that is required to reduce at least one symptom of a disease, disorder, or condition, such as depression, in a patient. The actual amount that comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

As used herein, the term "in some embodiments," "in other embodiments," or the like, refers to embodiments of all aspects of the disclosure, unless the context clearly indicates otherwise.

The term "isomer" refers to compounds having the same chemical formula but may have different stereochemical formula, structural formula, or special arrangements of atoms. Examples of isomers include stereoisomers, diastereomers, enantiomers, conformational isomers, rotamers, geometric isomers, and atropisomers.

The term "peak" refers to a line having a substantial intensity in the XRPD diffractogram (or pattern) obtained from a sample using standard XRPD collection techniques, wherein substantial indicates that the peak is distinguishable from a baseline. For example, a peak may be a line in the XRPD diffractogram having an intensity that is, for example, at least about 10% of the intensity of the largest peak in the XRPD diffractogram.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "protic solvent" as used herein refers to a solvent or a solvent mixture that is capable of functioning as an acid for purposes of protonating any unreacted, strongly basic reaction intermediates. Non-limiting examples of protic solvents include water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, and the like.

Where an acid co-former is a solid at about 23° C. (i.e., room temperature) and there is no, or partial, proton transfer between Compound 1 and the acid co-former, a co-crystal of the co-former and Compound 1 is provided. As used herein, the term "salt" encompasses co-crystal forms of Compound 1.

The term "substantially similar" as used herein means an analytical spectrum, such as XRPD pattern, DSC thermogram, etc., which resembles the reference spectrum to a great degree. For example, one skilled in the art would be able to identify two XRPD patterns that are substantially similar by evaluating and comparing the overall patterns in both the peak locations and their intensity.

The term "treating" as used herein with regard to a patient, refers to improving at least one symptom of the patient's disorder. Treating can be improving, or at least partially ameliorating a disorder.

The term "therapeutic effect" as used herein refers to a desired or beneficial effect provided by the method and/or the composition. For example, the method for treating depression provides a therapeutic effect when the method reduces at least one symptom of depression in a patient.

As used herein, the symbol "≤" means "not more than" or "equal to or less than"; "<" means "less than"; "≥" means "not less than" or "equal to or more than"; and ">" means "more than". Furthermore, the numerical numbers, when used herein in connection with purity or impurity content, include not only the exact number but also the approximate range around the number. For example, the phrase "purity of 99.0%" denotes a purity of about 99.0%.

II. Hemi-Citrate Salt of Compound 1

The present disclosure relates to salts of Compound 1. In some embodiments, the salt is a hemi-citrate salt of Compound 1, wherein the molar ratio of 3α-Hydroxy-3β-methoxymethyl-21-(1'-imidazolyl)-5α-pregnan-20-one to citrate is about 2:1 ("Compound 1 hemi-citrate salt").

In some embodiments, the present disclosure provides a substantially pure hemi-citrate salt of Compound 1 having the formula:

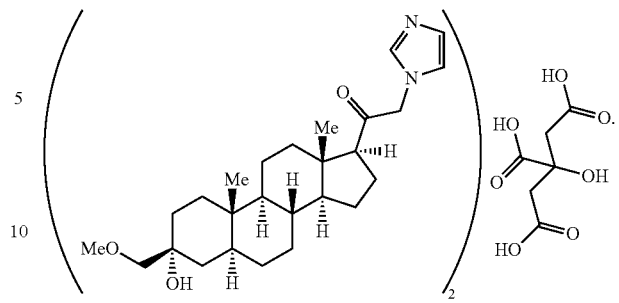

In some embodiments, the Compound 1 hemi-citrate salt is substantially free of a mono-citrate salt of Compound 1. The mono-citrate salt of Compound 1 has a molar ratio of 3α-Hydroxy-3β-methoxymethyl-21-(1'-imidazolyl)-5α-pregnan-20-one to citrate of 1:1. In some embodiments, the Compound 1 hemi-citrate salt is substantially free of the crystalline mono-citrate salt forms of Compound 1 as disclosed in U.S. Application Publication No. 2020/0071350, including, for example, substantially free of the crystalline Form A of the mono-citrate salt of Compound 1 and/or substantially free of the crystalline Form C of the mono-citrate salt of Compound 1. In some embodiments, the Compound 1 hemi-citrate salt contains less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, or less than about 0.5% by weight of a mono-citrate salt of Compound 1. In some embodiments, the Compound 1 hemi-citrate salt contains less than about 5% by weight of a mono-citrate salt of Compound 1. In some embodiments, the Compound 1 hemi-citrate salt contains less than about 4% by weight of a mono-citrate salt of Compound 1. In some embodiments, the Compound 1 hemi-citrate salt contains less than about 3% by weight of a mono-citrate salt of Compound 1. In some embodiments, the Compound 1 hemi-citrate salt contains less than about 2% by weight of a mono-citrate salt of Compound 1. In some embodiments, the Compound 1 hemi-citrate salt contains less than about 1% by weight of a mono-citrate salt of Compound 1. In some embodiments, the Compound 1 hemi-citrate salt contains less than about 0.5% by weight of a mono-citrate salt of Compound 1. In some embodiments, the Compound 1 hemi-citrate salt contains no more than about 1%, no more than about 0.9%, no more than about 0.8%, no more than about 0.7%, no more than about 0.6%, no more than about 0.5%, no more than about 0.4%, no more than about 0.3%, or no more than about 0.2% by weight of a mono-citrate salt of Compound 1. In some embodiments, the Compound 1 hemi-citrate salt contains no more than about 0.2% by weight of a mono-citrate salt of Compound 1.

In some embodiments, the Compound 1 hemi-citrate salt is crystalline Form I, as described herein. In some embodiments of the present disclosure, the crystalline Form I of the Compound 1 hemi-citrate salt is a hydrate. In some embodiments, the crystalline Form I of the Compound 1 hemi-citrate salt is a channel hydrate, for example a channel hydrate having a water content from about 0% to about 5% by weight, e.g., about 0%, about 0.25%, about 0.5%, about 0.75%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, or about 5% by weight. In some embodiments, the crystalline Form I of the Compound 1 hemi-citrate salt is a channel hydrate having a water content of about 5% by weight. In some embodiments, the crystalline Form I of the Compound 1 hemi-citrate salt is a channel hydrate having a water content of less than about 5% by weight. In some embodiments, the crystalline Form I of the Compound 1 hemi-citrate salt is a channel hydrate having a water content of less than about 4% by weight. In some embodiments, the crystalline Form I of the Compound 1 hemi-citrate salt is a channel hydrate having a water content of less than about 3% by weight. In some embodiments, the crystalline Form I of the Compound 1 hemi-citrate salt is a channel hydrate having a water content of less than about 2% by weight. In some embodiments, the crystalline Form I of the Compound 1 hemi-citrate salt is a channel hydrate having a water content of less than about 1% by weight. In some embodiments of the present disclosure, the crystalline Form I of the hemi-citrate salt of Compound 1 is a sesquihydrate. In other embodiments, the crystalline Form I of the hemi-citrate salt of Compound 1 is a monohydrate. In some embodiments, the crystalline Form I of the hemi-citrate salt of Compound 1 is a dehydrated hydrate.

In some embodiments of the present disclosure, the crystalline Form I of the Compound 1 hemi-citrate salt is a channel hydrate having a water content between about 2% and about 4% at room temperature by weight and relative humidity of about 20-90%, such as a water content of about 2%, about 2.25%, about 2.5%, about 2.75%, about 3%, about 3.25%, about 3.5%, about 3.75% or about 4% by weight. In some embodiments of the present disclosure, the crystalline Form I of the Compound 1 hemi-citrate salt is a channel hydrate having a water content between about 3% and about 5% by weight at 40° C. and relative humidity of about 20-90%, such as a water content of about 3%, about 3.25%, about 3.5%, about 3.75%, about 4%, about 4.25%, about 4.5%, or about 5% by weight. In some embodiments of the present disclosure, the crystalline Form I of the Compound 1 hemi-citrate salt is Form IA, as disclosed herein, and in some embodiments of the present disclosure, the crystalline Form I of the Compound 1 hemi-citrate salt is Form IB, as disclosed herein.

In some embodiments, the crystalline forms including channel hydrates thereof are characterized by the interlattice plane intervals determined by an X-ray powder diffraction pattern (XRPD). The XRPD diffractogram is typically represented by a diagram plotting the intensity of the peaks versus the location of the peaks, i.e., diffraction angle 2θ (two-theta) in degrees. The characteristic peaks of a given XRPD diffractogram can be selected according to the peak locations and their relative intensity to conveniently distinguish a particular crystalline structure from other crystalline forms of the same compound. The % intensity of the peaks relative to the most intense peak may be represented as I/Io.

Those skilled in the art recognize that the measurements of the XRPD peak locations and/or intensities for a given crystalline form of the same compound will vary within a margin of error. The values of degree 2θ allow appropriate error margins. Typically, the error margins are represented by "±". For example, the degree 2θ of about "8.716±0.3" denotes a range from about 8.716+0.3, i.e., about 9.016, to about 8.716−0.3, i.e., about 8.416. Depending on the sample preparation technique, the calibration technique applied to the instrument, human operational variation, and etc., those skilled in the art recognize that the appropriate error of margins for an XRPD can be about ±0.7; ±0.6; ±0.5; ±0.4; ±0.3; ±0.2; ±0.1; ±0.05; or less.

Additional details of the methods and equipment used for the XRPD analysis are described in the Examples section.

In some embodiments, the crystalline forms are characterized by Differential Scanning calorimetry (DSC). The DSC thermogram is typically expressed by a diagram plotting the normalized heat flow in units of Watts/gram ("W/g") versus the measured sample temperature in degree C. The DSC thermogram is usually evaluated for extrapolated onset and end (outset) temperatures, peak temperature, and heat of fusion. A peak characteristic value of a DSC thermogram is often used as the characteristic peak to distinguish this crystalline structure from others.

Those skilled in the art recognize that the measurements of the DSC thermogram for a given crystalline form of the same compound will vary within a margin of error. The values of a single peak characteristic value, expressed in degree C., allow appropriate error margins. Typically, the error margins are represented by "±". For example, the single peak characteristic value of about "53.09±2.0" denotes a range from about 53.09+2, i.e., about 55.09, to about 53.09−2, i.e., about 51.09. Depending on the sample preparation techniques, the calibration techniques applied to the instruments, human operational variations, and etc., those skilled in the art recognize that the appropriate error of margins for a single peak characteristic value can be ±2.5; ±2.0; ±1.5; ±1.0; ±0.5; or less.

Additional details of the methods and equipment used for the DSC thermogram analysis are described in the Examples section.

In some embodiments of the present disclosure, the hemi-citrate salt of Compound 1 is crystalline. In some embodiments, the hemi-citrate salt of Compound 1 is crystalline Form I ("Compound 1 hemi-citrate salt (Form I)"). It has been discovered that Form I of the Compound 1 hemi-citrate salt can exist in multiple states of hydration that may be determined, in part, by the relative humidity of the environment. These different hydrated forms of the Compound 1 hemi-citrate salt display different physical properties, some of which may be advantageous in developing pharmaceutical compositions, as set forth below. Moreover, the different hydrated forms can show different XRPD patterns. For instance, FIG. 1 shows an XRPD pattern of the channel hydrate Form IA of Compound 1 hemi-citrate salt at 90% relative humidity. As discussed in Example 1, this high hydration form was determined to be a sesquihydrate of the Compound 1 hemi-citrate salt, and is referred to herein as Compound 1 hemi-citrate salt Form IA. In certain embodiments, the Compound 1 hemi-citrate salt Form IA comprises at least one, at least two, at least three, at least four, at least five, at least six, at least seven, or all of the peaks selected from the group consisting of 5.3±0.2, 10.6±0.2, 14.5±0.2, 15.9±0.2, 17.2±0.2, 17.6±0.2 20.5±0.2, 21.0±0.2, and 25.5±0.2 degrees 2-theta. In some embodiments, the Compound 1 hemi-citrate salt Form IA exhibits an XRPD pattern at about 90% relative humidity comprising at least one, at least two, at least three, at least four, at least five, at least six, at least seven, or all of the peaks selected from the group consisting of 5.3±0.2, 10.6±0.2, 15.9±0.2, 17.2±0.2, and 20.5±0.2 degrees 2-theta. In some embodiments, the Compound 1 hemi-citrate salt Form IA exhibits an XRPD pattern, for example at about 90% relative humidity, comprising peaks at 5.3±0.2, 14.5±0.2, and 25.5±0.2 degrees 2-theta. In certain embodiments, the Compound 1 hemi-citrate salt Form IA has a XRPD pattern substantially the same as depicted in FIG. 1.

In some embodiments, the Form I of Compound 1 hemi-citrate salt exhibits an XRPD pattern at a high percentage relative humidity comprising at least one, at least two, at least three, at least four, at least five, at least six, at least In some embodiments, the Compound 1 hemi-citrate salt Form IA of the disclosure exhibits an XRPD pattern comprising the peaks shown in Table 1. The percent relative intensity of each peak may be calculated based on the height.

TABLE 1

XRPD pattern of the Compound 1 hemi-citrate salt Form IA at 90% relative humidity.

| No. | Pos. [°2 Th.] | FWHM Left [°2 Th.] | Area [cts*°2 Th.] | d-spacing [Å] | Height [cts] |
|---|---|---|---|---|---|
| 1 | 5.25578 | 0.15744 | 3897.915 | 16.8146 | 25098.18 |
| 2 | 8.776926 | 0.13776 | 109.5061 | 10.0752 | 805.8238 |
| 3 | 9.394155 | 0.31488 | 3.8454 | 9.41457 | 12.37993 |
| 4 | 10.55384 | 0.13776 | 1936.461 | 8.38253 | 14249.86 |
| 5 | 10.82057 | 0.0984 | 694.3102 | 8.17649 | 7152.921 |
| 6 | 11.45403 | 0.11808 | 477.89 | 7.72568 | 4102.764 |
| 7 | 13.15718 | 0.11808 | 944.378 | 6.7292 | 8107.641 |
| 8 | 13.46031 | 0.0984 | 274.1543 | 6.57833 | 2824.391 |
| 9 | 14.44271 | 0.17712 | 3395.246 | 6.133 | 19432.5 |
| 10 | 15.13749 | 0.0984 | 29.013 | 5.85304 | 298.8974 |
| 11 | 15.86345 | 0.15744 | 7721.828 | 5.58679 | 49719.88 |
| 12 | 16.21107 | 0.13776 | 1245.639 | 5.46776 | 9166.303 |
| 13 | 16.89059 | 0.13776 | 2492.92 | 5.24929 | 18344.69 |
| 14 | 17.18388 | 0.13776 | 3387.591 | 5.16035 | 24928.31 |
| 15 | 17.56941 | 0.13776 | 528.7267 | 5.04798 | 3890.748 |
| 16 | 18.4523 | 0.11808 | 57.5493 | 4.80839 | 494.0703 |
| 17 | 18.90822 | 0.11808 | 14.8909 | 4.69346 | 127.8407 |
| 18 | 19.74767 | 0.0984 | 138.5363 | 4.4958 | 1427.228 |
| 19 | 20.44583 | 0.13776 | 10963.77 | 4.34384 | 80679.24 |
| 20 | 20.91627 | 0.13776 | 3515.663 | 4.24719 | 25870.75 |
| 21 | 22.13471 | 0.0984 | 23.5194 | 4.01607 | 242.3019 |
| 22 | 22.90237 | 0.13776 | 993.2428 | 3.88317 | 7308.989 |
| 23 | 23.67076 | 0.11808 | 152.8218 | 3.75883 | 1312 |
| 24 | 24.12029 | 0.17712 | 127.8292 | 3.68978 | 731.6232 |
| 25 | 25.45671 | 0.15744 | 4453.208 | 3.49903 | 28673.64 |
| 26 | 26.15485 | 0.11808 | 246.4866 | 3.40719 | 2116.128 |
| 27 | 26.61792 | 0.25584 | 451.9395 | 3.34896 | 1790.758 |
| 28 | 27.40742 | 0.15744 | 525.1628 | 3.25426 | 3381.457 |
| 29 | 28.00035 | 0.11808 | 11.8285 | 3.18668 | 101.55 |
| 30 | 28.53804 | 0.13776 | 244.5173 | 3.12785 | 1799.332 |
| 31 | 29.41477 | 0.11808 | 69.2903 | 3.03659 | 594.8685 |
| 32 | 29.79816 | 0.13776 | 90.5917 | 2.99839 | 666.6381 |
| 33 | 30.07974 | 0.17712 | 380.799 | 2.97096 | 2179.481 |
| 34 | 30.58038 | 0.23616 | 90.3382 | 2.92345 | 387.7842 |
| 35 | 31.42192 | 0.21648 | 274.1865 | 2.84705 | 1283.965 |
| 36 | 32.05774 | 0.15744 | 220.9114 | 2.79202 | 1422.421 |
| 37 | 32.73671 | 0.15744 | 12.7834 | 2.73565 | 82.31068 |
| 38 | 33.2967 | 0.17712 | 154.3966 | 2.69091 | 883.6799 |
| 39 | 34.12024 | 0.11808 | 62.1183 | 2.62782 | 533.2959 |
| 40 | 34.79246 | 0.1968 | 351.038 | 2.57857 | 1808.232 |
| 41 | 35.95503 | 0.17712 | 279.1031 | 2.49782 | 1597.431 |
| 42 | 36.349 | 0.13776 | 114.5345 | 2.47165 | 842.8262 |
| 43 | 37.24761 | 0.1968 | 45.3004 | 2.41406 | 233.3468 |
| 44 | 38.10058 | 0.15744 | 134.9359 | 2.36195 | 868.8351 |
| 45 | 38.50546 | 0.23616 | 114.1878 | 2.33805 | 490.1606 | seven, or all of the peaks selected from the group consisting of 5.2±0.2, 10.6±0.2, 14.4±0.2, 15.9±0.2, 17.2±0.2, 20.5±0.2, 22.9±0.2 and 25.5±0.2 degrees 2-theta. In such embodiments, a high percentage relative humidity is greater than about 30%, greater than about 40%, greater than about 50%, greater than about 60%, greater than about 70%, greater than about 80%, or greater than about 90% relative humidity; or between about 30% and about 99%, between about 30% and about 95%, between about 30% and about 90%, between about 40% and about 99%, between about 40% and about 95%, between about 40% and about 90%, between about 50% and about 99%, between about 50% and about 95%, between about 50% and about 90%, between about 60% and about 99%, between about 60% and about 95%, between about 60% and about 90%, between about 70% and about 99%, between about 70% and about 95%, or between about 80% and about 90% relative humidity.

Figure 10:
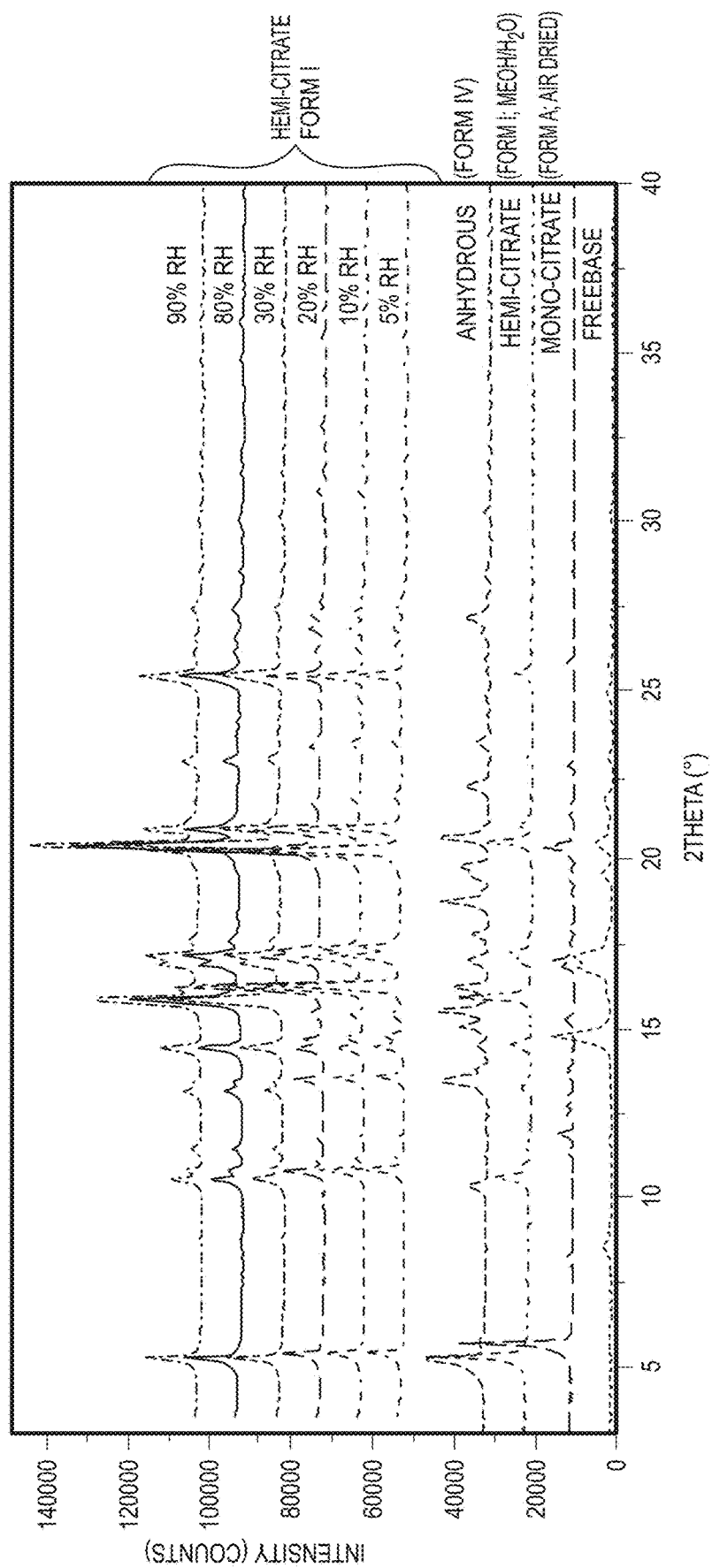
FIG. 10 shows XRPD patterns of the Compound 1 hemi-citrate salt Form I at various relative humidity (RH) levels (5% RH, 10% RH, 20% RH, 30% RH, 80% RH, and 90% RH). Also shown for comparison are XRPD patterns of the Compound 1 mono-citrate salt anhydrate ("Form IV"), Compound 1 mono-citrate salt ("Form A; air dried"), Compound 1 hemi-citrate salt recrystallized from methanol and water ("Form I; MeOH/$H_2O$"), and the freebase of Compound 1.

As depicted in FIG. 10, the Compound 1 hemi-citrate salt Form IA may persist at a relative humidity of lower than 90%. For instance, Compound 1 hemi-citrate salt Form IA may be the dominant form at a relative humidity from about 30% to about 90%. Accordingly, in some embodiments, the Compound 1 hemi-citrate salt Form IA exhibits an XRPD pattern at about 30% relative humidity, at about 40% relative humidity, at about 50% relative humidity, at about 60% relative humidity, at about 70% relative humidity, at about 80% relative humidity, and/or at about 90% relative humidity that is substantially similar to FIG. 1.

Figure 2:
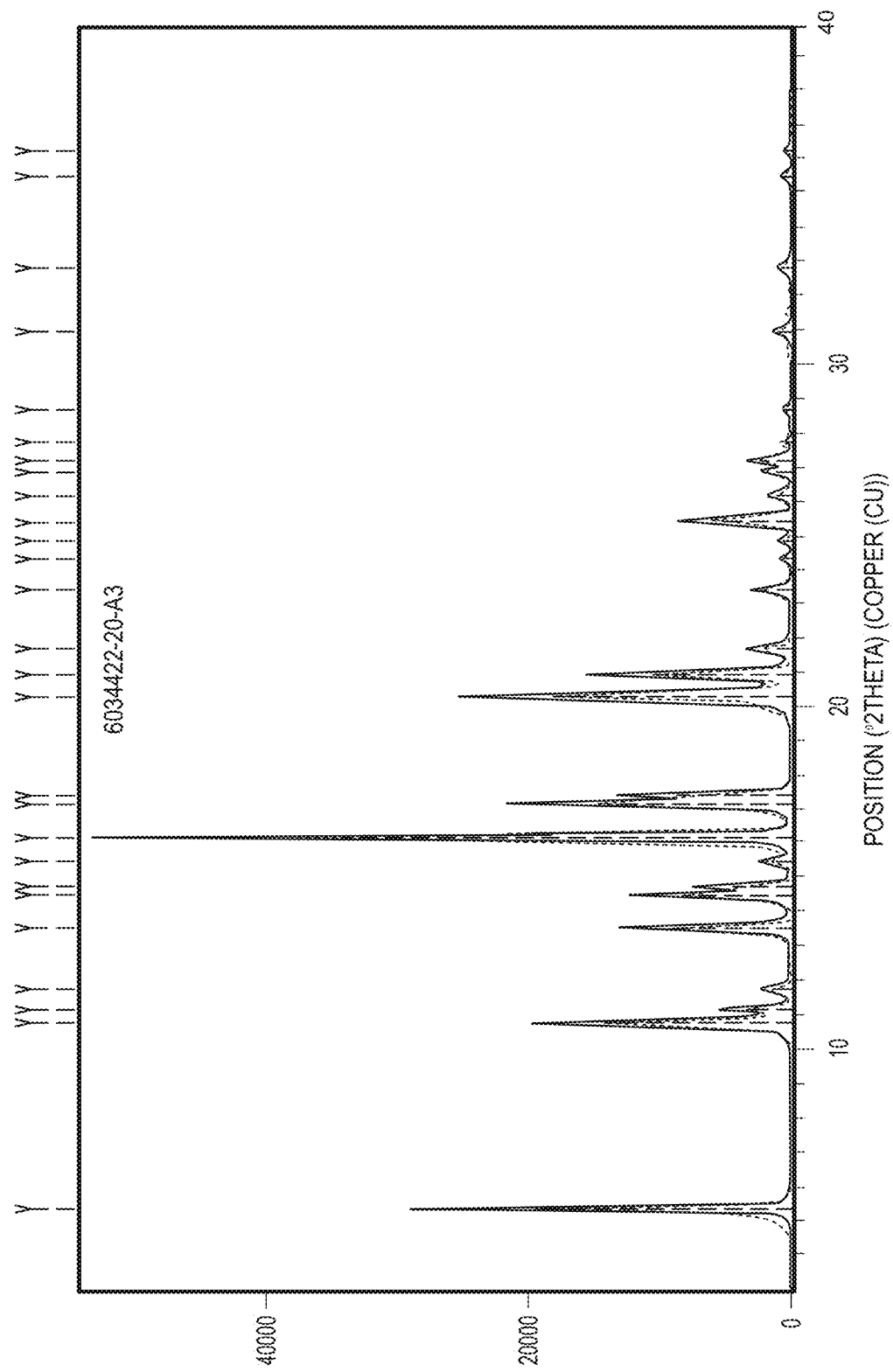
FIG. 2 shows an XRPD pattern of a channel hydrate of Form I of the Compound 1 hemi-citrate salt at about 5% relative humidity (Form IB) (low humidity pattern).

As further shown in FIG. 10, the peaks in the XRPD pattern shift to the right at a relative humidity of lower than about 30%, indicating the presence of Form IB of the Compound 1 hemi-citrate salt. For instance, at a relative humidity of 20% or less, a new channel hydrate may become the dominant form, which is distinct from the channel hydrate Form IA of Compound 1 hemi-citrate salt. FIG. 2 shows an XRPD pattern of Form I of the hemi-citrate salt of Compound 1 at a very low relative humidity (5%). The low hydration form is referred to herein as Compound 1 hemi-citrate salt Form IB. In some embodiments, the Compound 1 hemi-citrate salt Form IB exhibits an XRPD pattern comprising at least one, at least two, at least three, at least four, at least five, at least six, at least seven, at least eight, or all of the peaks selected from the group consisting of 5.4±0.2, 10.9±0.2, 14.5±0.2, 16.3±0.2, 17.1±0.2, 17.5±0.2, 20.3±0.2, 21.0±0.2, and 25.5±0.2 degrees 2-theta. In some embodiments, the Compound 1 hemi-citrate salt Form IB exhibits an XRPD pattern comprising at least one, at least two, at least three, at least four, or all of the peaks selected from the group consisting of 10.9±0.2, 16.3±0.2, 17.1±0.2, 20.3±0.2, and 21.0±0.2 degrees 2-theta. In some embodiments, the Compound 1 hemi-citrate salt Form IB exhibits an XRPD pattern at about 5% relative humidity comprising peaks at 5.4±0.2, 14.5±0.2, and 25.5±0.2.

20.3±0.2, 23.5±0.2 and 25.5±0.2 degrees 2-theta. In such embodiments, a low percentage relative humidity is less than about 30%, less than about 25%, less than about 20%, less than about 15%, less than about 10%, or less than about 5% relative humidity; or between about 1% and about 30%, between about 5% and about 30%, between about 10% and about 30%, between about 15% and about 30%, between about 20% and about 30%, or between about 25% and about 30% relative humidity.

In some embodiments, the Compound 1 hemi-citrate salt Form IB exhibits an XRPD pattern comprising the peaks shown in Table 2. In some embodiments, the Compound 1 hemi-citrate salt Form IB exhibits a XRPD pattern substantially the same as depicted in FIG. 2. In some embodiments, the Compound 1 hemi-citrate salt Form IB has less than 5% water by weight, such as less than 3%, less than 2%, less than 1%, or 0% water by weight.

TABLE 2

XRPD pattern of the Compound 1 hemi-citrate salt Form IB at about 5% relative humidity.

| No. | Pos. [°2 Th.] | FWHM Left [°2 Th.] | Area [cts*°2 Th.] | d-spacing [Å] | Height [cts] |
| --- | --- | --- | --- | --- | --- |
| 1 | 5.401141 | 0.11808 | 1688.551 | 16.36239 | 14496.49 |
| 2 | 8.323991 | 0.31488 | 29.903 | 10.62238 | 96.27089 |
| 3 | 9.762059 | 0.15744 | 20.0433 | 9.06057 | 129.0566 |
| 4 | 10.86104 | 0.11808 | 2676.698 | 8.14612 | 22979.89 |
| 5 | 11.25084 | 0.13776 | 504.3272 | 7.86474 | 3711.199 |
| 6 | 11.81664 | 0.13776 | 207.7799 | 7.48941 | 1528.993 |
| 7 | 13.62526 | 0.13776 | 1716.723 | 6.49906 | 12632.88 |
| 8 | 14.49067 | 0.13776 | 1805.433 | 6.11281 | 13285.67 |
| 9 | 14.83302 | 0.13776 | 1092.784 | 5.97249 | 8041.484 |
| 10 | 15.44259 | 0.15744 | 859.3604 | 5.73808 | 5533.313 |
| 11 | 16.32522 | 0.15744 | 10236.99 | 5.42978 | 65914.71 |
| 12 | 17.14861 | 0.13776 | 3660.487 | 5.17089 | 26936.47 |
| 13 | 17.45461 | 0.13776 | 2867.912 | 5.08092 | 21104.14 |
| 14 | 17.73467 | 0.0984 | 237.1892 | 5.00131 | 2443.571 |
| 15 | 18.31781 | 0.15744 | 42.7261 | 4.84339 | 275.1078 |
| 16 | 18.96523 | 0.31488 | 32.9761 | 4.67948 | 106.1644 |
| 17 | 20.31092 | 0.15744 | 9496.987 | 4.37238 | 61149.9 |
| 18 | 20.94755 | 0.17712 | 4759.29 | 4.24092 | 27239.52 |
| 19 | 21.94565 | 0.1968 | 701.8529 | 4.05024 | 3615.313 |
| 20 | 23.53577 | 0.13776 | 590.8894 | 3.78008 | 4348.186 |
| 21 | 23.78408 | 0.11808 | 85.9848 | 3.74117 | 738.1938 |
| 22 | 24.45675 | 0.15744 | 195.8492 | 3.63978 | 1261.048 |
| 23 | 25.4773 | 0.1968 | 4269.918 | 3.49625 | 21994.77 |
| 24 | 26.37809 | 0.15744 | 509.0292 | 3.37886 | 3277.575 |
| 25 | 26.81156 | 0.13776 | 587.1546 | 3.32521 | 4320.702 |
| 26 | 26.97866 | 0.13776 | 574.6087 | 3.30499 | 4228.38 |
| 27 | 27.40378 | 0.1968 | 868.4664 | 3.25468 | 4473.556 |
| 28 | 27.78476 | 0.1968 | 247.1422 | 3.21091 | 1273.054 |
| 29 | 28.1297 | 0.17712 | 69.6186 | 3.17232 | 398.4579 |
| 30 | 28.7959 | 0.15744 | 168.5303 | 3.10043 | 1085.145 |
| 31 | 29.27839 | 0.11808 | 16.222 | 3.05042 | 139.2682 |
| 32 | 30.30535 | 0.15744 | 211.142 | 2.94935 | 1359.517 |
| 33 | 30.87199 | 0.11808 | 302.5924 | 2.8965 | 2597.806 |
| 34 | 31.18179 | 0.15744 | 187.8597 | 2.86842 | 1209.605 |
| 35 | 31.78271 | 0.21648 | 297.2563 | 2.81555 | 1391.997 |
| 36 | 32.34203 | 0.15744 | 75.2186 | 2.76812 | 484.3233 |
| 37 | 33.01845 | 0.25584 | 467.8059 | 2.71295 | 1853.626 |
| 38 | 33.90832 | 0.15744 | 12.5301 | 2.64376 | 80.67947 |
| 39 | 34.70195 | 0.25584 | 287.1756 | 2.58509 | 1137.9 |
| 40 | 35.38442 | 0.15744 | 276.8927 | 2.53678 | 1782.877 |
| 41 | 36.3065 | 0.25584 | 294.3483 | 2.47444 | 1166.321 |
| 42 | 38.16241 | 0.0984 | 80.2342 | 2.35827 | 826.5886 |

In some embodiments, the Compound 1 hemi-citrate salt Form IB exhibits an XRPD pattern at a low percentage relative humidity comprising at least one, at least two, at least three, at least four, at least five, at least six, at least seven, or all of the peaks selected from the group consisting of 5.4±0.2, 10.9±0.2, 14.5±0.2, 16.3±0.2, 17.4±0.2, In some embodiments, the Compound 1 hemi-citrate salt Form IB exhibits an XRPD pattern at about 5% relative humidity that is substantially similar to FIG. 2.

In some embodiments, the Compound 1 hemi-citrate salt Form I exhibits an XRPD pattern at 90% relative humidity (RH) comprising the peaks shown in Table 4. In some embodiments, the Compound 1 hemi-citrate salt Form I exhibits an XRPD pattern at 80% RH comprising the peaks shown in Table 4. In some embodiments, the Compound 1 hemi-citrate salt Form I exhibits an XRPD pattern at 30% RH comprising the peaks shown in Table 4. In some embodiments, the Compound 1 hemi-citrate salt Form I exhibits an XRPD pattern at 20% RH comprising the peaks shown in Table 4. In some embodiments, the Compound 1 hemi-citrate salt Form I exhibits an XRPD pattern at 10% RH comprising the peaks shown in Table 4. In some embodiments, the Compound 1 hemi-citrate salt Form I exhibits an XRPD pattern at 5% RH comprising the peaks shown in Table 4. In some embodiments, the Compound 1 hemi-citrate salt Form I exhibits an XRPD pattern at 90% RH comprising at least the three most intense peaks or at least the five most intense peaks shown in Table 4. In some embodiments, the Compound 1 hemi-citrate salt Form I exhibits an XRPD pattern at 80% RH comprising at least the three most intense peaks or at least the five most intense peaks shown in Table 4. In some embodiments, the Compound 1 hemi-citrate salt Form I exhibits an XRPD pattern at 30% RH comprising at least the three most intense peaks or at least the five most intense peaks shown in Table 4. In some embodiments, the Compound 1 hemi-citrate salt Form I exhibits an XRPD pattern at 20% RH comprising at least the three most intense peaks or at least the five most intense peaks shown in Table 4. In some embodiments, the Compound 1 hemi-citrate salt Form I exhibits an XRPD pattern at 10% RH comprising at least the three most intense peaks or at least the five most intense peaks shown in Table 4. In some embodiments, the Compound 1 hemi-citrate salt Form I exhibits an XRPD pattern at 5% RH comprising at least the three most intense peaks or at least the five most intense peaks shown in Table 4.

In some embodiments, the crystalline Compound 1 hemi-citrate salt Form I exhibits an XRPD pattern comprising peaks at (1) between 5.3 and 5.5 degrees 2-theta, (2) between 10.6 and 11 degrees 2-theta, and (3) between 15.9 and 16.3 degrees 2-theta.

In some embodiments, the crystalline Compound 1 hemi-citrate salt Form I has a water content of about 4.4% by weight and exhibits a differential scanning calorimetry (DSC) thermogram having a peak value at about 65.2° C. with the error of margin of about ±2.5° C., such as about ±2.0° C., about ±1.5° C., about ±1.0° C., about ±0.5° C. or less. In some embodiments, the crystalline Compound 1 hemi-citrate salt Form I has a water content of about 3.70% by weight and exhibits a differential scanning calorimetry (DSC) thermogram having a peak value at about 71° C. with the error of margin of about ±2.5° C., such as about ±2.0° C., about ±1.5° C., about ±1.0° C., about ±0.5° C., or less. In another embodiment, the crystalline Compound 1 hemi-citrate salt Form I exhibits a DSC thermogram having a peak value at about 126.3° C. with the error of margin of about ±2.5° C., such as about ±2.0° C., about ±1.5° C., about ±1.0° C., about ±0.5° C., or less. In some embodiments, the crystalline Compound 1 hemi-citrate salt Form I exhibits a DSC thermogram that is substantially similar to FIG. 3.

Figure 3:
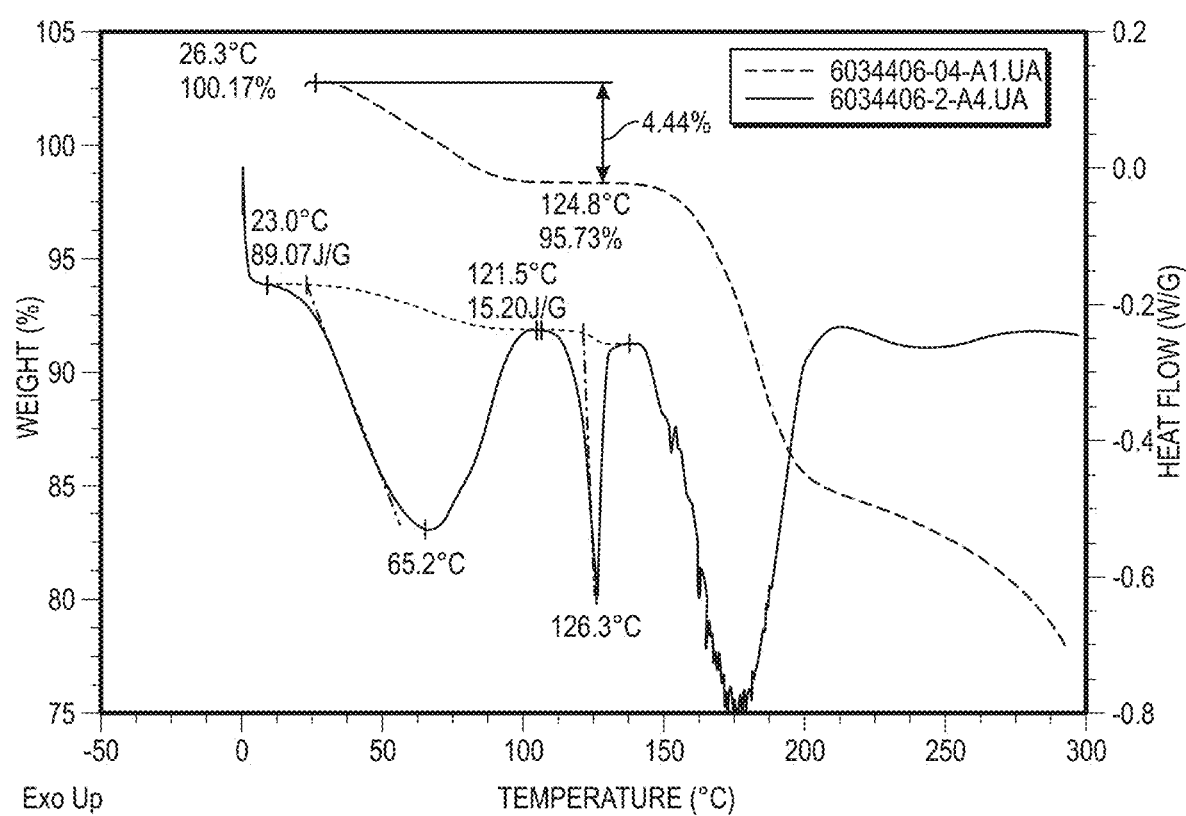
FIG. 3 shows a differential scanning calorimetry (DSC) thermogram and a thermogravimetric analysis (TGA) thermogram of the Compound 1 hemi-citrate salt Form I.

In some embodiments, the Compound 1 hemi-citrate salt Form I exhibits a thermogravimetric analysis (TGA) thermogram that is substantially similar to FIG. 3. In some embodiments, the TGA thermogram of the Compound 1 hemi-citrate salt Form I exhibits a TGA thermogram with a weight loss of about 0.0% to 4.4% in the temperature range of about 25° C. and about 125° C., such as the temperature range of about 25° C. and about 100° C.

Figure 4:
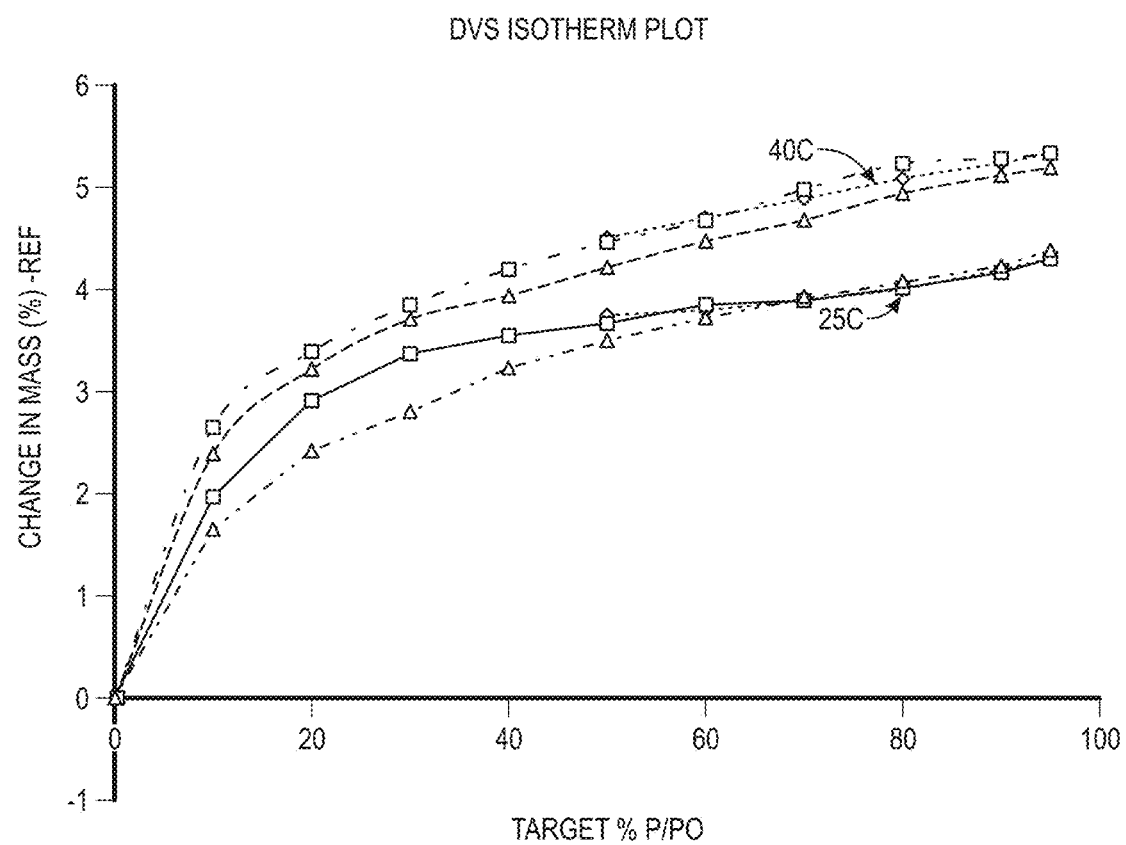
FIG. 4 shows a dynamic vapor sorption (DVS) isotherm plot for the Compound 1 hemi-citrate salt Form I.

In some embodiments, the Compound 1 hemi-citrate salt Form I exhibits a DVS isotherm plot that is substantially similar to FIG. 4. In some embodiments, the Compound 1 hemi-citrate salt Form I exhibits a gravimetric moisture sorption of about 1.2% (by weight) from about 20% to about 80% RH at 25° C. In some embodiments, the Compound 1 hemi-citrate salt Form I exhibits about a 4.3% weight loss of water from about 95% to about 0% RH at 25° C. In some embodiments, the Compound 1 hemi-citrate salt Form I exhibits a gravimetric moisture sorption of about 1.8% (by weight) from about 20% to about 80% at 40° C. In some embodiments, the Compound 1 hemi-citrate salt Form I exhibits about a 5.4% weight loss of water from about 95% to about 0% RH at 40° C. In some embodiments, the water loss is fully reversible.

In some embodiments of the present disclosure, the Compound 1 hemi-citrate salt Form I has a water content between about 2% and about 4% by weight at room temperature and relative humidity of about 20-90%, such as a water content about 2%, about 2.25%, about 2.5%, about 2.75%, about 3%, about 3.25%, about 3.5%, about 3.75% or about 4% by weight. In some embodiments of the present disclosure, the Compound 1 hemi-citrate salt Form I has a water content between about 3% and about 5% by weight at 40° C. and relative humidity of about 20-90%, such as a water content of about 3%, about 3.25%, about 3.5%, about 3.75%, about 4%, about 4.25%, about 4.5%, or about 5% by weight.

In some embodiments, the Compound 1 hemi-citrate salt Form I is defined by unit cell parameters substantially similar to the following: a=34.7 Å; b=8.3 Å; c=31.7 Å; α=90°; β=108.5°; γ=90°; Space group C2; Molecules/asymmetric unit 2, wherein the crystalline form is at about 173 K.

III. Methods of Preparing Hemi-Citrate Salts of Compound 1

A hemi-citrate salt of Compound 1 (and channel hydrates thereof) may be prepared, for example, by mixing Compound 1 free base and citric acid in a suitable solvent to provide the Compound 1 salt as a suspension in the suitable solvent. In some embodiments, about a 1:0.5 ratio of Compound 1 freebase to citric acid are mixed. In some embodiments, the suitable solvent is selected from the group consisting of tetrahydrofuran, 2-methyltetrahydrofuran, and methyl tert-butyl ether. In some embodiments, the Compound 1 hemi-citrate salt (and channel hydrates thereof) may be prepared by slow evaporation, slow cooling or antisolvent addition to the mixture of Compound 1 free base and citric acid.

In some embodiments, a hemi-citrate salt (and channel hydrates thereof) of Compound 1 is prepared from a mono-citrate salt of Compound 1.

In some embodiments, the method of preparing a hemi-citrate salt of Compound 1 comprises: (a) dissolving a mono-citrate salt of Compound 1 in a $C_1$-$C_3$ alcohol; and (b) adding the solution of Step (a) to water to provide the hemi-citrate salt of Compound 1. In some embodiments, the method further comprises Step (c) isolating and drying the hemi-citrate salt of Compound 1. In some embodiments, the present method is used to prepare a crystalline form of a hemi-citrate salt of Compound 1. In some embodiments, the crystalline form of the hemi-citrate salt of Compound 1 is Form I, including, for example, Form IA or Form IB as disclosed herein.

In some embodiments, the $C_1$-$C_3$ alcohol is methanol, ethanol or isopropanol. In some embodiments, the $C_1$-$C_3$ alcohol is methanol or ethanol. In some embodiments, the $C_1$-$C_3$ alcohol is methanol. In some embodiments, the $C_1$-$C_3$ alcohol is an alcohol with a water activity greater than about 0.75.

In some embodiments, the mono-citrate salt of Compound 1 is dissolved in $C_1$-$C_2$ alcohol. In some embodiments, the $C_1$-$C_2$ alcohol is methanol. In some embodiments, the $C_1$-$C_2$ alcohol is ethanol.

In some embodiments, the method of preparing a hemi-citrate salt of Compound 1 comprises: (a) suspending a mono-citrate salt of Compound 1 in water; and (b) isolating the hemi-citrate salt of Compound 1. In some embodiments, the method further comprises drying the hemi-citrate salt of Compound 1. In some embodiments, the present method is used to prepare a crystalline form of a hemi-citrate salt of Compound 1. In some embodiments, the crystalline form of the hemi-citrate salt of Compound 1 is Form I, including, for example, Form IA or Form IB as disclosed herein.

In some embodiments, the present disclosure provides further methods of making crystalline forms of a hemi-citrate salt of Compound 1. For example, in some embodiments, the hemi-citrate salt of Compound 1 is suspended in a suitable solvent for a time sufficient to provide a suspension of a crystalline form of the hemi-citrate salt of Compound 1.

In some embodiments, a hemi-citrate salt of Compound 1 is dissolved in a suitable solvent to provide a solution and a crystalline form of the hemi-citrate salt of Compound 1 is precipitated from the solution. In some embodiments, a hemi-citrate salt of Compound 1 is dissolved by heating a mixture of the hemi-citrate salt of Compound 1 and a suitable solvent. In some embodiments, a crystalline form of the hemi-citrate salt of Compound 1 is precipitated from the solution by cooling the solution. In some embodiments, the crystalline form of the hemi-citrate salt of Compound 1 is precipitated from the solution by adding an anti-solvent (i.e., a solvent that decreases the solubility of the crystalline form of the hemi-citrate salt of Compound 1 in the solution) to the solution. In some embodiments, a crystalline form of the hemi-citrate salt of Compound 1 is precipitated from the solution by evaporating a portion of the suitable solvent from the solution. In some embodiments, the crystalline form of the hemi-citrate salt is crystalline Form I, including, for example, Form IA or Form IB as disclosed herein. In some embodiments, the suitable solvent comprises water.

In some embodiments, the suitable solvent comprises a non-protic solvent. In some embodiments, the non-protic solvent comprises at least one solvent selected from dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, methyl ethyl ketone (MEK), hexachloroacetone, acetone, ethyl methyl ketone, ethyl acetate, sulfolane, N,N-dimethylpropionamide, tetramethylurea, nitromethane, nitrobenzene, hexamethylphosphoramide, diethoxymethane, tetrahydrofuran, toluene, 1,3-dioxane, 1,4-dioxane, furan, diethyl ether, tetrahydropyran, diisopropyl ether, dibutyl ether, ethylene glycol dimethyl ether, ethylene glycol diethyl ether, diethylene glycol dimethyl ether, diethylene glycol diethyl ether, triethylene glycol dimethyl ether, anisole, and t-butyl methyl ether. In some embodiments, the non-protic solvent is acetone. In some embodiments, the non-protic solvent is ethyl acetate. In some embodiments, the non-protic solvent is acetonitrile.

In some embodiments, the suitable solvent comprises a protic solvent. In some embodiments, the protic solvent comprises at least one solvent selected from water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, and glycerol. In some embodiments, the protic solvent comprises a mixture of 2-propanol and water.

In some embodiments, the suitable solvent is a single solvent. In some embodiments, the solvent is a mixture of solvents. In some embodiments, the suitable solvent is a mixture of a protic solvent and a non-protic solvent.

In certain embodiments, the Compound 1 hemi-citrate salt is isolated after it is prepared. The isolation of the Compound 1 hemi-citrate salt may be accomplished using methods such as filtration, decantation, centrifugation or any other suitable separation technique or techniques.

In certain embodiments, the isolated Compound 1 hemi-citrate salt is optionally washed with a liquid such as an anti-solvent, acetonitrile, methanol, ethanol, ethyl acetate, methyl ethyl ketone, acetone, tetrahydrofuran, or a combination thereof.

In some embodiments, the hemi-citrate salt of Compound 1 prepared by the embodiments above is substantially pure. For example, in some embodiments, the chemical purity of the hemi-citrate salt of Compound 1 is at least about 99.9%, about 99.8%, about 99.7%, about 99.6%, about 99.5%, about 99.4%, about 99.3%, about 99.2%, about 99.1%, about 99.0%, about 98%, about 97%, about 96%, or about 95% pure. Chemical purity may be determined using methods known to those skilled in the area (for example, HPLC chromatography with a suitable solvent and column detecting a wavelength of 210 nm). In some embodiments, the substantial purity is determined on a weight percent basis. In some embodiments, the substantial purity is determined on an area under the curve basis.

In some embodiments, the hemi-citrate salt of Compound 1 prepared by the embodiments above is crystalline. In certain embodiments, the crystalline hemi-citrate salt of Compound 1 prepared by the embodiments above is substantially pure. For example, in some embodiments, the polymorphic purity of the crystalline hemi-citrate salt of Compound 1 is at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, about 90%, about 85%, about 80%, about 75%, about 70%, about 65%, about 60%, about 55% or about 50% pure. Polymorphic purity may be determined using methods known to those skilled in the art (including, among others, X-ray powder crystallography as described in Shah, B., et al., Analytical techniques for quantification of amorphous/crystalline phases in pharmaceutical solids, J. Pharm. Sci. 2006, 95(8), pages 1641-1665 which is hereby incorporated by reference in its entirety).

In some embodiments, the hemi-citrate salt of Compound 1 prepared by the embodiments above is epimerically enriched at one or more positions compared to the epimeric purity of the Compound 1 free base starting material. For example, in some embodiments, the hemi-citrate salt of Compound 1 may comprise at least about 8:1, about 9:1, about 10:1, about 11:1, about 12:1, about 13:1, about 14:1, about 15:1, or about 20:1 of 17-13:17a epimer of Compound 1. In some embodiments, the hemi-citrate salt of Compound 1 may comprise at least about 8:1, about 9:1, about 10:1, about 11:1, about 12:1, about 13:1, about 14:1, about 15:1, or about 20:1 of 3α-hydroxy:3β-hydroxy of Compound 1. In other embodiments, the epimeric purity of the hemi-citrate salt of Compound 1 prepared by the methods described herein is substantially the same as the epimeric purity of the Compound 1 free base starting material.

IV. Pharmaceutical Compositions

In one aspect, the present disclosure provides a pharmaceutical composition comprising a hemi-citrate salt of Compound 1, as disclosed herein, having the formula:

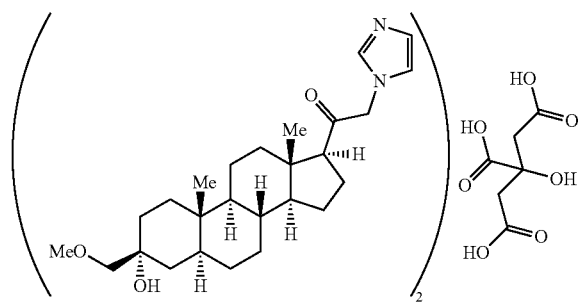

and a pharmaceutically acceptable excipient. In some embodiments, the composition is substantially free of a mono-citrate salt of Compound 1. In some embodiments, the composition contains less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, or less than about 0.5% by weight of a mono-citrate salt of Compound 1. In some embodiments, the composition contains less than about 5% by weight of a mono-citrate salt of Compound 1. In some embodiments, the composition contains less than about 1% by weight of a mono-citrate salt of Compound 1. In some embodiments, the composition contains less than about 0.5% by weight of a mono-citrate salt of Compound 1. In some embodiments, the composition contains no more than about 1%, no more than about 0.9%, no more than about 0.8%, no more than about 0.7%, no more than about 0.6%, no more than about 0.5%, no more than about 0.4%, no more than about 0.3%, no more than about 0.2%, or no more than about 0.1% by weight of a mono-citrate salt of Compound 1. In some embodiments, the composition contains no more than about 0.2% by weight of a mono-citrate salt of Compound 1. In some embodiments, the composition contains no more than about 0.1% by weight of a mono-citrate salt of Compound 1.

In some embodiments, the chemical purity of the hemi-citrate salt of Compound 1 in the composition is at least about 99%, at least about 98.0%, at least about 97.0%, at least about 96.0%, at least about 95.0%, at least about 94.0%, at least about 93.0%, at least about 92.0%, at least about 91.0%, or at least about 90.0% as determined by HPLC analysis after the composition is stored at about 40° C. and about 75% relative humidity for about 6 months. In some embodiments, the chemical purity of the hemi-citrate salt of Compound 1 in the composition is at least about 98.0% as determined by HPLC analysis after the composition is stored at about 40° C. and about 75% relative humidity for about 6 months. In some embodiments, the hemi-citrate salt of Compound 1 is crystalline Form I disclosed herein.

In some embodiments, the composition comprises no more than about 1%, no more than about 0.9%, no more than about 0.8%, no more than about 0.7%, no more than about 0.6%, no more than about 0.5%, no more than about 0.45%, no more than about 0.4%, no more than about 0.35%, no more than about 0.3%, no more than about 0.25%, no more than about 0.2%, no more than about 0.15%, or no more than about 0.1% by weight of the C-17 epimer of Compound 1 after the composition is stored at about 40° C. and about 75% relative humidity for about 6 months. In some embodiments, the composition comprises no more than about 0.5% by weight of the C-17 epimer of Compound 1 after the composition is stored at about 40° C. and about 75% relative humidity for about 6 months. The C-17 epimer of Compound 1 is depicted by the formula:

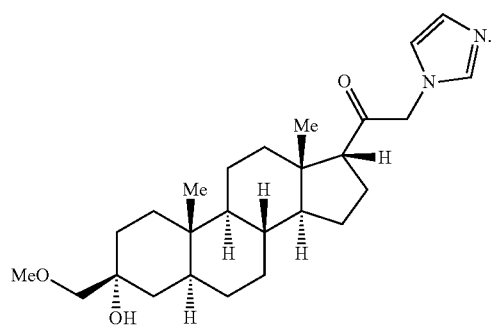

In some embodiments of the present disclosure, the Compound 1 hemi-citrate salt in the compositions disclosed herein is a channel hydrate. In some embodiments, the Compound 1 hemi-citrate salt has a water content from about 0% to about 5% by weight, e.g., about 0%, about 0.25%, about 0.5%, about 0.75%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, or about 5% by weight. In some embodiments, the Compound 1 hemi-citrate salt has a water content of about 5% by weight. In some embodiments, the Compound 1 hemi-citrate salt has a water content of less than about 5%, less than about 4%, less than about 3%, less than about 2%, or less than about 1% by weight. In some embodiments of the present disclosure, the hemi-citrate salt of Compound 1 is a sesquihydrate.

In some embodiments of the present disclosure, the Compound 1 hemi-citrate salt in the compositions disclosed herein has a water content between about 2% and about 4% by weight at room temperature and relative humidity of about 20-90%, such as a water content of about 2%, about 2.25%, about 2.5%, about 2.75%, about 3%, about 3.25%, about 3.5%, about 3.75% or about 4% of by weight. In some embodiments of the present disclosure, the Compound 1 hemi-citrate salt has a water content between about 3% and about 5% by weight at 40° C. and relative humidity of about 20-90%, such as a water content of about 3%, about 3.25%, about 3.5%, about 3.75%, about 4%, about 4.25%, about 4.5%, or about 5% by weight.

The compositions disclosed herein may be administered by any suitable route, including, but not limited to, orally, parenterally, rectally, topically, and locally. The compositions may be in liquid, semi-liquid, or solid form and may be formulated using methods known to those skilled in the art in a manner suitable for each route of administration.

In some embodiments, the compositions of the disclosure are formulated for oral administration. Orally administered dosage forms include, for example, solid dosage forms (such as tablets, capsules, pills, granules, and the like) and liquid dosage forms (such as oral solutions, oral suspensions, syrups, and the like). In some embodiments, the compositions of the disclosure are formulated in the form of tablets.

In some embodiments, the pharmaceutical composition of the disclosure comprises a therapeutically effective amount of a hemi-citrate salt of Compound 1 or solvate thereof and a pharmaceutically acceptable excipient. In certain embodiments, the pharmaceutical composition comprises an effective amount of the hemi-citrate salt of Compound 1. In certain embodiments, the pharmaceutical composition comprises a therapeutically effective amount of the hemi-citrate salt of Compound 1. In certain embodiments, the pharmaceutical composition comprises a prophylactically effective amount of the hemi-citrate salt of Compound 1.

In some embodiments, the pharmaceutical composition of the disclosure comprises Form IA of the hemi-citrate salt of Compound 1. In some embodiments, the pharmaceutical composition comprises Form IB of the hemi-citrate salt of Compound 1. In other embodiments, the pharmaceutical composition comprises a mixture of Form IA and Form IB of the hemi-citrate salt of Compound 1. In certain embodiments, Form IB of the Compound 1 hemi-citrate salt is present in the composition in a greater amount than Form IA.

This disclosure provides pharmaceutical compositions that contain a hemi-citrate salt of Compound 1 and one or more pharmaceutically acceptable excipients, or carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions of the disclosure may be administered in either single or multiple doses by any of the accepted modes of administration of agents having similar utilities, for example as described in those patents and patent applications incorporated by reference herein, including rectal, buccal, intranasal, and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

Oral administration is a preferred route for administration of compounds in accordance with the disclosure. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper, or other container. When the excipient serves as a diluent, it can be in the form of a solid, semi-solid, or liquid material (as described above), which acts as a vehicle, carrier, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to about 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the disclosure can be formulated so as to provide quick, sustained, or delayed release of the hemi-citrate salt of Compound 1 after administration to the patient. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, or ampoule). The compounds are generally administered in a pharmaceutically effective amount.

Preferably, for oral administration, each dosage unit (e.g., tablet) contains from about 5 mg to about 120 mg of the hemi-citrate salt of Compound 1. In some embodiments, each dosage unit (e.g., tablet) includes about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, or about 120 mg of the hemi-citrate salt of Compound 1.

In some embodiments, the hemi-citrate salt of Compound 1 is present in the oral dosage form (e.g., tablet) at a weight percent of from about 20% to about 40%. In some embodiments, the hemi-citrate salt of Compound 1 is present in the oral dosage form (e.g., tablet) at a weight percent of from about 25% to about 35%. In some embodiments, the hemi-citrate salt of Compound 1 is present in the oral dosage form (e.g., tablet) at a weight percent of from about 20% to about 25% (e.g., about 21%, about 22%, about 23%, about 24%, or about 25%). In some embodiments, the hemi-citrate salt of Compound 1 is present in the oral dosage form (e.g., tablet) at a weight percent of from about 25% to about 30% (e.g., about 25%, about 27%, about 28%, about 29%, or about 30%).

For preparing solid compositions such as tablets, the principal active ingredient is mixed with a pharmaceutical excipient to form a solid pre-formulation composition containing a homogeneous mixture of the hemi-citrate salt of Compound 1. When referring to these pre-formulation compositions as homogeneous, it is meant that the active ingredient is dispersed evenly throughout the composition so that the composition may be readily subdivided into equally effective unit dosage forms such as tablets, pills, and capsules.

The tablets or pills comprising compounds as disclosed herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Figure 26:
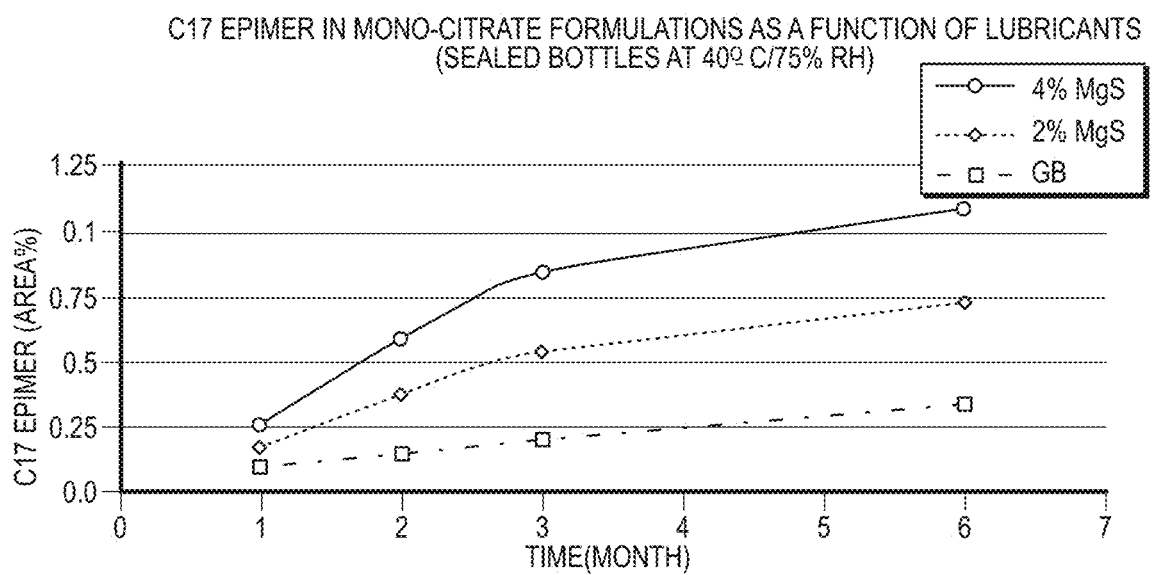
FIG. 26 is a graph showing the C17 epimer generation in the Compound 1 mono-citrate tablet formulations with different amounts of magnesium stearate as a function of time.

Salt forms of Compound 1, including for example the mono-citrate salt of Compound 1, may be sticky, and hence, may be less amenable to developing compositions for oral formulation. This can be a significant problem upon process scale-up, where the salt forms of Compound 1 may be prone to stick to metal surfaces. To overcome this problem, significant quantities of lubricant (e.g., magnesium stearate) are often required to develop the formulation. It has been discovered that the hemi-citrate salt of Compound 1 has substantially reduced stickiness compared to other salt forms of Compound 1, including the mono-citrate salt form. As a result, the amount of lubricant (e.g., magnesium stearate) in the composition can be reduced substantially. Importantly, magnesium stearate had been found to reduce the chemical stability of Compound 1, particularly when present in high amounts in the composition. Specifically, greater amounts of lubricant (e.g., magnesium stearate) in tablets comprising Compound 1 or a pharmaceutically acceptable salt thereof may increase the formation of the C17-epimer upon storage. For instance, as shown in FIG. 26, magnesium stearate appears to play a significant role in C17 epimer generation in the Compound 1 mono-citrate tablet. Therefore, reduced magnesium stearate amounts that are compatible with the hemi-citrate salt of Compound 1 result in less formation of undesirable impurities, such as the C-17 epimer.

Moreover, reduction in the levels of magnesium stearate result in reduced compression forces required to produce tablets. High compression forces often result in loss of tablet porosity, which in turn slows tablet disintegration and potentially dissolution.

In some embodiments, the disclosure provides pharmaceutical compositions comprising a hemi-citrate salt of Compound 1 and a lubricant, wherein the percentage of the lubricant in the pharmaceutical composition is less than about 4% by weight, such as less than about 3.75% by weight, less than about 3.5% by weight, or less than about 3.25% by weight. In some embodiments, the disclosure provides pharmaceutical compositions comprising a hemi-citrate salt of Compound 1 and a lubricant, wherein the percentage of the lubricant in the pharmaceutical composition is less than about 3% by weight, such as less than about 2.75% by weight, less than about 2.5% by weight, or less than about 2.25% by weight. In some embodiments, the disclosure provides pharmaceutical compositions comprising a hemi-citrate salt of Compound 1 and a lubricant, wherein the percentage of the lubricant in the pharmaceutical composition is less than about 2% by weight, such as less than about 1.75% by weight, less than about 1.5% by weight, or less than about 1.25% by weight. In some embodiments, the disclosure provides pharmaceutical compositions comprising a hemi-citrate salt of Compound 1 and a lubricant, wherein the percentage of the lubricant in the pharmaceutical composition is less than about 1.5% by weight. In some embodiments, the disclosure provides pharmaceutical compositions comprising a hemi-citrate salt of Compound 1 and a lubricant, wherein the percentage of the lubricant in the pharmaceutical composition is less than about 1% by weight. In some embodiments, the disclosure provides pharmaceutical compositions comprising a hemi-citrate salt of Compound 1 and a lubricant, wherein the percentage of the lubricant in the pharmaceutical composition is from about 2% by weight to about 4% by weight. In some embodiments, the disclosure provides pharmaceutical compositions comprising a hemi-citrate salt of Compound 1 and a lubricant, wherein the percentage of the lubricant in the pharmaceutical composition is from about 1.5% by weight to about 3% by weight. Examples of particular lubricants that can be used in accordance with the disclosure include, but are not limited to, magnesium stearate, sodium stearyl fumarate, stearic acid, talc, silica, and fats (e.g., vegetable stearin). In some embodiments, the lubricant in the pharmaceutical compositions disclosed herein is magnesium stearate.

In some embodiments, the disclosure provides pharmaceutical compositions comprising a hemi-citrate salt of Compound 1 and magnesium stearate, wherein the percentage of magnesium stearate in the pharmaceutical composition is less than about 4% by weight. In other embodiments, the disclosure provides pharmaceutical compositions comprising a hemi-citrate salt of Compound 1 and magnesium stearate, wherein the percentage of magnesium stearate in the pharmaceutical composition is less than about 3% by weight. In other embodiments, the disclosure provides pharmaceutical compositions comprising a hemi-citrate salt of Compound 1 and magnesium stearate, wherein the percentage of magnesium stearate in the pharmaceutical composition is less than about 2.5% by weight. In other embodiments, the disclosure provides pharmaceutical compositions comprising a hemi-citrate salt of Compound 1 and magnesium stearate, wherein the percentage of magnesium stearate in the pharmaceutical composition is less than about 2.2% by weight. In other embodiments, the disclosure provides pharmaceutical compositions comprising a hemi-citrate salt of Compound 1 and magnesium stearate, wherein the percentage of magnesium stearate in the pharmaceutical composition is less than about 2% by weight, such as less than about 1.75% by weight, less than about 1.5% by weight, or less than about 1.25% by weight. In other embodiments, the disclosure provides pharmaceutical compositions comprising a hemi-citrate salt of Compound 1 and magnesium stearate, wherein the percentage of magnesium stearate in the pharmaceutical composition is less than about 1% by weight. In some embodiments, the pharmaceutical compositions comprise about 0.5% to about 4% magnesium stearate by weight. In other embodiments, the disclosure provides pharmaceutical compositions comprising a hemi-citrate salt of Compound 1 and magnesium stearate, wherein the percentage of magnesium stearate in the pharmaceutical composition is less than about 1% by weight. In some embodiments, the pharmaceutical compositions comprise from about 0.5% to about 3% magnesium stearate by weight. In some embodiments, the pharmaceutical compositions comprise from about 0.5% to about 2% magnesium stearate by weight. In some embodiments, the pharmaceutical compositions comprise from about 0.5% to about 3% magnesium stearate by weight. In some embodiments, the pharmaceutical compositions comprise from about 1% to about 3% magnesium stearate by weight. In some embodiments, the pharmaceutical compositions comprise from about 1% to about 2% magnesium stearate by weight. In some embodiments, the pharmaceutical compositions comprise from about 1% to about 1.5% magnesium stearate by weight.

In some embodiments, the disclosure provides pharmaceutical compositions comprising a hemi-citrate salt of Compound 1 and magnesium stearate, wherein the composition comprises from about 20% to about 30% (e.g., about 20%, about 21%, about 22%, about 23%, about 24%, about 25%, about 26%, about 27%, about 28%, about 29%, or about 30%) by weight of the hemi-citrate salt of Compound 1 and from about 1% to about 3% magnesium stearate by weight. In some embodiments, the pharmaceutical compositions comprise from about 20% to about 30% (e.g., about 20%, about 21%, about 22%, about 23%, about 24%, about 25%, about 26%, about 27%, about 28%, about 29%, or about 30%) by weight of the hemi-citrate salt of Compound 1 and from about 1% to about 2% magnesium stearate by weight. In some embodiments, the pharmaceutical compositions comprise from about 20% to about 30% (e.g., about 20%, about 21%, about 22%, about 23%, about 24%, about 25%, about 26%, about 27%, about 28%, about 29%, or about 30%) by weight of the hemi-citrate salt of Compound 1 and from about 1% to about 1.5% magnesium stearate by weight.

In the aforementioned embodiments, the percentage by weight of lubricant (e.g., magnesium stearate) indicates the total amount of magnesium stearate in the pharmaceutical composition (e.g., tablet). In some embodiments, the lubricant (e.g., magnesium stearate) in the tablet can be apportioned between an intragranular and an extra-granular section. For instance, in some embodiments where the tablet comprises a total of about 2% by weight magnesium stearate, the intragranular section of the tablet comprises about 0.5% by weight of magnesium stearate, and the extra-granular section of the tablet comprises about 1.5% weight of magnesium stearate. In some embodiments where the tablet comprises a total of about 2% by weight magnesium stearate, the intragranular section of the tablet comprises about 1% by weight of magnesium stearate, and the extra-granular section of the tablet comprises about 1% weight of magnesium stearate. In certain embodiments, the intragranular section of the tablet comprises no more than 1% by weight of magnesium stearate (e.g., about 0.25%, about 0.5%, about 0.75%, or about 1% by weight magnesium stearate). In some embodiments, the intragranular section of the tablet comprises from about 0.5% to about 1% by weight magnesium stearate (e.g., about 0.5%, about 0.6%, about 0.7%, about 0.8%, about 0.9%, or about 1%).

In certain embodiments, tablets comprising the hemi-citrate salt of Compound 1 and quantities of magnesium stearate as set forth herein may comprise less than about 3% of the C17-epimer by weight based on the total weight of the hemi-citrate salt of Compound 1, following storage of the tablet for about 6 months at about 40° C. and about 75% relative humidity. In certain embodiments, tablets comprising the hemi-citrate salt of Compound 1 and quantities of magnesium stearate as set forth herein may comprise less than about 2% of the C17-epimer by weight based on the total weight of the hemi-citrate salt of Compound 1, following storage of the tablet for about 6 months at about 40° C. and about 75% relative humidity. In certain embodiments, tablets comprising the hemi-citrate salt of Compound 1 and quantities of magnesium stearate as set forth herein may comprise less than about 1% of the C17-epimer by weight based on the total weight of the hemi-citrate salt of Compound 1, following storage of the tablet for about 6 months at about 40° C. and about 75% relative humidity. In some embodiments, the tablets comprise less than about 0.75% of the C17-epimer by weight based on the total weight of the hemi-citrate salt of Compound 1, following storage of the tablet for about 6 months at about 40° C. and about 75% relative humidity. In other embodiments, the tablets comprise less than about 0.5% of the C17-epimer by weight based on the total weight of the hemi-citrate salt of Compound 1, following storage of the tablet for 6 months at about 40° C. and about 75% relative humidity. In other embodiments, the tablets comprise less than about 0.25% of the C17-epimer by weight based on the total weight of the hemi-citrate salt of Compound 1, following storage of the tablet for about 6 months at about 40° C. and about 75% relative humidity. In other embodiments, the tablets comprise from about 0.25% to about 1% of the C17-epimer by weight based on the total weight of the hemi-citrate salt of Compound 1, following storage of the tablet for about 6 months at about 40° C. and about 75% relative humidity. In other embodiments, the tablets comprise from about 0.5% to about 1% of the C17-epimer by weight based on the total weight of the hemi-citrate salt of Compound 1, following storage of the tablet for about 6 months at about 40° C. and about 75% relative humidity. In certain embodiments, the tablets are stored in the presence of a desiccant. In certain embodiments, the tablets are stored without a desiccant. The percent epimer present in a tablet formulation may vary based upon the strength of the dosage form, such that a lower strength dosage form may have a higher percent epimer present than a higher strength dosage form.

The pharmaceutical compositions (e.g., tablets) of the disclosure also can comprise one or more disintegrants. Suitable disintegrants may include, but are not limited to, crospovidone, croscarmellose sodium, low-substituted hydroxypropyl cellulose, sodium starch glycolate, and starch. In some embodiments, the disintegrant is crospovidone. In some embodiments, the disintegrant (e.g., crospovidone) is present in the pharmaceutical composition from about 1.5% to about 10% by weight. In some embodiments, the disintegrant (e.g., crospovidone) is present in the pharmaceutical composition from about 3% to about 8% by weight (e.g., about 3%, about 4%, about 5%, about 6%, about 7%, or about 8% by weight). In some embodiments, the pharmaceutical composition comprises an intragranular and an extra-granular portion and the disintegrant (e.g., crospovidone) is present in the intragranular and/or the extra-granular portion of the pharmaceutical composition in an amount from about 2% to about 4% by weight (e.g., about 2%, about 2.5%, about 3%, about 3.5%, or about 4% by weight).

It has been found that tablets comprising salt forms other than the hemi-citrate salt of Compound 1, such as the mono-citrate form, have prolonged rates of disintegration after ingestion, even when sufficient quantities of disintegrant are present, which can detrimentally affect dissolution and rate of absorption of Compound 1. Without intending to be bound by any theory, it is believed that the poor disintegration rates are a result of the stickiness and/or hygroscopicity of the compounds, properties that may hinder effective disintegration. The resultant requirement for higher amounts of lubricant (e.g., magnesium stearate) to counter the stickiness and/or hygroscopicity of the compounds also detrimentally affects disintegration times. On the other hand, the hemi-citrate salt of Compound 1 rapidly disintegrates from a tablet comprising one or more disintegrants (e.g., crospovidone).

In some embodiments, the disintegration time of a pharmaceutical composition (e.g., tablet) comprising a hemi-citrate salt of Compound 1 is less than about 3 minutes when the disintegration test is performed in accordance with the method described in United States Pharmacopeia (USP) chapter <701> without disk (see Example 12). In some embodiments, the disintegration time of a pharmaceutical composition (e.g., tablet) comprising a hemi-citrate salt of Compound 1 is less than about 2.5 minutes when the disintegration test is performed in accordance with the method described in USP chapter <701> without disk. In some embodiments, the disintegration time of a pharmaceutical composition (e.g., tablet) comprising a hemi-citrate salt of Compound 1 is less than about 2 minutes when the disintegration test is performed in accordance with the method described in USP chapter <701> without disk. In some embodiments, the disintegration time of a pharmaceutical composition (e.g., tablet) comprising a hemi-citrate salt of Compound 1 is less than about 1.5 minutes when the disintegration test is performed in accordance with the method described in USP chapter <701> without disk. In some embodiments, the disintegration time of a pharmaceutical composition (e.g., tablet) comprising a hemi-citrate salt of Compound 1 is from about 1.5 minutes to about 3 minutes when the disintegration test is performed in accordance with the method described in USP chapter <701> without disk. In some embodiments, the disintegration time of a pharmaceutical composition (e.g., tablet) comprising a hemi-citrate salt of Compound 1 is from about 2 minutes to about 3 minutes when the disintegration test is performed in accordance with the method described in USP chapter <701> without disk. In some embodiments, the disintegration time of a pharmaceutical composition (e.g., tablet) comprising a hemi-citrate salt of Compound 1 is from about 2 minutes to about 2.5 minutes when the disintegration test is performed in accordance with the method described in USP chapter <701> without disk. In all embodiments set forth herein, the disintegration test set forth in USP chapter <701> without disk refers to the USP chapter <701> as posted on Apr. 26, 2019, and having the targeted official date of May 1, 2020.

The tablets formed in accordance with the disclosure have tensile strengths that are amenable to scale-up. In some embodiments, the disclosure provides tablets comprising the hemi-citrate salt of Compound 1 and a lubricant (e.g., magnesium stearate), wherein the tensile strength of the tablet is at least about 1.7 megapascals (MPa). In some embodiments, the tablets have a tensile strength of from about 1.7 MPa to about 4.5 MPa. In some embodiments, the tablets have a tensile strength of from about 1.7 MPa to about 3.5 MPa. In some embodiments, the tablets have a tensile strength of from about 2.0 MPa to about 3.0 MPa.

In some embodiments, the tablets disclosed herein comprise about 10 mg, about 20 mg, or about 40 mg of the hemi-citrate salt of Compound 1, magnesium stearate, and crospovidone. It will be understood that the weight of the Compound 1 hemi-citrate salt in the tablet refers to the free base equivalent weight. In some embodiments, the composition (e.g., tablet) comprises a Compound 1 hemi-citrate salt, microcrystalline cellulose, lactose monohydrate, crospovidone, colloidal silicon dioxide, and magnesium stearate. In some embodiments, the tablets comprise the following components:

| No. | Component | % w/w | | |
|---|---|---|---|---|
| | | 10 mg Tablet[a] | 20 mg Tablet[b] | 40 mg Tablet[b] |
| | Tablet Core | | | |
| | Compound 1 hemi-citrate salt | 12.24 | 24.48 | 24.48 |
| | Microcrystalline Cellulose | 18.00 | 15.00 | 15.00 |
| | Lactose Monohydrate | 58.76 | 49.52 | 49.52 |
| | Crospovidone | 7.00 | 7.00 | 7.00 |
| | Colloidal Silicon Dioxide | 2.00 | 2.00 | 2.00 |
| | Magnesium Stearate | 2.00 | 2.00 | 2.00 |
| | Total | 100 | 100 | 100 |
| | Coated Tablet | | | |

[a]Equivalent to 10.0 mg Compound 1 free base per tablet.
[b]Equivalent to 20.0 mg Compound 1 free base per tablet.
[c]Equivalent to 40.0 mg Compound 1 free base per tablet.

V. Methods of Use

In one aspect, the present disclosure provides methods of treating a disease or condition in a subject in need thereof comprising administering to the subject a therapeutically effective amount of a hemi-citrate salt of Compound 1, or composition thereof, as disclosed herein.

In some embodiments, the hemi-citrate salt of Compound 1 used in the methods disclosed herein is substantially pure hemi-citrate salt of Compound 1 having the formula:

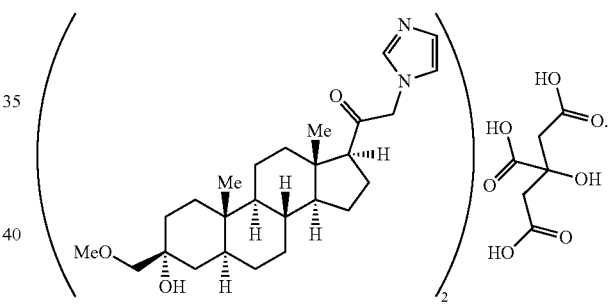

In some embodiments, the Compound 1 hemi-citrate salt used in the methods disclosed herein is substantially free of a mono-citrate salt of Compound 1. In some embodiments, the Compound 1 hemi-citrate salt contains less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, or less than about 0.5% by weight of a mono-citrate salt of Compound 1. In some embodiments, the Compound 1 hemi-citrate salt contains less than about 5% by weight of a mono-citrate salt of Compound 1. In some embodiments, the Compound 1 hemi-citrate salt contains less than about 4% by weight of a mono-citrate salt of Compound 1. In some embodiments, the Compound 1 hemi-citrate salt contains less than about 3% by weight of a mono-citrate salt of Compound 1. In some embodiments, the Compound 1 hemi-citrate salt contains less than about 2% by weight of a mono-citrate salt of Compound 1. In some embodiments, the Compound 1 hemi-citrate salt contains less than about 1% by weight of a mono-citrate salt of Compound 1. In some embodiments, the Compound 1 hemi-citrate salt contains less than about 0.5% by weight of a mono-citrate salt of Compound 1. In some embodiments, the Compound 1 hemi-citrate salt contains no more than about 1%, no more than about 0.9%, no more than about 0.8%, no more than about 0.7%, no more than about 0.6%, no more than about 0.5%, no more than about 0.4%, no more than about 0.3%, no more than about 0.2% by weight, or no more than about 0.1% by weight of a mono-citrate salt of Compound 1. In some embodiments, the Compound 1 hemi-citrate salt contains no more than about 0.2% by weight of a mono-citrate salt of Compound 1. In some embodiments, the mono-citrate salt of Compound 1 is a crystalline form. In some embodiments, the hemi-citrate salt is substantially free of crystalline Form A of the mono-citrate salt of Compound 1.

In some embodiments of the present disclosure, the Compound 1 hemi-citrate salt is a hydrate, such as a channel hydrate. In some embodiments, the Compound 1 hemi-citrate salt has a water content from about 0% to about 5% by weight, e.g., about 0%, about 0.25%, about 0.5%, about 0.75%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, or about 5% by weight. In some embodiments, the Compound 1 hemi-citrate salt has a water content of about 5% by weight. In some embodiments of the present disclosure, the hemi-citrate salt of Compound 1 is a sesquihydrate.

In some embodiments of the present disclosure, the Compound 1 hemi-citrate salt has a water content between about 2% and about 4% by weight at room temperature and relative humidity of about 20-90%, such as a water content of about 2%, about 2.25%, about 2.5%, about 2.75%, about 3%, about 3.25%, about 3.5%, about 3.75% or about 4% by weight. In some embodiments of the present disclosure, the Compound 1 hemi-citrate salt has a water content between about 3% and about 5% at about 40° C. and relative humidity of about 20-90%, such as a water content of about 3%, about 3.25%, about 3.5%, about 3.75%, about 4%, about 4.25%, about 4.5%, or about 5% by weight.

In some embodiments of the present disclosure, the hemi-citrate salt of Compound 1 is a crystalline form. In some embodiments, the hemi-citrate salt of Compound 1 is crystalline Form I, as disclosed herein. In some embodiments, the hemi-citrate salt of Compound 1 is Form IA, and in some embodiments, the hemi-citrate salt of Compound 1 is Form IB.

In some embodiments, the diseases or conditions that may be treated by the methods disclosed herein include, but are not limited to, depression (including treatment resistant depression and post-partum depression), major depressive disorder, bipolar disorder, epilepsy, and anxiety. In some embodiments, the disease or condition is depression. In some embodiments, the disease or condition is treatment resistant depression. In some embodiments, the disease or condition is post-partum depression. In some embodiments, the disease or condition is major depressive disorder. In some embodiments, the disease or condition is bipolar disorder. In some embodiments, the disease or condition is epilepsy. In some embodiments, the disease or condition is anxiety.

Methods of treating such diseases with Compound 1 and salts thereof are disclosed in, for example, US2020/0323823 and WO2020/180955, each of which is incorporated herein by reference in its entirety.

VI. Articles of Manufacture

Articles of manufacture are also provided herein, wherein the article of manufacture comprises a substantially pure hemi-citrate salt of Compound 1 as described herein in a suitable packaging. In some embodiments, the hemi-citrate salt of Compound 1 is formulated for oral delivery. In some embodiments, the hemi-citrate salt of Compound 1 is formulated as a tablet. In some embodiments of the foregoing, the article of manufacture further comprises a desiccant. In some embodiments, the packaging is a desiccated bottle. In some embodiments, the packaging is desiccated blisters.

The present disclosure further provides kits for carrying out the methods disclosed herein. The kits may comprise a substantially pure hemi-citrate salt of Compound 1 as described herein in a suitable packaging. In some embodiments, the kits further comprise a desiccant. In some embodiments, the packaging is a desiccated bottle. In some embodiments, the packaging is desiccated blisters. In some embodiments, the kit further includes a label and/or instructions for use of the substantially pure hemi-citrate salt of Compound 1 as described herein in the treatment of a disease or disorder described herein. In some embodiments, the kits may comprise a unit dosage form of the compound.

EXAMPLES

The present disclosure is further illustrated by reference to the following Examples. However, it is noted that these Examples, like the embodiments described above, are illustrative and are not to be construed as restricting the scope of the disclosure in any way.

"EtOAc" means ethyl acetate. "(m)DSC" means (modulated) differential scanning calorimetry. "ACN" means acetonitrile. "AR" means analytically pure. "DCM" means dichloromethane. "DMF" means dimethyl formamide "DMSO" means dimethylsulfoxide. "DI" means distilled. "DSC" means differential scanning calorimetry. "DVS" means dynamic vapor sorption. "e.q." means equivalents. "EtOH" means ethyl alcohol. "FaSSIF" means fasted state simulated intestinal fluids. "FeSSIF" means fed state simulated intestinal fluids. "1H-NMR" means proton nuclear magnetic resonance. "IPA" means isopropanol. "IPAC" means isopropyl acetate. "IPE" means diisopropyl ether. "LC" means low crystallinity. "MEK" means methyl ethyl ketone. "MeOH" means methyl alcohol. "MIBK" means methyl isobutyl ketone. "MTBE" means Methyl Tert-Butyl ether. "NMR" means nuclear magnetic resonance. "PLM" means polarized light microscope. "RH" means relative humidity. "RRT" means relative retention time. "RT" means Room temperature. "RT(min)" means Retention time. "SGF" means simulated gastric fluids. "TGA" means Thermal gravimetric analysis. "THF" means Tetrahydrofuran. "UPLC" means ultra performance liquid chromatography. "XRPD" means X-ray Powder Diffractometer or X-ray Powder Diffraction.

In some instances, the ratio of Compound 1 to citric acid in the Compound 1 hemi-citrate salt described herein (or a crystalline form of the hemi-citrate salt) was determined by ion chromatography (IC) using the following method: 25 μL of 10.0 μg/mL sample or standard were injected into a Dionex IonPac AG18 column with a flow rate of 1.0 mL/min and detected by a Thermo ICS-2100 Conductivity detector. ASRS-4 mm suppressor was set at 38 mA and the column temperature was 30° C. The chromatographic elution was 15 mM KOH with a total run time of 20 minutes.

XRPD was performed with Panalytical X'Pert Powder XRPD on a Si zero-background plate. Analysis was performed with X'Pert HighScore and graphics were produced with XPert DataViewer. XRPD parameters for data collection were as follows:

| Parameters, for Reflection Mode | |
| --- | --- |
| X-Ray wavelength | Cu. ka. Kα1 (Å): 1.540598. Kα2 (Å): 1.544426 Kα2/Kα1 intensity ratio: 0.50 |
| X-Ray tube setting | 45 kV, 40 mA |
| Divergence slit | Automatic |
| Scan mode | Continous |
| Scan range (°2θ) | 39°-40° |
| Step size (°2θ) | 0.0131 |
| Scan speed (°/s) | 0.16 |
| Experiment time | ~4 min |

Single crystal X-ray analysis was performed as follows. Select crystals were immersed in MiTeGen LV5 oil-based cryoprotectant and mounted on a mylar MiTeGen cryoloop in a random orientation, then placed in an Oxford Cryostream 800 liquid nitrogen stream at 173 K. The X-ray intensity data were measured on a Bruker D8 VENTURE (IμS microfocus X-ray source, Cu Kα, λ=1.54178 Å, PHOTON CMOS detector) diffractometer. Collection strategy was optimized by the Bruker ApexIII software and the frames were integrated with the Bruker SAINT software package. Data were corrected for absorption effects using the Multi-Scan method (SADABS). The structure refinement and solution was obtained using the SHELX software suite, with supplemental data analysis performed using the PLATON software suite. Graphics were generated in the Mercury software.

Polarized light microscopy (PLM) pictures were captured on a Nikon DS-Fi2 upright microscope at room temperature.

TGA data was collected using a TA Discovery 550 from TA Instruments. TGA was calibrated using nickel reference standard. DSC was performed using a TA Q2000 DSC from TA Instruments. DSC was calibrated with indium reference standard. Data analysis was performed in the TA Universal Analysis software. Parameters used for data collection were as follows:

| Parameters | TGA | DSC |
| --- | --- | --- |
| Method | Ramp | Ramp |
| Sample pan | Platinum, open | Aluminum, open pan |
| Hearing rate | 10° C./min | 25° C.-desired temperature |
| Procedure | RT-300° C. | 10° C./min |
| Purge gas | $N_2$ | $N_2$ |

DVS was measured via a SMS (Surface Measurement System) DVS Intrinsic. Parameters for DVS data collection were as follows:

| Parameters | Values |
| --- | --- |
| Temperature | 25° C. |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 40% RH-95% RH-0% RH-95% RH |
| RH step size | 10% (40%; RH-95% RH-0% RH-95% RH) |

$^1$H-NMR were collected on a Bruker 500 MHz magnet. As is known to those skilled in the art, the relative ppm shift and integration values for $^1$H-NMR resonances may vary depending on various sample factors, including, for example, water content in the $d_6$-DMSO, ion concentration in the sample, etc. Thus, the $^1$H-NMR values reported in the following examples should not be considered characteristic for the salt and/or crystalline form.

UPLC data were collected by injecting a 0.5 μL of sample or standard into a Waters Acquity UPLC Shield RP18 column with a flow rate of 0.8 mL/min by an Agilent 1290 UPLC (detection wavelength: 210 nm). The column was equilibrated with mobile phase A which consisted of 0.1% $H_3PO_4$ in water. Mobile phase B was acetonitrile (ACN). The chromatographic elution was programed as follows with an additional minute after for re-equilibration and a total run time of 6 minutes:

| Time (min) | A (%) | B (%) |
| --- | --- | --- |
| 0 | 90 | 10 |
| 4 | 10 | 90 |
| 5 | 10 | 90 |

The crystalline salts described herein were characterized by polarized light microscopy. In some embodiments, the crystalline salts described herein exhibit birefringence, which indicates crystallinity.

Example 1: Hemi-Citrate Salts of Compound 1

Preparation

Hemi-citrate salts of Compound 1 may be prepared from Compound 1 using the following exemplary methods.

Compound 1 Hemi-Citrate Salt (Form I):

A solution of Compound 1 mono-citrate salt (650 g) in methanol (1.95 L) was prepared at room temperature. Complete dissolution took about 5 minutes using a stir bar in a 3 L conical flask to give a pale yellow solution. Water (7.8 L) was added to a 12 L round bottom flask equipped with mechanical agitator, an addition funnel, and a thermocouple. To the stirring aqueous solution, the Compound 1 mono-citrate salt methanol solution was added via addition funnel over about 30 minutes, maintaining the temperature at 20-25° C. The hemi-citrate salt began to precipitate almost immediately upon commencement of addition of the methanol solution. The suspension was aged for about 30 minutes at 20-25° C. The slurry was then filtered through a 2 L Buchner funnel with a medium porosity frit. The collected solid material was dried on the filter for 24 hours. The yield was about 70%.

The resulting solid was identified as Compound 1 hemi-citrate salt Form I. The ratio of Compound 1 to citric acid was 2:1 as determined by potentiometric titration. XPRD patterns for the high humidity form (Form IA) and the low humidity form (Form IB) are shown in FIG. 1 and FIG. 2, respectively; the DSC and TGA are shown in FIG. 3; and the DVS is shown in FIG. 4.

Compound 1 hemi-citrate salt Form I was analyzed by $^1$H-NMR in deuterated DMSO resulting in the following chemical shifts: $^1$H NMR (500 MHz, DMSO) δ 7.75 (s, 1H), 7.11 (s, 1H), 7.00 (s, 1H), 5.01 (dd, J=68.5, 18.5 Hz, 2H), 3.25 (s, 3H), 3.05 (s, 2H), 2.81-2.55 (m, 3H), 2.51 ($d_6$-DMSO), 2.06 (dd, J=20.6, 10.9 Hz, 2H), 1.76-0.84 (m, 22H), 0.79-0.65 (m, 4H), 0.58 (s, 3H).

XRPD, TGA, DSC, and DVS Analysis of Compound 1 Hemi-Citrate Salt Form I

Figure 5:
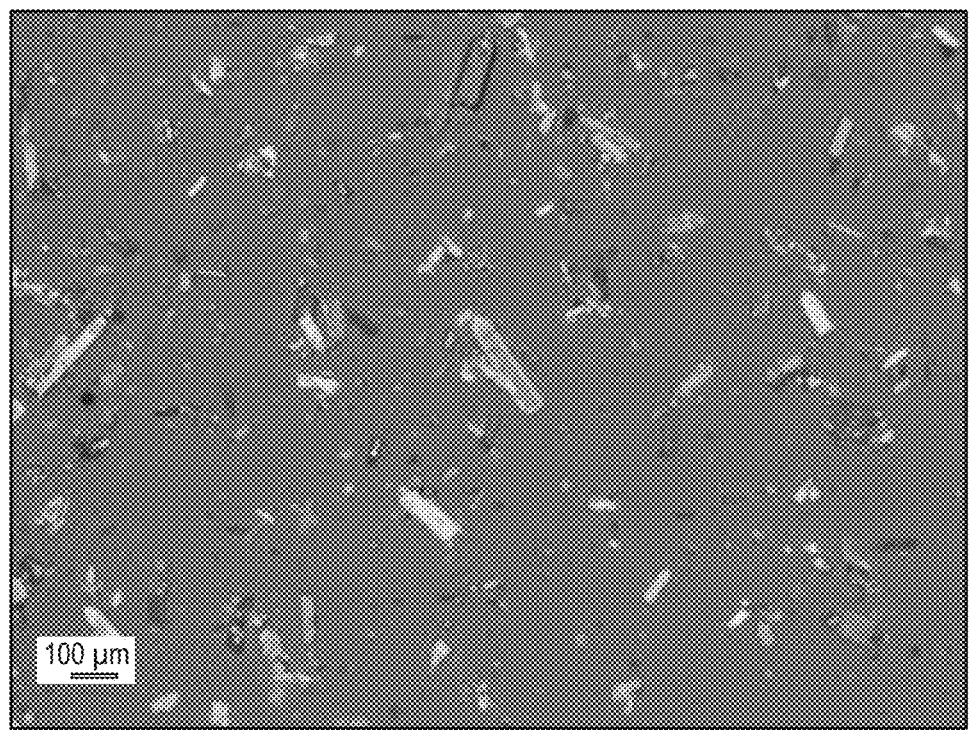
FIG. 5 shows a polarized light microscopy (PLM) image of sesquihydrates of the Compound 1 hemi-citrate salt Form I (Form IA).
Figure 6:
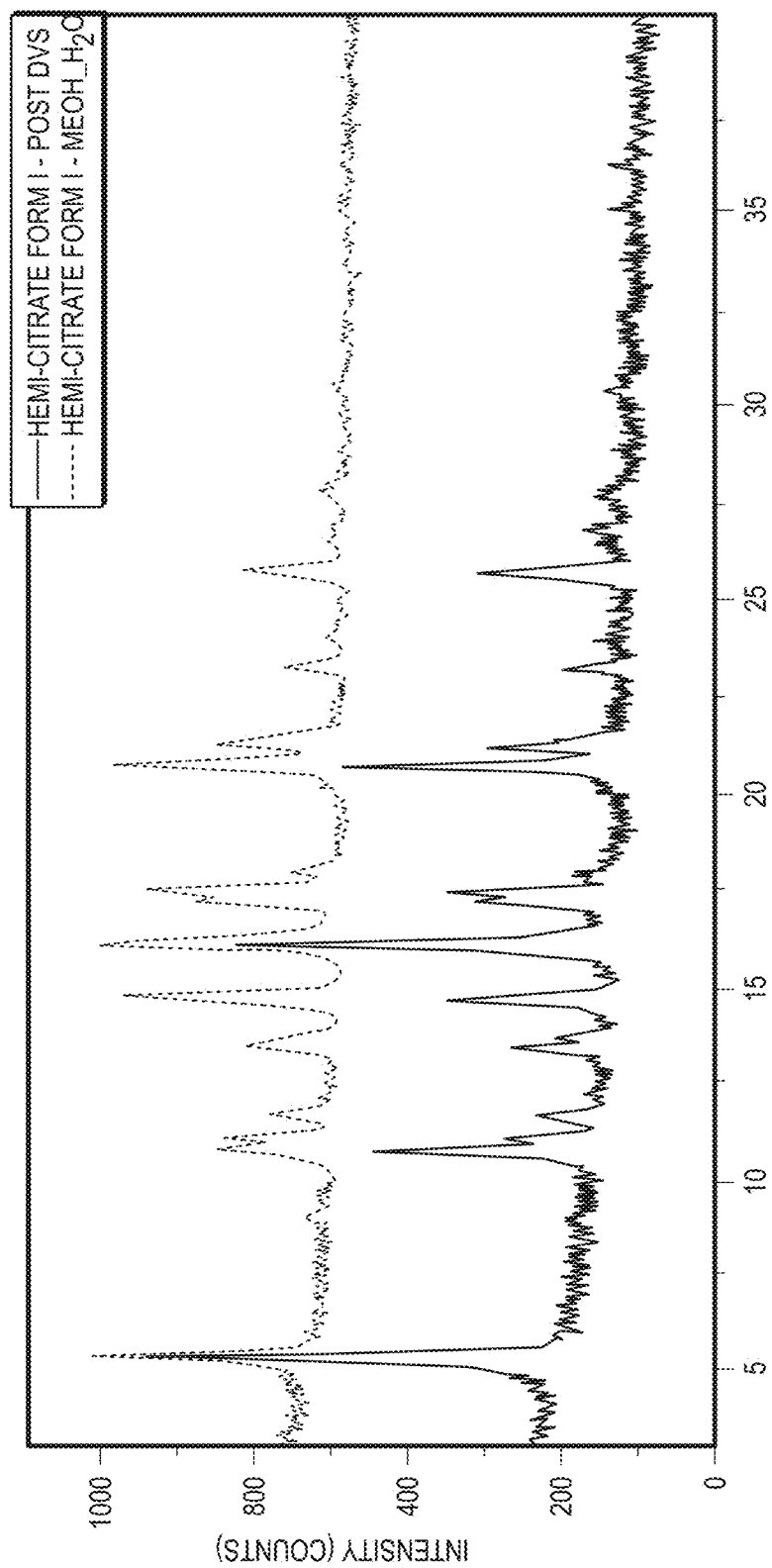
FIG. 6 shows XRPD patterns of the Compound 1 hemi-citrate salt Form I, showing the bulk product before testing (lower pattern, MeOH_$H_2O$) and post-DVS at room temperature (upper pattern).
Figure 7:
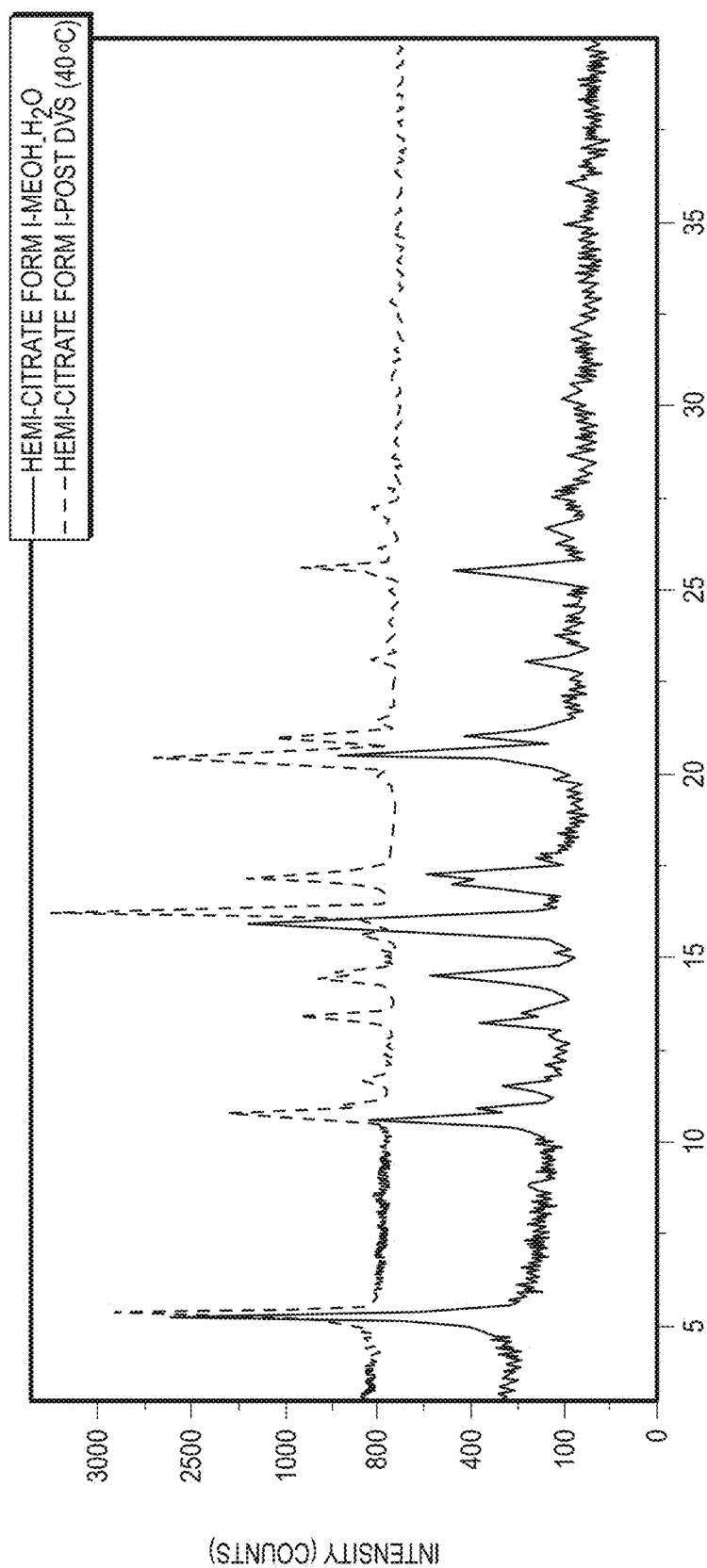
FIG. 7 shows XRPD patterns of the Compound 1 hemi-citrate salt Form I, showing the bulk product before testing (lower pattern, MeOH_$H_2O$) and post-DVS at 40° C. (upper pattern).

As shown in FIG. 5, Compound 1 hemi-citrate salt Form I has thin plates morphology, prone to stacking. The TGA of Form I (FIG. 3) indicates a weight loss of 4.4% between room temperature and approximately 100° C., suggesting a sesquihydrate hemi-citrate salt (i.e., Form IA). The DSC shows a desolvation endotherm with an onset temperature of 26.0° C. and a peak at 65.2° C. A second endotherm (having an onset at 121.5° C.) associated with melting of the dehydrated phase (ΔH: 15.20 J/g) was followed by a rapid decomposition as temperature continued to increase (FIG. 3). Because of the low onset of dehydration, the DVS was measured at both room temperature and at 40° C. to predict the stability of the crystalline phase at 40° C. At room temperature, the sample showed a water uptake of 1.2% between 20% and 80% RH, indicating that the sample is slightly hygroscopic. A 1.5% weight loss was observed between 95% and 20% RH, and a 2.9% weight loss was observed between 20% and 0% RH, for a total loss of 4.3% across the entire cycle. This loss appears to be fully reversible as relative humidity increases. The 40° C. temperature DVS displayed a water absorption of 1.8% from 20% to 80% RH, while 2.2% water was lost between 95% and 20% RH and 3.2% was lost from 20% to 0% RH, for a total loss of 5.4%. This loss was fully reversible. This indicates that Compound 1 hemi-citrate salt Form I is slightly hygroscopic, and the water in the crystalline lattice is more loosely bound than the water in Compound 1 mono-citrate salt lattice. After measuring the hygroscopicity by DVS, an XRPD pattern was collected for comparison to the original material and found to correspond well to the pattern of the room temperature sample post-DVS temperature cycle (FIG. 6). The DVS cycle measured at 40° C. displayed some minor changes in the XRPD peaks between 2θ values 14° and 18° (FIG. 7).

Single Crystal X-Ray Structure of Compound 1 Hemi-Citrate Salt Form I

Single crystals of Compound 1 hemi-citrate salt Form I suitable for X-ray diffraction were selected from samples produced by slow diffusion of water into a saturated solution in methanol.

Figure 8:
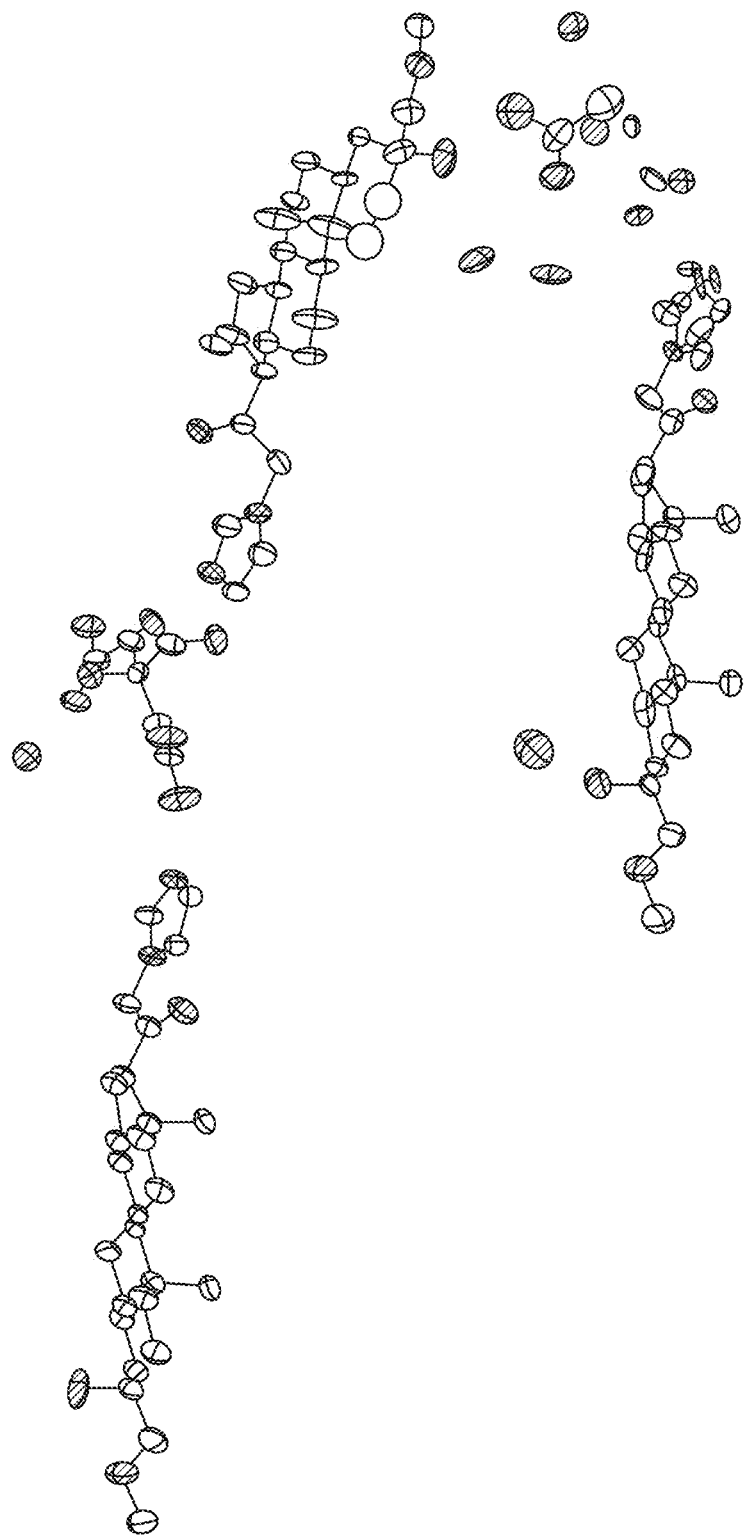
FIG. 8 provides the asymmetric unit cell of the Compound 1 hemi-citrate salt Form I from the single-crystal X-ray diffraction (SCXRD) solution. Thermal ellipsoids are shown at 50% confidence interval. Hydrogen atoms have been omitted for clarity.
Figure 9:
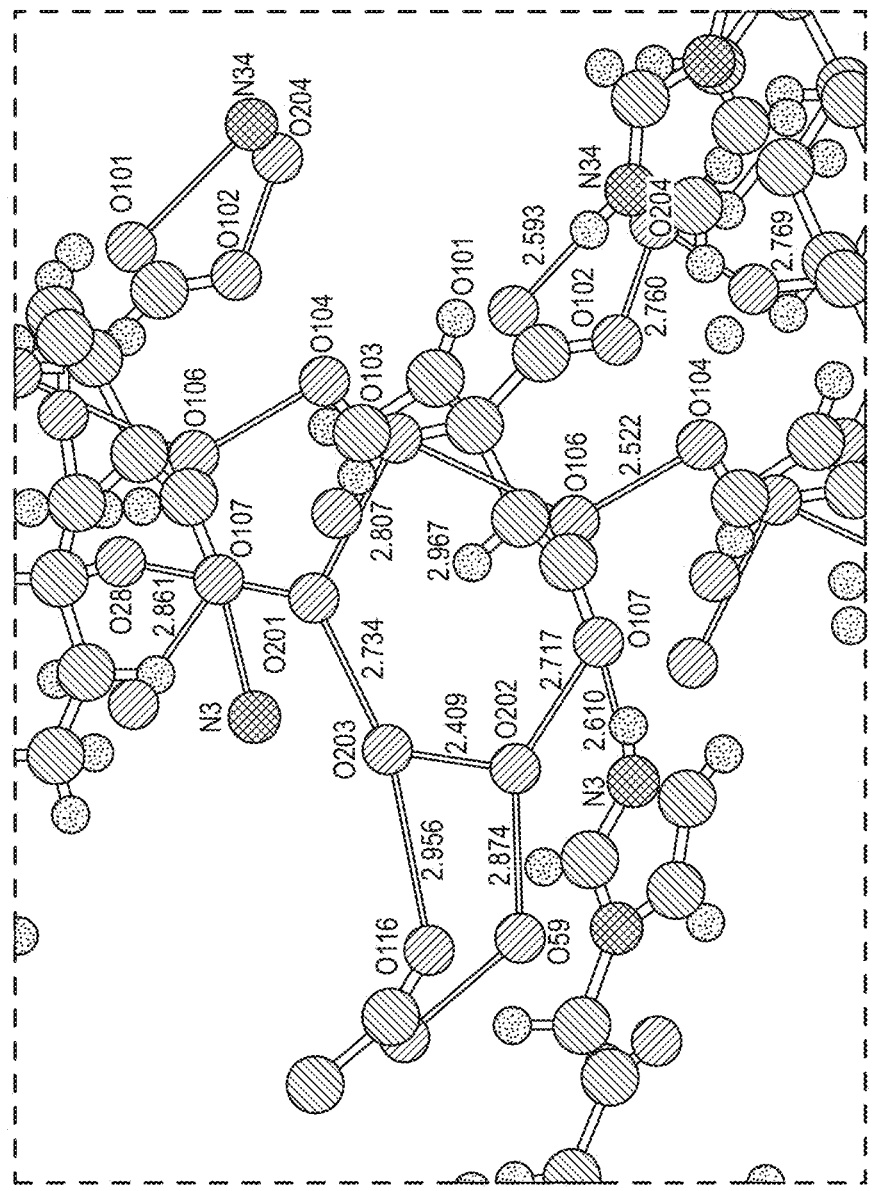
FIG. 9 shows the solvent-anion interactions in the Compound 1 hemi-citrate salt Form I and the donor-acceptor distances in hydrogen bonding interactions.

The single-crystal structure of Compound 1 hemi-citrate salt Form IA was collected at −100° C. for structural quality and to minimize the loss of solvent (FIG. 8 and FIG. 9). Compound 1 hemi-citrate salt Form IA crystallized in the C2 monoclinic space group (see Table 3). The additional water within the unit cell reduces the opportunity for API-citrate hydrogen bonding to form, diminishing the influence of those interactions in the structure. The hydrogen bonding network is difficult to completely evaluate, as one of the two citrates exists on a center of symmetry, while itself asymmetrical, resulting in a form of disorder that could not be readily resolved. This is further complicated by the possibility of unresolved water molecules. Some of the oxygen atoms in that region are easily differentiated between being a part of the disordered citrate and the solvent. While the API-citrate interactions are significantly less numerous, they are also much stronger, as measured by the interatomic distances, inferring contacts much more likely to be ionic in nature rather than electrostatic or Van der Waals interactions.

TABLE 3

Crystallographic Details of Compound 1 hemi-citrate salt Form I.

| | | |
|---|---|---|
| Empirical formula | C174H251N12O45 | |
| Formula weight | 3248.85 | |
| Temperature | 173 (2) K | |
| Wavelength | 1.54178 Å | |
| Crystal syatem | Monoclinic | |
| Space group | C2 | |
| Unit cell dimensions | a = 34.74 (2) Å | α = 90°. |
| | b = 8.3419 (19) Å | β = 108.45 (3)°. |
| | c = 31.107 (18) Å | γ = 90°. |
| Volume | 8717 (8) Å$^3$ | |
| Z | 2 | |
| Density (calculated) | 1.237 Mgm$^3$ | |
| Absorption coefficient | 0.331 mm$^{-1}$ | |
| F (000) | 3494 | |
| Crystal size | 0.697 × 0.380 × 0.064 mm$^2$ | |
| Theta range for data collection | 2.681 to 68.780°. | |
| Index ranges | −42 <= h <= 41, −10 <= k <= 9, −38 <= l <= 38 | |
| Reflections collected | 157837 | |
| Independent reflections | 15782 [R(mt) = 0.0770] | |
| Completeness to theta = 67.679° | 99.9% | |
| Absorption correction | Semi-empirical from equivalents | |
| Max. and min. transmission | 0.7531 and 0.6472 | |
| Refinement mehod | Full-matrix least-squares on F$^2$ | |
| Data/restraints/parameters | 15782/1/1062 | |
| Goodness-of-fit on F$^2$ | 2.507 | |
| Final R indices [I > 2 sigma (I)] | R1 = 0,1282, wR2 = 0.3404 | |
| R indices (all data) | R1 = 0.1473, wR2 = 0.3562 | |
| Absolute stucture parameter | 0.18 (9) | |
| Extinction coefficient | n/a | |
| Lasgest diff. paek and hole | 2.802 and −0.701 e.Å$^{-3}$ | |

Example 2: Characterization of Compound 1 Hemi-Citrate Salt Sesquihydrate Form IA by X-Ray Crystallography Several slurry samples (containing solvents such as acetone, water, THF, 2MeTHF, etc.) were submitted for single-crystal analysis. Cracks were observed in the rod/long plate like crystals after storage at room temperature for a few days, and growth of small crystalline particles on surfaces of the cracked crystals was also observed. Recrystallization by heating the slurry samples followed by naturally cooling to room temperature resulted in large single crystals with good X-ray diffraction quality. Data collection was carried out at 223K and 173K, with the crystals cooled using a cryostream low temperature device to reduce crystal decay. Datasets were collected on several freshly prepared crystals, which consistently gave the same unit cell parameters, but citric acid was not resolved in the crystal structure from these datasets. A side product from screening crystals was solving the crystal structure of a Compound 1 neat form, isolated from aqueous acetone.

The crystal structure of a Compound hemi-citrate salt sesquihydrate (i.e., Form IA) was solved from block-like crystals grown from aqueous methanol. The structure was first solved and partially refined in Space Group C2; however, due to extra difficulties in resolving highly complex disorders of citric acid, the structure was then solved and refined in Space Group P1.

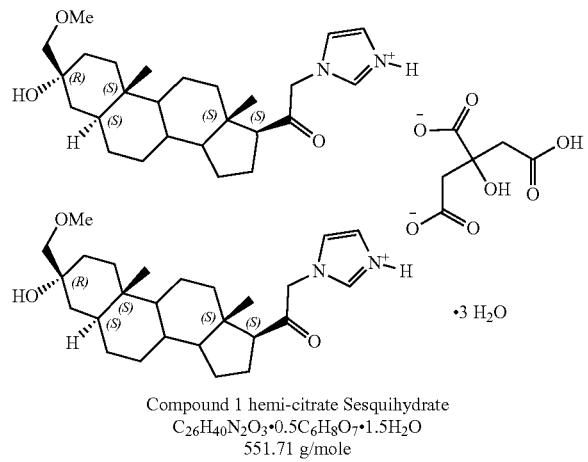

Compound 1 hemi-citrate Sesquihydrate
$C_{26}H_{40}N_2O_3 \cdot 0.5C_6H_8O_7 \cdot 1.5H_2O$
551.71 g/mole

Example 3: XRPD Analysis of the Hemi-Citrate Salt of Compound 1 at Various Relative Humidity Levels XRPD data was collected for Compound 1 hemi-citrate salt Form I at 90% RH, 80% RH, 30% RH, 20% RH, 10% RH, and 5% RH (Table 4).

The patterns show that the system remains unchanged from 90% to 30% RH, but show changes from 30% to 20% that persist to 5% RH (FIG. 10). These results are indicative of a change of the channel hydrate form Form IA of the hemi-citrate salt of Compound 1 at 90% to 30% RH to the channel hydrate form Form IB of the hemi-citrate salt of Compound 1 at an RH of less than 30%. For comparison, FIG. 10 also shows XRPD patterns of the Compound 1 mono-citrate salt anhydrate ("Form IV"), Compound 1 mono-citrate salt ("Form A; air dried"), Compound 1 hemi-citrate salt recrystallized from methanol and water ("Form I; MeOH/$H_2O$"), and the freebase of Compound 1.

The observed shift is similar to XRPD shifts observed in the post-DVS data provided in FIG. 6 and FIG. 7.

Example 4: Comparison of XRPD Patterns from Compound 1 Hemi-Citrate Salt Form IA and Compound 1 Mono-Citrate Salt (Form A)

Figure 11:
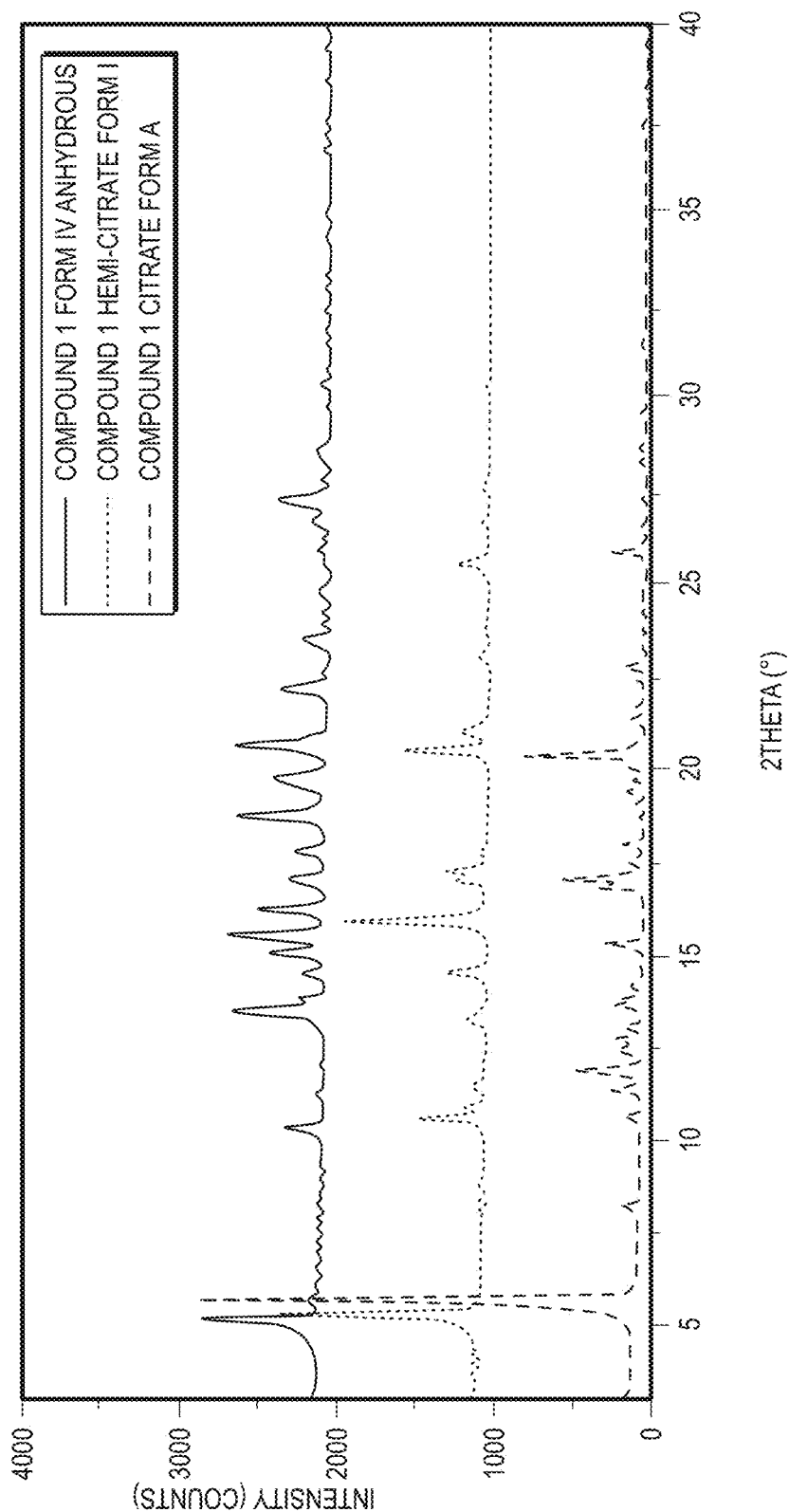
FIG. 11 shows a comparison of XRPD patterns for the Compound 1 mono-citrate salt (Form A) (bottom), the Compound 1 hemi-citrate salt (Form I) (middle), and the Compound 1 mono-citrate salt anhydrate (Form IV) (top).

The XRPD pattern of crystalline Compound 1 hemi-citrate salt Form IA is shown in FIG. 11 (middle pattern), stacked with those of Compound 1 mono-citrate salt (Form A) (bottom pattern) and Compound 1 mono-citrate salt anhydrate ("Form IV") (top pattern). Comparing each XRPD pattern shows that Compound 1 hemi-citrate salt Form IA has a distinct and unique pattern that is readily differentiated from the Compound 1 mono-citrate salt (Form A) and from Compound 1 mono-citrate salt anhydrate.

Example 5: Comparison of H-Bonding Interactions in Compound 1 Hemi-Citrate Salt Form IA and Compound 1 Mono-Citrate Salt (Form A)

Compound 1 hemi-citrate salt Form IA and Compound 1 mono-citrate salt (Form A) have conformations that depend heavily upon hydrogen bonding interactions. The appropriate hydrogen bonding interactions are listed in Table 5 (for Compound 1 mono-citrate salt Form A) and Table 6 (for Compound 1 hemi-citrate salt Form IA). Compound 1 mono-citrate salt (Form A) displays a very distinct set of intermolecular interactions, isolating two water molecules within a network of citrates, which then form hydrogen bonding interactions with API molecules in one direction while forming direct interactions between citrate anions in the other. The API functions as a bridging group between these citrate-water assemblies, resulting in a two-dimensional pseudo-polymeric sheet formation. In contrast, the hydrogen bonding network in Compound 1 hemi-citrate salt Form IA is predominantly a set of interactions between citrate anions and water molecules, but the citrate anions themselves form a pseudo-polymeric chain in one direction. Unlike in Compound 1 mono-citrate Form A, the water molecules in Compound 1 hemi-citrate Form IA freely interact with API molecules. In addition, Compound 1 mono-citrate Form A displays a single set of interactions between one citrate and an adjoining API molecule that can be close enough to be considered an ionic interaction, while Compound 1 hemi-citrate Form IA displays two for each citrate (3 API to 1.5 citrate anions within the asymmetric unit cell). This accounts for the hemi-citrate nature. The water interactions are significantly less uniform, and the presence of water-API hydrogen bonding removes an opportunity for additional citrate-API interactions. However, it appears that one of the citrate anions in Compound 1 hemi-citrate Form IA is located in a special position, but it does not match the symmetry of that position, resulting in apparent disorder. This creates a degree of uncertainty in the region, as it is rich in oxygen atoms that may be attributed to orientations of the citrate, or to water molecules solvating the crystalline matrix.

Figure 12:
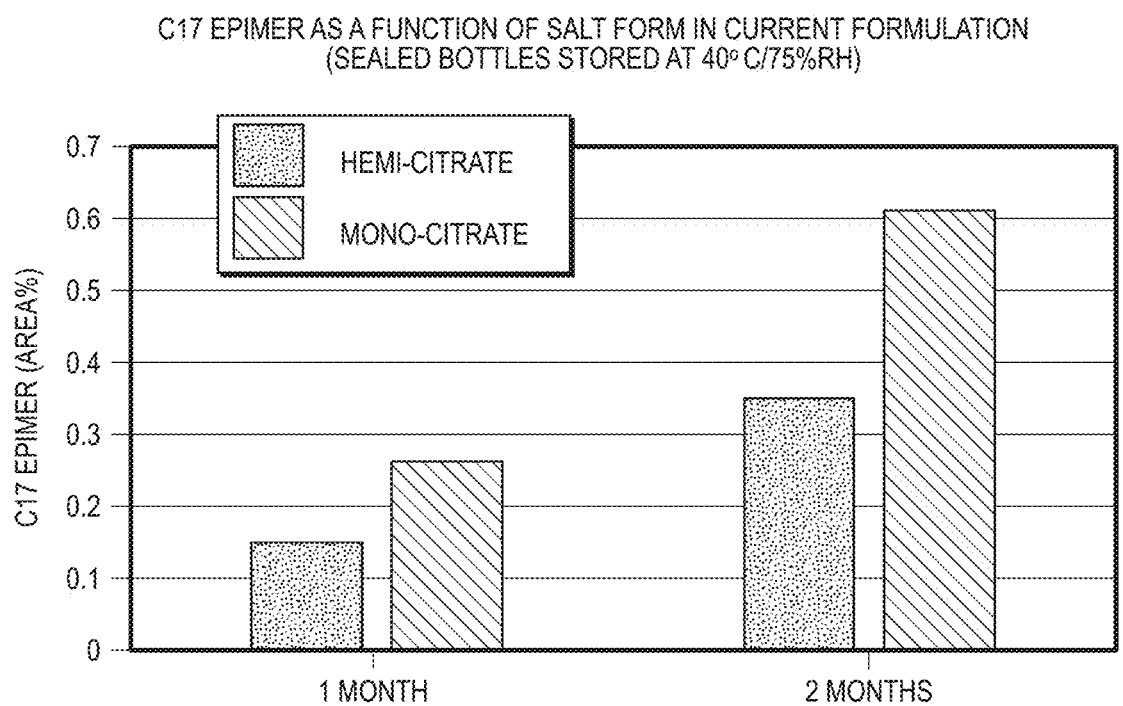
FIG. 12 is a graph comparing the amount of the C17 epimer, a degradation product of Compound 1, over time for a tablet formulation containing Compound 1 hemi-citrate salt (Form I; left column in both "1 month" and "2 months") or Compound 1 mono-citrate salt (Form A; right column in both "1 month" and "2 months") in sealed bottles stored at 40° C./75% RH).

Example 6: Comparison of Compound 1 Hemi-Citrate Salt Form I and Compound 1 Mono-Citrate Salt (Form A) Stability As shown in FIG. 12, when formulated as a tablet dosage form using the same formulation ingredients and manufacturing process, the hemi-citrate salt of Compound 1 stored in a sealed bottle for 1 or 2 months has been observed to generate less degradation product (i.e., the C17-epimer) than the mono-citrate salt of Compound 1, and thus, is more chemically stable.

Figure 13:
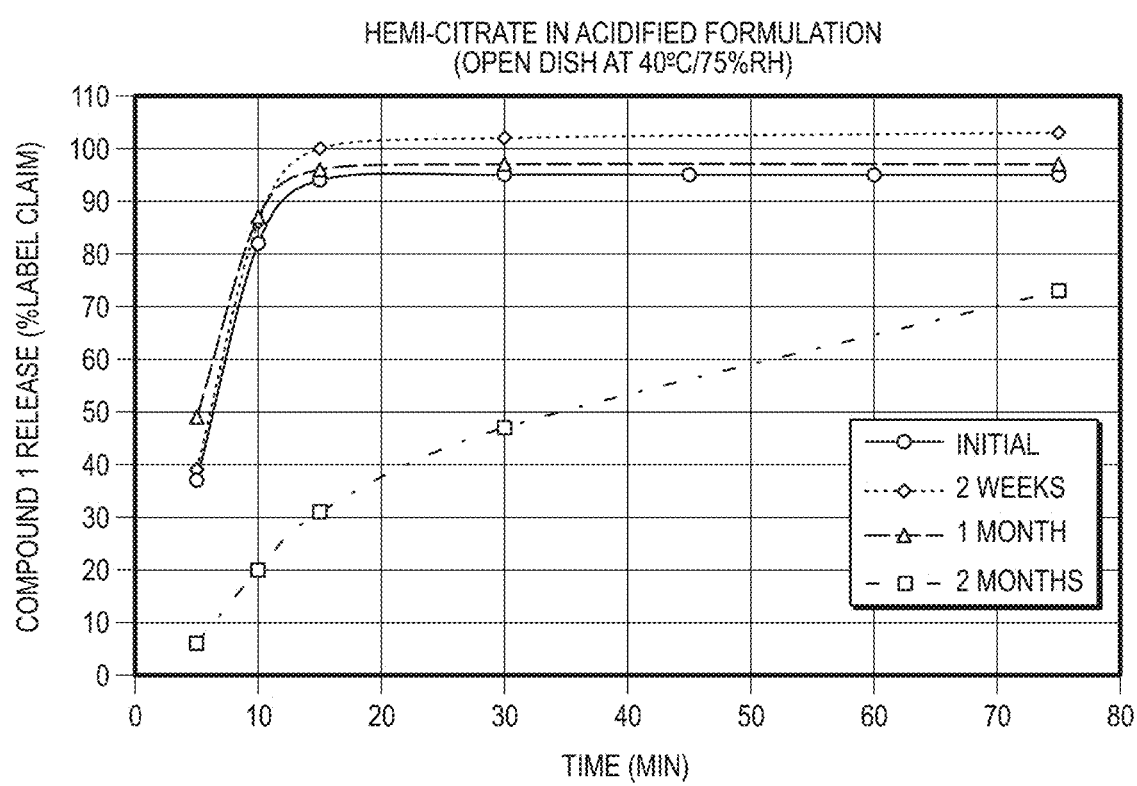
FIG. 13 is a graph showing percent release of Compound 1 over time for an acidified tablet formulation containing Compound 1 hemi-citrate salt Form I. Tablets were used initially or maintained at 40° C./75% RH for 2 weeks, 1 month, or 2 months.
Figure 14:
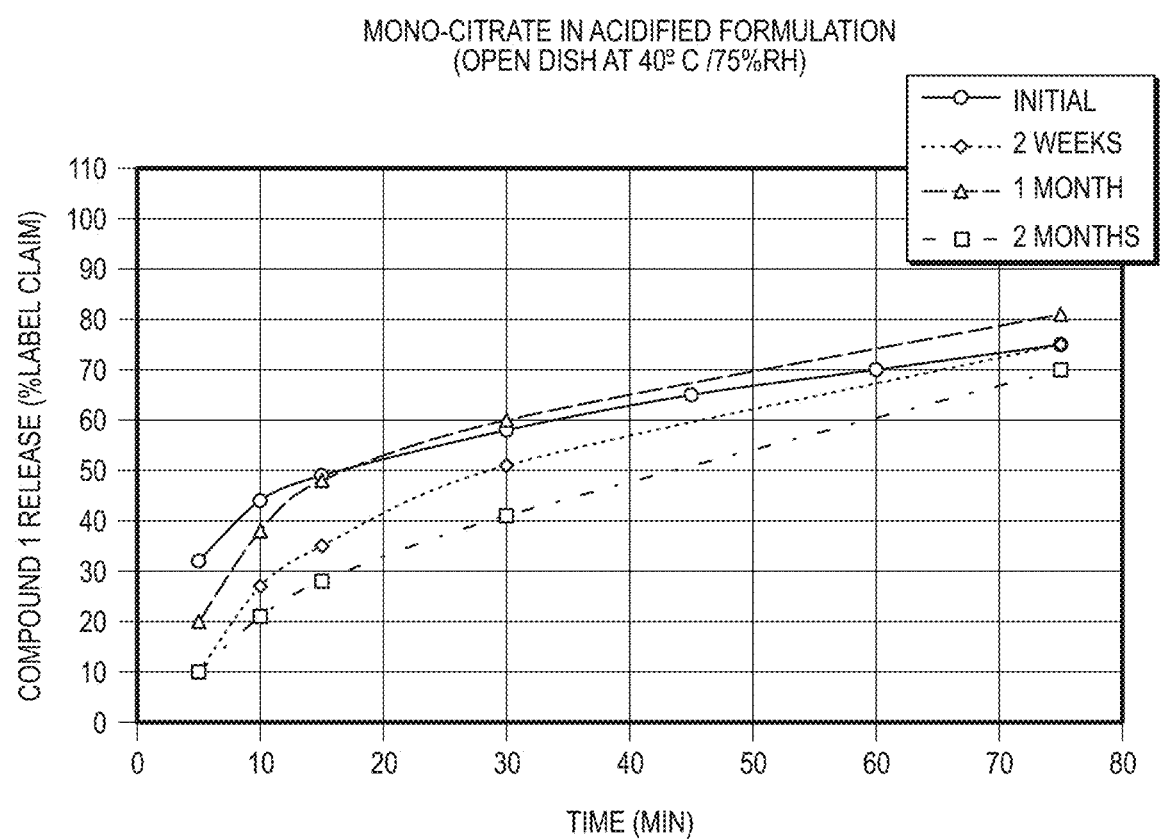
FIG. 14 is a graph showing percent release of Compound 1 over time for an acidified tablet formulation containing Compound 1 mono-citrate salt (Form A). Tablets were used initially or stored at 40° C./75% RH for 2 weeks, 1 month, or 2 months.

The Compound 1 hemi-citrate salt has also been observed to be less susceptible than the Compound 1 mono-citrate salt to dissolution slow-down of the tablet (FIG. 13 and FIG. 14). Release of Compound 1 from an acidified formulation of the Compound 1 hemi-citrate salt over time is greater than the release of Compound 1 from the same acidified formulation of the Compound 1 mono-citrate salt under all conditions (initial and tablet stored in an open dish at 40° C./75% RH for 2 weeks, 1 month, or 2 months) evaluated.

Example 7: Evaluation of Compound 1 Hemi-Citrate Salt Form I Stability

The stability of Compound 1 hemi-citrate salt Form I may be evaluated according to the ICH guidelines established for testing new drug substances and products provided below.

| Study | Storage condition | Minimum time period covered by data at submission |
|---|---|---|
| Long term* | 25° C. ± 2° C./60% RH ± 5% RH or 30° C. ± 2° C./65% RH ± 5% RH | 12 months |
| Intermediate** | 30° C. ± 2° C./65% RH ± 5% RH | 6 months |
| Accelerated | 40° C. ± 2° C./75% RH ± 5% RH | 6 months |

TABLE 4

XRPD data for Compound 1 hemi-citrate (Form I) at Various Relative Humidity Levels.

| | 90% RH | | 80% RH | | 30% RH | | 20% RH | | 10% RH | | 5% RH | |
|---|---|---|---|---|---|---|---|---|---|---|---|---|
| No. | Pos. [°2Th.] | Area [cts*°2Th.] | Pos. [°2Th.] | Area [cts*°2Th.] | Pos. [°2Th.] | Area [cts*°2Th.] | Pos. [°2Th.] | Area [cts*°2Th.] | Pos. [°2Th.] | Area [cts*°2Th.] | Pos. [°2Th.] | Area [cts*°2Th.] |
| 1 | 5.25578 | 3897.915 | 5.25364 | 4082.398 | 5.266093 | 3657.605 | 5.375748 | 2361.765 | 5.386465 | 1968.416 | 5.401141 | 1688.551 |
| 2 | 8.776926 | 109.5061 | 8.056305 | 9.5159 | 8.756164 | 143.3484 | 8.165826 | 8.4159 | 5.610637 | 83.3197 | 8.323991 | 29.903 |
| 3 | 9.394155 | 3.8454 | 8.773242 | 138.8209 | 9.431435 | 14.841 | 8.395389 | 18.8985 | 8.287765 | 35.6705 | 9.762059 | 20.0433 |
| 4 | 10.55384 | 1936.461 | 10.55617 | 2094.083 | 10.57834 | 1882.741 | 9.784048 | 10.5572 | 10.83709 | 2907.168 | 10.86104 | 2676.698 |
| 5 | 10.82057 | 694.3102 | 10.83021 | 795.0296 | 10.85946 | 747.3224 | 10.81375 | 2776.144 | 11.20042 | 454.4205 | 11.25084 | 504.3272 |
| 6 | 11.45403 | 477.89 | 11.46409 | 575.6929 | 11.47348 | 600.7789 | 11.13311 | 469.2535 | 11.78885 | 239.9092 | 11.81664 | 207.7799 |
| 7 | 13.15718 | 944.378 | 11.90238 | 17.3905 | 13.19431 | 923.8081 | 11.74763 | 321.8161 | 12.22337 | 4.6549 | 13.62526 | 1716.723 |
| 8 | 13.46031 | 274.1543 | 13.15926 | 979.2921 | 13.47106 | 633.0511 | 13.52134 | 1787.245 | 13.57646 | 1761.133 | 14.49067 | 1805.433 |
| 9 | 14.44271 | 3395.246 | 13.46074 | 477.2969 | 14.46127 | 3188.636 | 14.43512 | 1542.191 | 14.45193 | 1832.73 | 14.83302 | 1092.784 |
| 10 | 15.13749 | 29.013 | 14.43999 | 3630.561 | 15.90281 | 8440.064 | 14.71641 | 953.4994 | 14.78283 | 1128.868 | 15.44259 | 859.3604 |
| 11 | 15.86345 | 7721.828 | 15.14585 | 34.5328 | 16.23391 | 823.5547 | 15.4736 | 656.6685 | 15.43224 | 766.2203 | 16.32522 | 10236.99 |
| 12 | 16.21107 | 1245.639 | 15.86629 | 9298.573 | 16.93713 | 2228.914 | 16.25521 | 10677.09 | 16.28978 | 10765.37 | 17.14861 | 3660.487 |
| 13 | 16.89059 | 2492.92 | 16.21048 | 632.8954 | 17.21175 | 3753.326 | 17.10802 | 3414.799 | 17.11187 | 3316.73 | 17.45461 | 2867.912 |
| 14 | 17.18388 | 3387.591 | 16.89491 | 2231.896 | 17.57132 | 562.1981 | 17.34248 | 2353.879 | 17.40949 | 2795.477 | 17.73467 | 237.1892 |
| 15 | 17.56941 | 528.7267 | 17.19055 | 3483.502 | 18.4912 | 73.2217 | 18.3154 | 54.8927 | 17.68377 | 271.0192 | 18.31781 | 42.7261 |
| 16 | 18.4523 | 57.5493 | 17.57398 | 506.5786 | 18.93487 | 33.288 | 18.893 | 29.1229 | 18.30946 | 63.5757 | 18.96523 | 32.9761 |
| 17 | 18.90822 | 14.8909 | 17.69523 | 330.4736 | 19.79427 | 172.4166 | 20.32552 | 10275.56 | 18.93132 | 39.5802 | 20.31092 | 9496.987 |
| 18 | 19.74767 | 138.5363 | 18.45297 | 62.9695 | 20.48044 | 11680.28 | 20.91095 | 4896.085 | 20.29402 | 11581.9 | 20.94755 | 4759.29 |
| 19 | 20.44583 | 10963.77 | 18.91175 | 26.196 | 20.95775 | 3910.216 | 21.7133 | 613.5786 | 20.91053 | 4857.332 | 21.94565 | 701.8529 |
| 20 | 20.91627 | 3515.663 | 19.78162 | 199.158 | 22.00052 | 36.3992 | 22.37064 | 53.0638 | 21.83584 | 752.9349 | 23.53577 | 590.8894 |
| 21 | 22.13471 | 23.5194 | 20.45234 | 12682.42 | 22.97318 | 1039.773 | 23.33327 | 893.6135 | 22.49741 | 23.7501 | 23.78408 | 85.9848 |
| 22 | 22.90237 | 993.2428 | 20.92265 | 3592.329 | 23.72271 | 159.0558 | 23.67968 | 101.5554 | 23.43324 | 962.284 | 24.45675 | 195.8492 |
| 23 | 23.67076 | 152.8218 | 21.89951 | 102.4172 | 24.18204 | 67.7551 | 24.30746 | 232.0618 | 23.72526 | 116.0355 | 25.4773 | 4269.918 |
| 24 | 24.12029 | 127.8292 | 22.91401 | 1023.459 | 24.62805 | 31.0077 | 24.81256 | 248.9079 | 24.42496 | 310.0784 | 26.37809 | 509.0292 |
| 25 | 25.45671 | 4453.208 | 23.65024 | 174.983 | 25.49959 | 4851.517 | 25.47541 | 5104.938 | 24.82337 | 341.4671 | 26.81156 | 587.1546 |
| 26 | 26.15485 | 246.4866 | 24.06997 | 145.7549 | 26.21774 | 414.1629 | 26.27661 | 216.8089 | 25.45332 | 4555.557 | 26.97866 | 574.6087 |
| 27 | 26.61792 | 451.9395 | 24.63344 | 37.1932 | 26.64808 | 392.8486 | 26.8532 | 1116.245 | 26.32945 | 481.1248 | 27.40378 | 868.4664 |
| 28 | 27.40742 | 525.1628 | 25.46223 | 4603.289 | 27.44674 | 565.1327 | 27.26723 | 882.5504 | 26.85587 | 1404.08 | 27.78476 | 247.1422 |
| 29 | 28.00035 | 11.8285 | 26.14945 | 309.7147 | 27.70352 | 164.6202 | 27.67652 | 260.4958 | 27.32787 | 1038.444 | 28.1297 | 69.6186 |
| 30 | 28.53804 | 244.5173 | 26.62663 | 334.3533 | 27.99374 | 55.1947 | 28.69715 | 257.6613 | 27.70261 | 242.4791 | 28.7959 | 168.5303 |
| 31 | 29.41477 | 69.2903 | 27.41412 | 629.567 | 28.54171 | 234.9409 | 29.18789 | 17.0451 | 28.08986 | 62.7632 | 29.27839 | 16.222 |
| 32 | 29.79816 | 90.5917 | 27.66693 | 136.8292 | 29.18525 | 43.5986 | 30.13401 | 70.2304 | 28.76799 | 133.0645 | 30.30535 | 211.142 |
| 33 | 30.07974 | 380.799 | 28.00192 | 44.0067 | 29.57679 | 83.7045 | 30.49973 | 170.649 | 29.21218 | 34.9906 | 30.87199 | 302.5924 |
| 34 | 30.58038 | 90.3382 | 28.53867 | 315.8568 | 29.84152 | 34.5656 | 30.93054 | 887.7217 | 30.22927 | 234.4297 | 31.18179 | 187.8597 |
| 35 | 31.42192 | 274.1865 | 29.45239 | 101.1159 | 30.17733 | 456.2776 | 31.53406 | 198.3334 | 30.86095 | 509.4183 | 31.78271 | 297.2563 |
| 36 | 32.05774 | 220.9114 | 30.08549 | 379.0046 | 30.5437 | 115.6036 | 32.14749 | 58.9208 | 31.10324 | 236.3852 | 32.34203 | 75.2186 |
| 37 | 32.73671 | 12.7834 | 30.91577 | 13.5557 | 31.44589 | 239.0532 | 32.85396 | 349.2543 | 31.69981 | 261.9831 | 33.01845 | 467.8059 |
| 38 | 33.2967 | 154.3966 | 31.42107 | 309.643 | 32.11121 | 345.9201 | 33.76973 | 34.9405 | 32.28387 | 77.2013 | 33.90832 | 12.5301 |
| 39 | 34.12024 | 62.1183 | 32.04198 | 323.4128 | 33.35208 | 204.0598 | 34.33409 | 57.7399 | 32.92348 | 371.5478 | 34.70195 | 287.1756 |
| 40 | 34.79246 | 351.038 | 33.337 | 193.5834 | 34.10974 | 48.2761 | 34.72472 | 87.6282 | 33.98694 | 10.2039 | 35.38442 | 276.8927 |
| 41 | 35.95503 | 279.1031 | 34.0932 | 67.9349 | 34.91999 | 279.3274 | 35.46402 | 438.8012 | 34.36732 | 38.227 | 36.3065 | 294.3483 |
| 42 | 36.349 | 114.5345 | 34.78987 | 361.2348 | 35.52107 | 21.1928 | 36.25755 | 259.7429 | 34.664 | 170.1422 | 38.16241 | 80.2342 |
| 43 | 37.24761 | 45.3004 | 35.95896 | 276.0121 | 35.86875 | 331.8804 | 37.04583 | 21.5503 | 35.39156 | 467.8397 | | |
| 44 | 38.10058 | 134.9359 | 36.37035 | 153.5554 | 36.02313 | 247.7466 | 37.68336 | 78.6212 | 35.70448 | 99.5928 | | |
| 45 | 38.50546 | 114.1878 | 36.88341 | 16.1998 | 36.58399 | 137.4985 | 37.99438 | 120.2486 | 36.29356 | 267.6727 | | |
| 46 | | | 37.15437 | | 30.4599 | 37.006 | 32.4608 | 38.36948 | 14.7068 | 37.1244 | 17.4204 | |
| 47 | | | 38.08284 | 148.3765 | 37.61789 | 27.3213 | 38.97605 | 63.0784 | 37.73706 | 91.3297 | | |
| 48 | | | 38.54368 | 155.6004 | 38.03393 | 112.1298 | | | 38.0881 | 154.3818 | | |
| 49 | | | 39.61413 | 25.2194 | 38.59162 | 277.8933 | | | 39.14735 | 34.22 | | |
| 50 | | | | | 39.71819 | 25.9034 | | | | | | |

TABLE 5

Hydrogen Bonding Interaction Distances in Compound 1 Mono-citrate Salt (Form A).[1]

| Atom Pair (Citrate 1) | Donor-Acceptor distance (Å) | Atom pair (Citrate 2) | Donor-Acceptor distance (Å) |
|---|---|---|---|
| O104-O201 | 2.518 | O114-O211 | 2.541 |
| O105-O211 | 2.728 | O115-O201 | 2.755 |
| O102-O201 | 2.614 | O112-O211 | 2.633 |
| O101-O28  | 2.730 | O101-O59  | 2.735 |
| O101-N3   | 3.013 | O111-N34  | 3.179 |
| O102-N3   | 2.773 | O112-N34  | 2.665 |
| O107-O59  | 2.654 | O117-O28  | 2.689 |
| O201-O211 | 3.008 | | |

[1] Numerals between 1-99 indicate atoms in API molecules, 100-199 indicate atoms in citrate molecules, and 200+ indicate atoms in water molecules. Citrate-API interactions bolded for emphasis.

TABLE 6

Hydrogen Bonding Interaction Distances in Compound 1 Hemi-citrate Salt Form I.[1]

| Atom Pair (Citrate 1) | Donor-Acceptor distance (Å) | Atom pair (Citrate 2) | Donor-Acceptor distance (Å) |
|---|---|---|---|
| O104-O201 | 2.518 | O114-O211 | 2.541 |
| O105-O211 | 2.728 | O115-O201 | 2.755 |
| O102-O201 | 2.614 | O112-O211 | 2.633 |
| O101-O28  | 2.730 | O101-O59  | 2.735 |
| O101-N3   | 3.013 | O111-N34  | 3.179 |
| O102-N3   | 2.773 | O112-N34  | 2.665 |
| O107-O59  | 2.654 | O117-O28  | 2.689 |
| O201-O211 | 3.008 | | |

[1] Numerals between 1-99 indicate atoms in API molecules, 100-199 indicate atoms in citrate molecules, and 200+ indicate atoms in water molecules. Citrate-API interactions bolded for emphasis.

Example 8: Conversion of Compound 1 Hemi-Citrate Salt Form IA to Compound 1 Hemi-Citrate Salt Form IB Compound 1 hemi-citrate Form IA was prepared as in Example 1. Wet cakes of Compound 1 hemi-citrate Form IA prepared during filtration (prior to crystallization) were dried under full vacuum 60° C. ($N_2$/30 in Hg) for 18 hours. Compound 1 hemi-citrate Form IA converted into Compound 1 hemi-citrate Form IB upon drying.

Example 9: Gelation Experiments

During tablet dissolution experiments, it was noted that significant gelation was observed for the mono-citrate salt of Compound 1 under certain conditions. However, the hemi-citrate salt of Compound 1 was not prone to gelation under similar conditions. To confirm these findings, controlled experiments were conducted where the free base, mono-citrate, and hemi-citrate salts of Compound 1 were dissolved in aqueous media at concentrations between 0.5 mg/mL and 10 mg/mL. The dissolution experiments were performed in either 0.1 N HCl, water, or pH 7.4 buffer as aqueous media.

The hemi-citrate salt of Compound 1 did not gel in any of the aqueous media at concentrations up to 10 mg/mL. On the other hand, the mono-citrate salt of Compound 1 rapidly gelled in 0.1 N HCl media at a concentration of 5 mg/mL, but did not gel in water or pH 7.4 buffer. The free base of Compound 1 rapidly gelled in 0.1 N HCl at concentrations as low as 1 mg/mL, but did not gel in water or pH 7.4 buffer.

Example 10: Tableting Studies of Three Granulated Formulations of Compound 1 Hemi-Citrate Salt The aim of this example was to use the compaction simulator to prepare simulated roller compaction granules to investigate 3 prototype formulation blends. All compaction testing was carried out on a Phoenix hydraulic compaction simulator.

The formulation batches assessed are shown in Table 7.

TABLE 7

Formulation Batches

| | Batch #1 | Batch #2 w/w | Batch #3 |
|---|---|---|---|
| Intragranular material | | | |
| Compound 1 hemi-citrate salt | 25 | 25 | 25 |
| Lactose monohydrate (Fast Flo 316) | 50.5 | 50.5 | 50.5 |
| Crospovidone | 3 | 3 | 3 |
| Aerosil 200 | 1 | 1 | 1 |
| Magnesium stearate | 0.5 | 0.5 | 0.5 |
| Extra-granular material | | | |
| Avicel PH 102 | 15.5 | 15 | 14.5 |
| Crospovidone | 3 | 3 | 3 |
| Aerosil 2001 | 1 | 1 | 1 |
| Magnesium stearate | 0.5 | 1 | 1.5 |
| Core total | 100 | 100 | 100 |

An intragranular blend of the hemi-citrate salt of Compound 1 was slugged using a compaction simulator to create granules which were blended into the 3 final formulations. The 3 formulations all showed good strength during high speed tabletting and achieved the 1.7 MPa required for a viable formulation.

Methodology:

Production of Intragranular Blends

A 60 g intragranular blend was prepared by blending ingredients in a container using a Turbula T2 blender. The hemi-citrate salt of Compound 1 and excipients were blended for 10 minutes at 30 rpm and sieved magnesium stearate was added and blended for an additional 2 minutes. The components of the intragranular blend are shown in Table 8.

TABLE 8

Components of Intragranular Blend

| Material | % w/w | Weight (g) |
|---|---|---|
| Compound 1 (hemi-citrate salt) | 31.25 | 18.75 |
| Lactose monohydrate (Fast Flow 316) | 63.12 | 37.87 |
| Crospovidone (Polyplasdone XL-10) | 3.75 | 2.25 |
| Aerosil 200 | 1.25 | 0.75 |
| Magnesium Stearate | 0.63 | 0.38 |

The true density was determined to allow solid fraction to be calculated. The aim was to prepare granules with a nominal 0.6 Solid fraction.

Determination of True Density by Helium Pycnometry

The equipment used was a Micromeritics AccuPyc II 1340, and the test parameters are set forth below. Testing was performed in duplicate (assuming target <2% variability achieved).

| | |
|---|---|
| Cup size | 3.5 cm³ |
| Number of purges | 5 |
| Purge pressure | 19.5 psig |
| Number of runs | 10 |
| Rule fill pressure | 19.5 psig |
| Equilibration rate | 0.02 psig |
| Rune precision | Yes |
| Percentage full scale | 0.05% |

Simulating a Gerteis Roller Compaction

The aim was to compress the initial powder blend under conditions simulating a roller compactor. The results can be used to understand the compressibility potential of the material and be able to assess production requirements.

A punch profile was determined to replicate a Gerteis roller compactor. The simulation was based upon a 250 mm diameter roller operated at 4 rpm. The methodology was based on the reference A. Zinchuk et al., Int. J. Pharm. 269 (2004) 403-415, using the formula $$D = R \sin(\omega t)$$

where: D is displacement; R is the radius of the roller (mm); $\omega$=roller rotation frequency (s$^{-1}$); and t=time (s).

Key Test Parameters—Compaction

The key test parameters for compaction were as follows.

| Parameter | Value |
|---|---|
| Tooling | 10 mm flat faced B punches and die |
| Profile 1 | Gerteis simulation profile (Gerteis RC 125R 4 rpm · UPB) |
| Profile duration | 2.018 s to simulate 4 rpm |
| Lubrication of die | Internal lubrication |
| Fill weight of compacts | 300 mg |
| Target compression range | Solid fractions 0.6 target |
| Hopper used | #2 |

Equipment Used

The equipment used in this study was as follows:

| Measurement | Equipment |
|---|---|
| Compression Force | Compaction simulator load cells (50 KN) |
| Punch Displacement | Internal LVDTs |
| Compact 'hardness'/crushing strength | Hollands C50 Hardness tester (26 mm/s test speed) |
| Compact Weight | Mettler Toledo MS204S balance |
| Ejection Force | Compaction simulator lower load cell |

Choosing Settings for Slugging

A nominal minimum punch separation value was chosen as the starting point (e.g., 3 mm). The resulting solid fraction was calculated. Adjustments to the minimum distance between the punches were made to determine the settings required to achieve compacts with the target solid fraction. A fill depth of 7.3 mm, fill weight of 300 mg, and a punch separation of 4.3 mm was used. Enough compacts were made to complete the formulations. The compact parameters for every 10 compacts were checked to ensure the solid fraction was on target. The mean of recorded solid fractions was 0.597 SF.

Milling

The simulated ribbons/compacts were milled using a Krupps mini coffee grinder. The granules were screened through a 1.0 mm sieve, and any oversize fragments were remilled.

High Speed Tableting of 3 Formulation Blends
Generation of Blends for Tablet Production Small formulation blends as shown in Table 9 below were created using the sieved prepared granules.

TABLE 9

Small Formulation Blends

| Material | Blend 1 (g) | Blend 2 (g) | Blend 3 (g) |
|---|---|---|---|
| Intergranular Blend | 8.0003 | 8.0000 | 8.0000 |
| Avicel PH 102 | 1.5500 | 1.5001 | 1.4501 |
| Polyplasdone XL-10 | 0.3001 | 0.2998 | 0.2998 |
| Aerosil 200 | 0.0997 | 0.1003 | 0.0999 |
| Magnesium Stearate | 0.05 | 0.10 | 0.15 |

Formulations were blended for 10 minutes using a Turbula T2 blender, and screened magnesium stearate was added and blended in for 2 minutes.

Key Test Parameters

| Parameter | Value |
|---|---|
| Tooling | 10 mm round flat faced B |
| Profile 1—Speed 1 | Single ended sine wave with 10 mS dwell/300 mm/s average speed |
| Lubrication of die | Internal lubrication in formulation |
| Number of individual displacements | 7 |
| Number of repeats | 3 |
| Fill weight of compacts | 300 mg |
| Target compression force range | 5-25 kN |
| Target compact properties | Minimum 1.7 MPa tensile strength |
| Hopper used | #2 |

Fill Weight Determination

The material showed good flow, and therefore the hopper was used to fill the die. The starting position of the lower punch (i.e., the depth) required to produce the compact weight was determined by experimentation. This was adjusted through the test as necessary to ensure that 300 mg was achieved as closely as possible.

Profile

The profile of punch movement is programmed into the compaction simulation software and defines the movement of the punch. A single ended sine wave was used. The base of the sine wave was extended with a flat portion to achieve a target dwell time of 10 mS. The fast speed was chosen to be representative of the expected production conditions.

Choosing Compact Target Thickness

A nominal minimum punch separation value was chosen as the starting point (e.g., 3.0 mm). The resulting peak force and crushing strength were recorded. Adjustments to the minimum distance between the punches were made, and the results were recorded and plotted to estimate the settings to achieve the desired force range. More compacts were made to get compacts of different thicknesses. From this, the test conditions were selected to include a specified force range or map the material through compression into over-compression. The aim was to plot the workable range of the formulation.

Repeats of each setting were carried out to assess reproducibility for each of the points. The data was processed using the Phoenix compaction analysis software, tabulated, and exported into Excel for processing.

Physical Parameters

After ejection, the compact was examined visually and a note made of the appearance. The compact was weighed. Sometimes, when the compact is capped, the upper surface can detached and be lost; therefore the recorded weight may be lower than the actual compression weight. The thickness and diameter were measured with hand held calipers. The crushing strength (hardness) was determined in kiloponds. Crushing strength is used as a measure of how strong the bonding is within the compact. Tensile strength (MPa) is calculated from the crushing strength to allow the direct comparison of different sized compacts.

Calculations

The following calculations were used:
Average force=Mean of upper and lower peak forced (kN)
Tensile strength (MPa) for cylindrical compacts=$2P/\pi DT$, where P=Crushing strength (Hardness);
D=Compact diameter (mm); and
T=Compact thickness/height (mm)
Punch Pressure=Average Peak force/Punch tip area (MPa)
Compact volume=Pi×(compact diameter/2)$^2$×compact height (mm$^3$)
In die compact volume was measured from die diameter and minimum punch separation.
Out of die compact volume was measured from compact dimensions after ejection.
Compact density [g/cm$^3$=mg/mm$^3$]=Compact mass (mg)/Compact volume (mm$^3$)
Solid fraction=Calculated density (g/cm$^3$)/True density (g/cm$^3$)
Measurements of Manufacturability Manufacturability was measured based on the relationship between the three different compaction measurements, namely tabletability, compressibility, and compactability. Tabletability is the relationship between punch pressure and tensile strength; compressibility is the relationship between punch pressure and solid fraction, and compactability is the relationship between tensile strength and solid fraction.

Results

Tabletability

The main aim of plotting tensile strength against punch pressure is to understand how the material behaves across the whole of its compressibility range. The forces have been converted to pressures to normalize for tablet size. This makes it easier to compare tablets of different sizes. There are a number of key indicators to look for when assessing the compression properties of a material.

Namely, the shape of the plot should be sigmoidal. At very low compaction pressures, the powder is subjected to particle rearrangement, and the compacts are too weak to be held and tested. The formulation should then have a linear region where there is a good correlation between force and tablet strength. This is the region important for tableting. The points should be in line, with little variability (scatter), as this will give reproducibility and control on the tablet press.

A tensile strength of 1.7 MPa should be achieved within this linear range, as this is considered the minimum strength required for tablet production [Ref: Powder Tech 238 (2013) 169-175]. Products with a maximum tensile strength between 1.0 and 1.7 MPa can be manufactured but may require careful handling. If a formulation cannot achieve this minimum, then it is unlikely to be suitable for successful scale-up.

Figure 15:
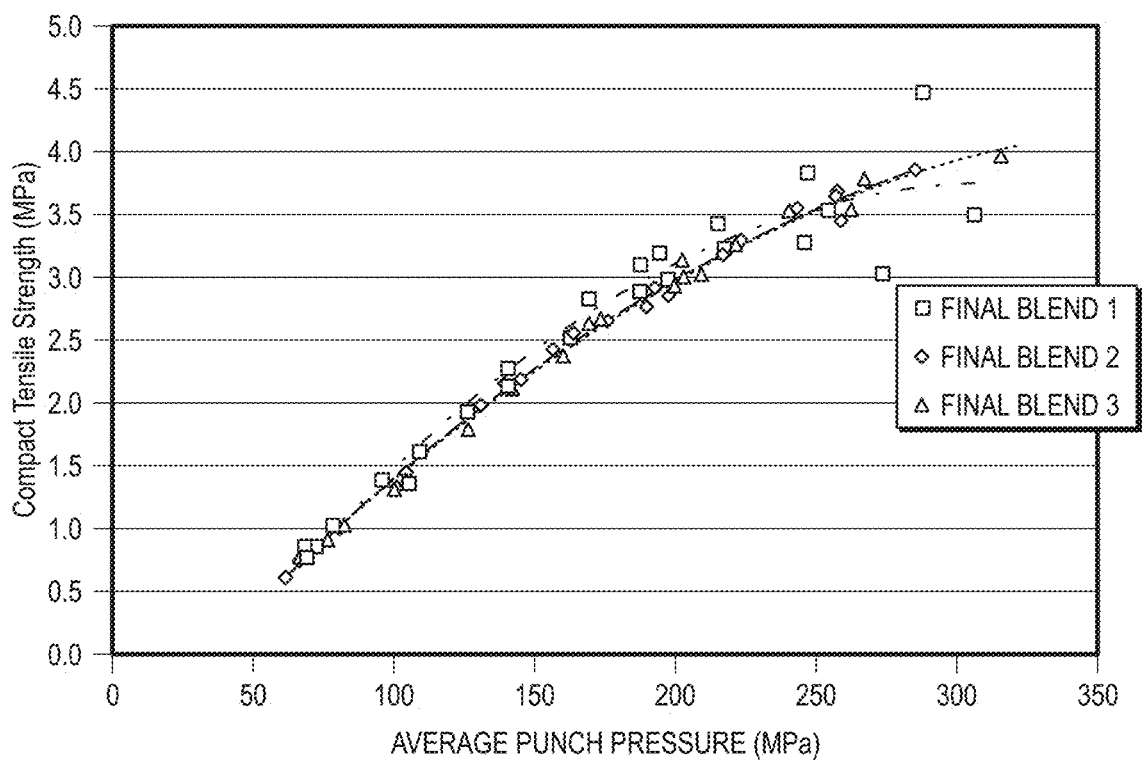
FIG. 15 is a graph showing compact tensile strength (MPa) as a function of average punch pressure (MPa) during tableting of three formulation blends of Compound 1 hemi-citrate salt Form I.

As shown in FIG. 15, all three final blends showed good tabletability, and all achieved greater than 1.7 MPa tensile strength. Formulation 3 was marginally stronger. Formulations 2 and 3 were similar.

At some point, all formulations become "over-compressed." This happens when the force of compression exceeds the compressibility of the material. This region can be seen as the plateau with scatter and variability. Sometimes the strength reaches a peak and falls away. The over-compressed tablet may exhibit visual defects such as capping and lamination. The defects may be internal and only appear as a reduction in strength of the hardness test. The onset of over-compression should be at a significantly higher force than the force used in production. If manufacture takes place at a force that is in the over-compressed region, the result is that capping and lamination will be seen, which will reduce yields. The target strength for this product can be checked against the plot to ensure that it can be manufactured successfully at high speed.

As shown in FIG. 15, the formulations become over-compressed at about 250 MPa. The onset of over-compression changes from formulation to formulation. There is evidence of scatter on Batch 1, which indicates internal variations starting to occur. This was less evident for the other two batches.

Overall, the three formulations all showed good strength during high speed tableting and achieved the 1.7 MPa required for a viable formulation.

Compactability

The density was calculated from the measured weight and compact dimensions after ejection. Solid fraction was calculated by dividing the compact density by the true density to express as a ratio of solid to space. The relationship between solid fraction and tensile strength may be useful for comparing tablet manufacturing parameters and compact size.

Figure 16:
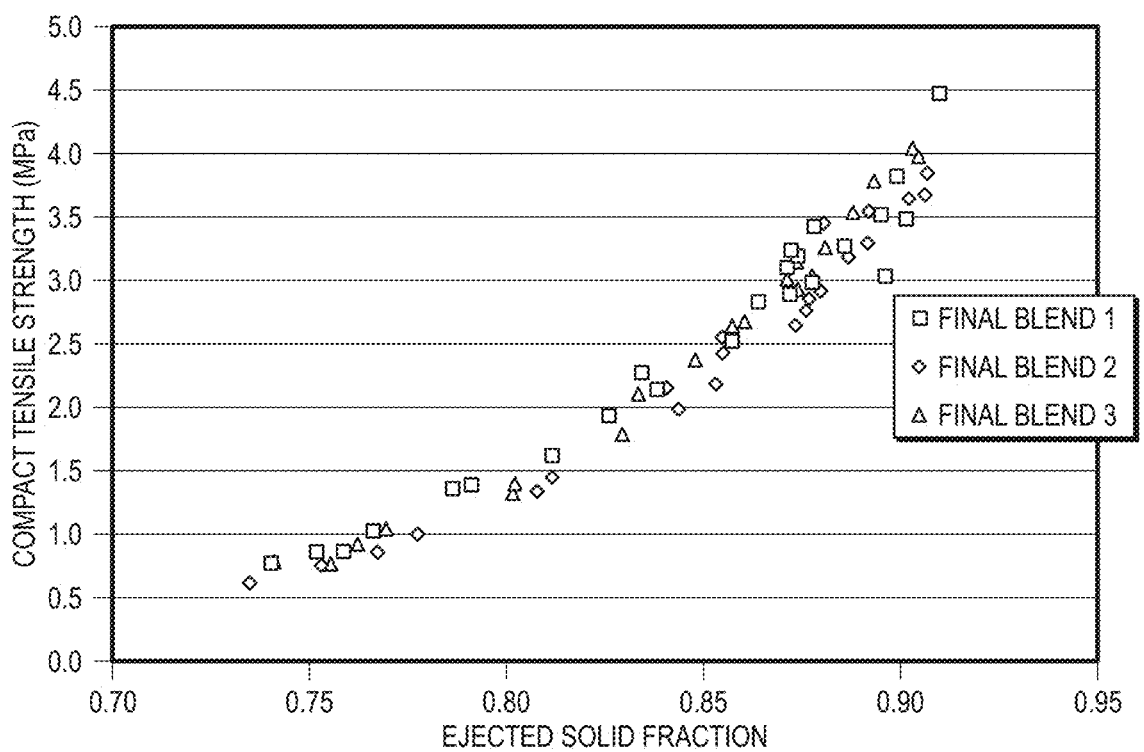
FIG. 16 is a graph showing compact tensile strength (MPa) as a function of different ejected solid fraction values during tableting of three formulation blends of Compound 1 hemi-citrate salt Form I.

The results depicted in FIG. 16 show the solid fractions required to achieve the desired compact strengths. The relationship between solid fraction and tensile strength is expected to be independent of punch speed [Ref: Amidon; J. Pharm Sci. Vol 94, 3, pp 165-472]. As the compacts are measured after ejection, capped and damaged tablets can cause outliers or scatter, such that these are difficult to measure accurately.

Standard tablet formulations are expected to be compressed to a 0.8 to 0.85 solid fraction range. This would achieve a compact strength of about 1.5 MPa across the range of batches. The target strength will be based on other quality features such as dissolution rate and friability requirements.

The solid fraction of the granules used was targeted at 0.6 SF. Extrapolating the shape of the curve would estimate that the lowest solid fraction that could be made of this final formulation would be estimated at around 0.7 SF. Different results may be achieved with different granule properties.

Compressibility

As punch pressure increases, the volume of the compact decreases. As weight is constant, the density will tend towards the true density of the material. This information can be used to understand the force required to achieve a required density and differences between the materials.

Figure 17:
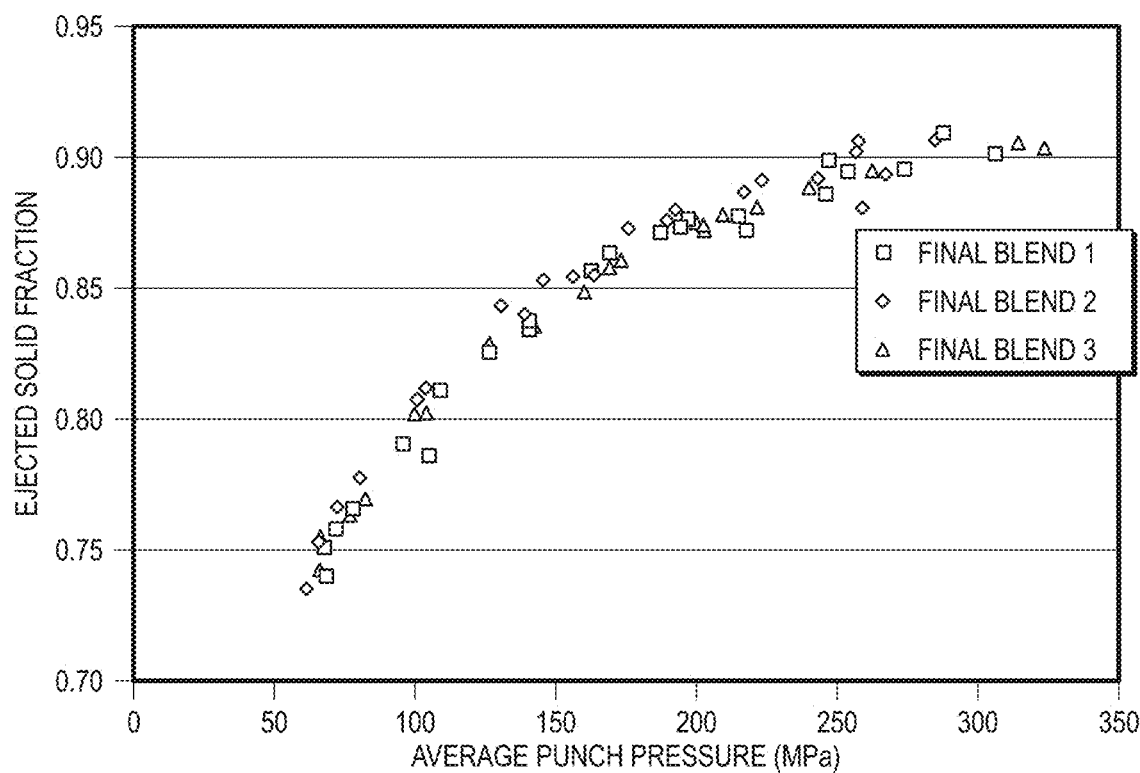
FIG. 17 is a graph showing average punch pressure (MPa) at different ejected solid fraction values during tableting of three formulation blends of Compound 1 hemi-citrate salt Form I.

As shown in FIG. 17, the formulations achieved a maximum solid fraction of just over 0.9 SF. Higher solid fractions are not possible at this speed, although they may be possible at lower compression speeds.

A punch pressure of 100 MPa will be required to make a 0.8 SF, which may be achieved using a standard tablet press and punch set-up.

Ejection Force

Ejection force is the peak force measurement on the lower punch while the tablet is ejected. The force should not normally exceed 500 N to ensure that the compact is not damaged on the way out of the die. High forces during ejection promote capping and lamination as they encourage crack propagation within the compact.

Figure 18:
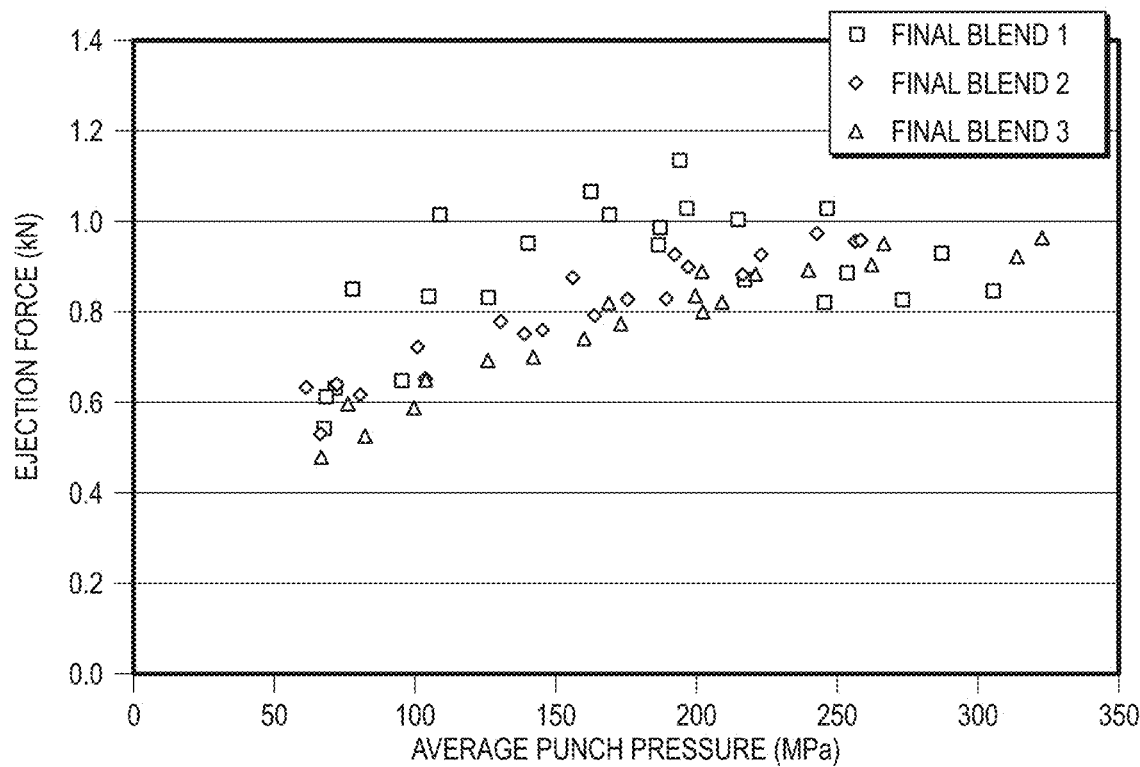
FIG. 18 is a graph showing ejection force (kN) as a function of average punch pressure (MPa) during tableting of three formulation blends of Compound 1 hemi-citrate salt Form I.

The die was not externally lubricated for this experiment, as lubricant is contained within the formulation blend. As shown in FIG. 18, ejection force for all of the formulations was higher than the recommended level. Formulation 1 was heard to audibly squeak during ejection, indicating significant friction. The ejection force was greatest for formulation 1.

Density Change after Ejection

Figure 19:
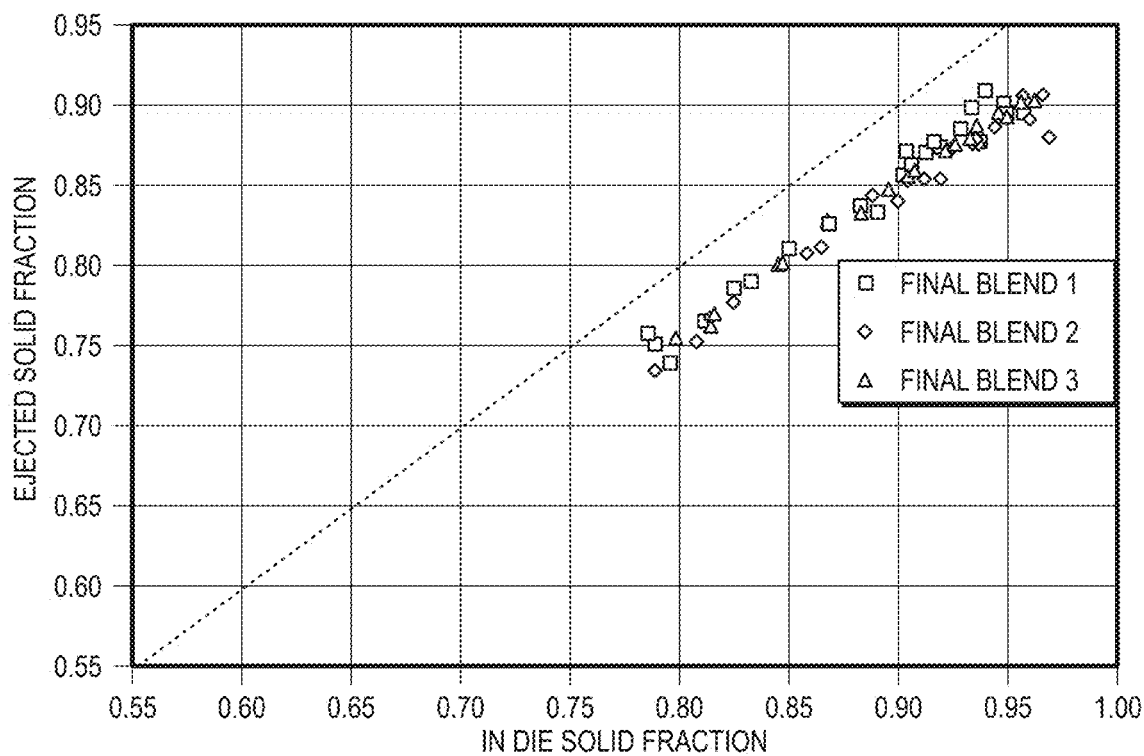
FIG. 19 is a graph showing ejection solid fraction as a function of in die solid fraction during tableting of three formulation blends of Compound 1 hemi-citrate salt Form I.

If elastic recovery is zero, the calculated density of the compact would be the same within the die and after the compact was ejected (straight line). As shown in FIG. 19, the compacts exhibit a small amount of elastic recovery.

The results show elastic recovery is relatively consistent and can therefore be predicted. To achieve a desired out of die solid fraction, a smaller target thickness is required to compensate for the elastic recovery of the compact. For example, to make a 0.80 SF compact, a target 0.85 is required. All batches showed a similar result.

Take-Off Force

When the compact is ejected, the compact sits on the lower punch and is pushed into the collection chute by an instrumented arm. The load cell can read the force taken to remove the compact from the lower punch surface. A baseline reading for a non-sticking material (e.g., Microcrystalline cellulose (Avicel)) is about 0.25 N.

Figure 20:
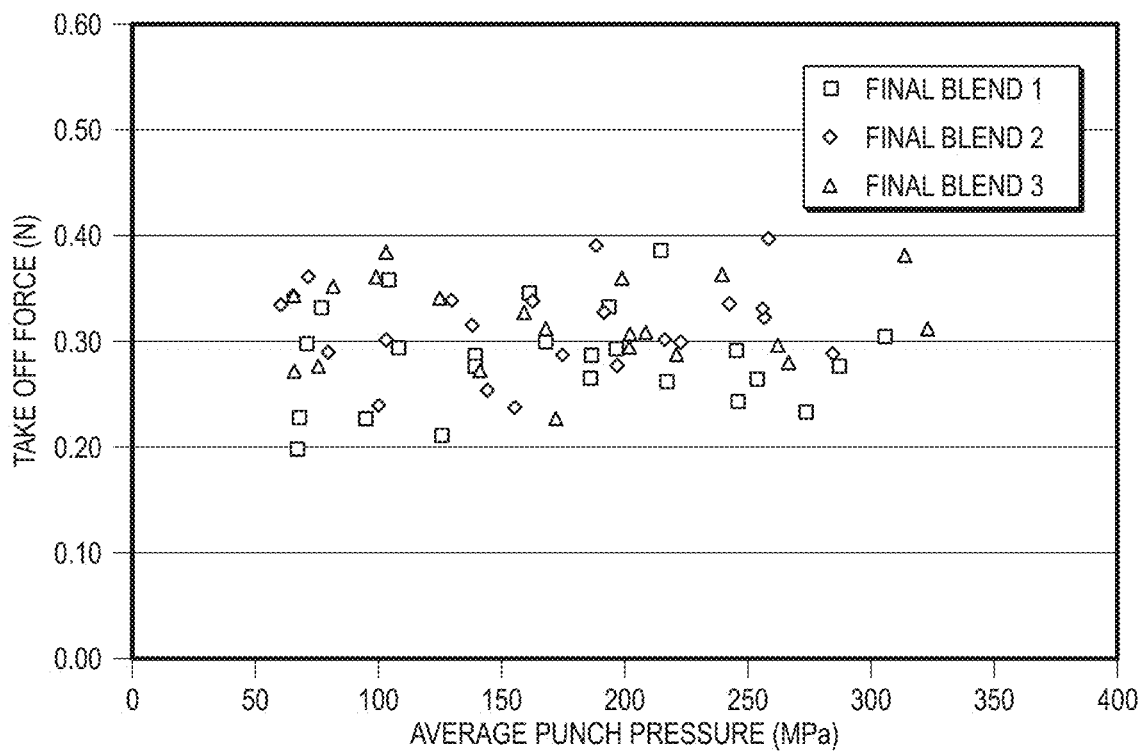
FIG. 20 is a graph showing take off force (N) as a function of average punch pressure (MPa) during tableting of three formulation blends of Compound 1 hemi-citrate salt Form I.

As shown in FIG. 20, the three different formulations have similar levels of interaction with the lower punch. Approximately half of the compacts showed similar take off forces to baseline, with the others showing a slight elevation. This suggests a slightly raised risk of sticking and picking; however, there was no visual evidence of sticking seen on any of the compacts in the test.

Example 11: Process-Scale Production of Compound 1 Hemi-Citrate Salt Tablets

Immediate release tablets comprising 10 mg or 20 mg of the hemi-citrate salt of Compound 1 were prepared. The components of the tablets are shown in Table 10.

TABLE 10

Scaled-up Tablets

| | | | Quantity per Unit | | | |
|---|---|---|---|---|---|---|
| | | | 10 mg Tablet | | 20 mg Tablet | |
| Component | Quality Standard | Function | % w/w | mg/tablet | % w/w | mg/tablet |
| Intra-granular Materials | | | | | | |
| Compound 1 hemi-citrate salt | | Active | 12.24 | 12.24 | 24.48 | 24.48 |
| Microcrystalline Cellulose (MCC) | USP-NF, Ph. Eur. | Filler | 18.00 | 18.00 | 15.00 | 15.00 |
| Lactose monohydrate[b] | USP-NF, Ph. Eur. | Filler | 58.76 | 58.76 | 49.52 | 49.52 |
| Crospovidone (CP) | USP-NF, Ph. Eur. | Disintegrant | 3.50 | 3.50 | 3.50 | 3.50 |
| Colloidal silicon dioxide (SD) | USP-NF, Ph. Eur. | Glidant | 1.00 | 1.00 | 1.00 | 1.00 |
| Magnesium stearate | USP-NF, Ph. Eur. | Lubricant | 1.00 | 1.00 | 1.00 | 1.00 |
| Extra-granular Materials | | | | | | |
| Crospovidone | USP-NF, Ph. Eur. | Disintegrant | 3.50 | 3.50 | 3.50 | 3.50 |
| Colloidal silicon dioxide | USP-NF, Ph. Eur. | Glidant | 1.00 | 1.00 | 1.00 | 1.00 |
| Magnesium stearate | USP-NF, Ph. Eur. | Lubricant | 1.00 | 1.00 | 1.00 | 2100 |
| Film Coating | | | | | | |
| Opadry ® white 03K580000 | In-house | Film coating agent | | | 3.00[c] | 3.00 |
| Purified water[d] | USP | solvent | | | — | — | q.s. = quantity sufficient.
[a] Equivalent to 20.0 mg Compound 1 free base per tablet.
[b] Quantity of lactose monohydrate adjusted accordingly for quantity of Compound 1 hemi-citrate salt.
[c] As a percentage of tablet core weight
[d] Water removed during processing and not present in final formulation.

Compound 1 hemi-citrate salt tablets were manufactured using a roller compaction granulation process. Compound 1 hemi-citrate salt was first blended with microcrystalline cellulose (MCC), lactose, hydroxypropyl methylcellulose (HPMC), and the intragranular portions of crospovidone (CP) and colloidal silicon dioxide (SD), and the blend was screened by passing through a conical mill. This powder blend was then lubricated with magnesium stearate to prepare the intragranular powder blend. The lubricated intragranular powder blend was compacted into ribbons that were granulated using a roller compactor with an in-line granulator.

The granules were then blended with the extra-granular portions of CP and SD before being lubricated with magnesium stearate to prepare the final powder blend. This final powder blend was compressed into tablet cores using a rotary tablet press and aesthetically film coated using a pan coater.

Example 12: Evaluation of Properties for Manufacture of Tablet

This example compares properties of a Compound 1 mono-citrate salt tablet with a Compound 1 hemi-citrate salt tablet.

TABLE 11

|  | Compound 1 mono-citrate salt Tablet | Compound 1 hemi-citrate salt Tablet |
|---|---|---|
| Compression Force (KN) | 12.5 | 8.5 |
| Disintegration Time (min:sec) | 5:05 | 2:12 |
| Friability (%) | 0.49 | 0.43 |

All disintegration tests were performed in accordance with the method described in USP chapter <701>, without disk. The LabIndia DT100 FD/DTT/01 model was used to perform the disintegration tests.

This example further evaluates the manufacturability of a Compound 1 hemi-citrate tablet. All the formulations listed in the table below contained 2% magnesium stearate except formulation #5. This formulation contained 4% magnesium stearate. It was observed that on average formulation #5 required the highest compression force that was needed to get to the same tablet hardness range of the other tablets at the same tableting speed. This shows the effect of increasing the concentration of magnesium stearate.

at a set speed. The force on the punch is accurately measured at frequent intervals whilst the displacement of the punches is used to calculate the volume of the powder. The yield pressure is calculated at slow and fast punch speeds to assess the time-dependent component to deformation of the material.

The true density of the material was determined by Helium Pycnometry. The true density mean for the Compound 1 mono-citrate salt Form A batch tested was 1.2666 g/cm$^3$, and the true density mean for the Compound 1 hemi-citrate salt Form I batch tested was 1.2621 g/cm$^3$.

Determination of True Density by Helium Pycnometry

The equipment used in this study was a Micromeritics AccuPyc II 1340, and the test parameters are the same as described in Example 10. The testing was performed in duplicate (assuming target <2% variability achieved).

Compression

A known weight of pure drug is compacted to theoretical zero porosity using 10 mm diameter flat faced punches. The Compaction Simulator was used under the following conditions:

| | |
|---|---|
| Tooling | 10 mm round flat faced |
| Profile | V shaped profile |
| Punch speed—Slow | 0.1 mm/s |
| Punch speed—Fast | 300 mm/s |
| Lubrication of die | Yes with Mg stearate in acetone |
| Number of repeats | 3 |
| Elasticity correction | Yes |

TABLE 12

Manufacturability of Compound 1 Hemi-Citrate Tablets

| Gravity Feeder for All Batches | Batch number | | | | | | |
|---|---|---|---|---|---|---|---|
|  | 1 | 2 | 3 | 4 | 5 | 6 | 7 |
|  |  |  |  | Uncoated tablets |  |  |  |
| Turret speed (RPM) |  | 40 | 40 | 40 | 40 | 40 | 40 |
| Compression force (kN) | 5.0-8.0 | 6.3-10.1 | 6.8-14.3 | 6-9 | 14-18 | 4-5 | 8.7-10.9 |
| Tablet hardness (N) | 63-82 | 75 (68-92) | 66 (62-74) | 64-78 | 62-79 | 63-79 | 60-70 |
| Tensile strength (MPa) |  | 2.87 | 2.53 | 2.20-2.87 | 2.15-2.92 | 2.11-2.76 |  |
| Tablet thickness (mm) | 3.30-3.39 | 3.34 (3.28-3.38) | 3.32 (3.28-3.35) | 3.22-3.38 | 3.21-3.36 | 3.34-3.45 | 3.29-3:36 |
| Disintegration time (n = 6)(Min:sec) | 01:55-03:10 | 4:40 | 3:46 | 01:30-02:50 | 03:15-03:45 | 01:30-02:15 | 00:45-01:40 |
| Average weight (mg)(n = 10) |  | 101 (98-105) | 101 (98-105) | 97-102 | 98-103 | 98-103 | 98-103 |
| % Friability | 0.36 | 0.45 | 0.27 | 0.12 | 0.18 | 0.14 | 0.07 |

Example 13: Compaction Characterization of Compound 1 Mono-Citrate Salt Form A and Compound 1 Hemi-Citrate Form I Salt By Heckel Analysis The aim of the Heckel test is to compress the material under controlled conditions to derive the yield pressure of the bulk material. A known weight of material is compressed within a 10 mm diameter die with flat faced punches moving at a set speed. During compression the location of the punch tips are accurately determined, and the force measured by load cells producing a record of the primary compression parameters. Temperature and humidity were monitored at intervals during the test.

The data were analyzed by the Compaction Analysis software program to generate values for yield pressure (Py) using the Heckel equation:

$$\ln\frac{1}{1-D} = kP + A$$

where D=the relative density of the compact;
P=Pressure applied; and
K=Gradient of the line in the linear region;
[Reference: R. W. Heckel. Trans. Metall. Soc. AIME 221 (1961)1001-1008].

Strain Rate Sensitivity (SRS)

For some materials, the deformation characteristics change with rate of applied force. This can be estimated by calculating the Strain Rate Sensitivity. The yield pressure at high speed compression is compared to that at slow speed using the following equation:

$$\% \, SRS = \frac{Py \, \text{Fast} - Py \, \text{Slow}}{Py \, \text{Slow}} \times 100$$

[Reference: R. J. Roberts and R. C. Roe, Chem. Eng. Sci. 42(1987) p 903].

Results

Compaction Results for Compound 1 Mono-Citrate Salt Form A

The compaction results for Compound 1 mono-citrate salt Form A at slow speed (0.1 mm/s) and fast speed (300 mm/s) are provided in Table 13. The lab conditions for slow speed runs and fast speed runs were 21.6° C./37.1% RH and 21.7° C./38.9% RH, respectively.

TABLE 13

Compaction Results for Compound 1 Mono-Citrate Salt Form A

| | Slow speed 0.1 mm/s | | | | Fast speed 300 mm/s | | |
| --- | --- | --- | --- | --- | --- | --- | --- |
| | Run 1 | Run 2 | Run 3 | Run 4 | Run 1 | Run 2 | Run 3 |
| Yield Pressure (MPa) | 70.114 | 92.323 | 85.677 | 90.406 | 105.169 | 111.204 | 110.483 |
| Range of linear region used in calculation (MPa) | 10-150 | 10-150 | 10-150 | 10-150 | 10-150 | 10-150 | 10-150 |
| Peak Force of Upper punch (kN) | 18.227 | 22.470 | 20.499 | 22.020 | 14.137 | 14.545 | 14.488 |
| Ejection Force (kN) | 0.603 | 0.426 | 0.518 | 0.462 | 0.740 | 0.649 | 0.719 |
| Compact observations | Ok | Ok | Ok | Ok | Laminated | Laminated | Laminated |
| Compact strength (Kiloponds) | 15.99 | 17.94 | 15.97 | 16.04 | 9.75 | 12.38 | 5.09 |

The following is a summary of the results and observations obtained with the batch of Compound 1 mono-citrate salt Form A tested.

| | |
| --- | --- |
| Yield pressure Slow (0.1 mm/s) | 84.63 MPa (±10.07) |
| Yield pressure Fast (300 mm/s) | 108.95 MPa (±3.30) |
| Strain rate sensitivity | 28.7% |

The compaction results for Compound 1 hemi-citrate salt Form I at slow speed (0.1 mm/s) and fast speed (300 mm/s) are provided in Table 14. The lab conditions for slow speed runs and fast speed runs are 21.9° C./38.9% RH and 21.9° C./38.6% RH, respectively.

TABLE 14

Compaction Results for Compound 1 Hemi-Citrate Salt Form I

| | Slow speed 0.1 mm/s | | | Fast speed 300 mm/s | | |
| --- | --- | --- | --- | --- | --- | --- |
| | Run 1 | Run 2 | Run 3 | Run 1 | Run 2 | Run 3 |
| Yield Pressure (MPa) | 67.480 | 73.595 | 67.397 | 83.127 | 80.626 | 89.401 |
| Range of linear region used in calculation (MPa) | 10-150 | 10-150 | 10-150 | 10-150 | 10-150 | 10-150 |
| Peak Force of Upper punch (kN) | 20.607 | 21.683 | 19.936 | 14.028 | 13.909 | 14.571 |
| Ejection Force (kN) | 0.416 | 0.445 | 0.479 | 0.747 | 0.736 | 0.745 |
| Compact observations | Ok | Chipped | Ok | Capped | Capped | Capped |

TABLE 14-continued

Compaction Results for Compound 1 Hemi-Citrate Salt Form I

|  | Slow speed 0.1 mm/s | | | Fast speed 300 mm/s | | |
| --- | --- | --- | --- | --- | --- | --- |
|  | Run 1 | Run 2 | Run 3 | Run 1 | Run 2 | Run 3 |
| Compact strength (Kiloponds) | 14.27 | 14.62 | 15.11 | 5.55 | 4.45 | 4.89 |

The following is a summary of the results and observations obtained with this batch of Compound 1 hemi-citrate salt Form I tested.

| Yield pressure Slow (0.1 mm/s) | 69.49 MPa (±3.55) |
| --- | --- |
| Yield pressure Fast (300 mm/s) | 84.38 MPa (±4.52) |
| Strain rate sensitivity | 21.4% |

Observations

Figure 21:
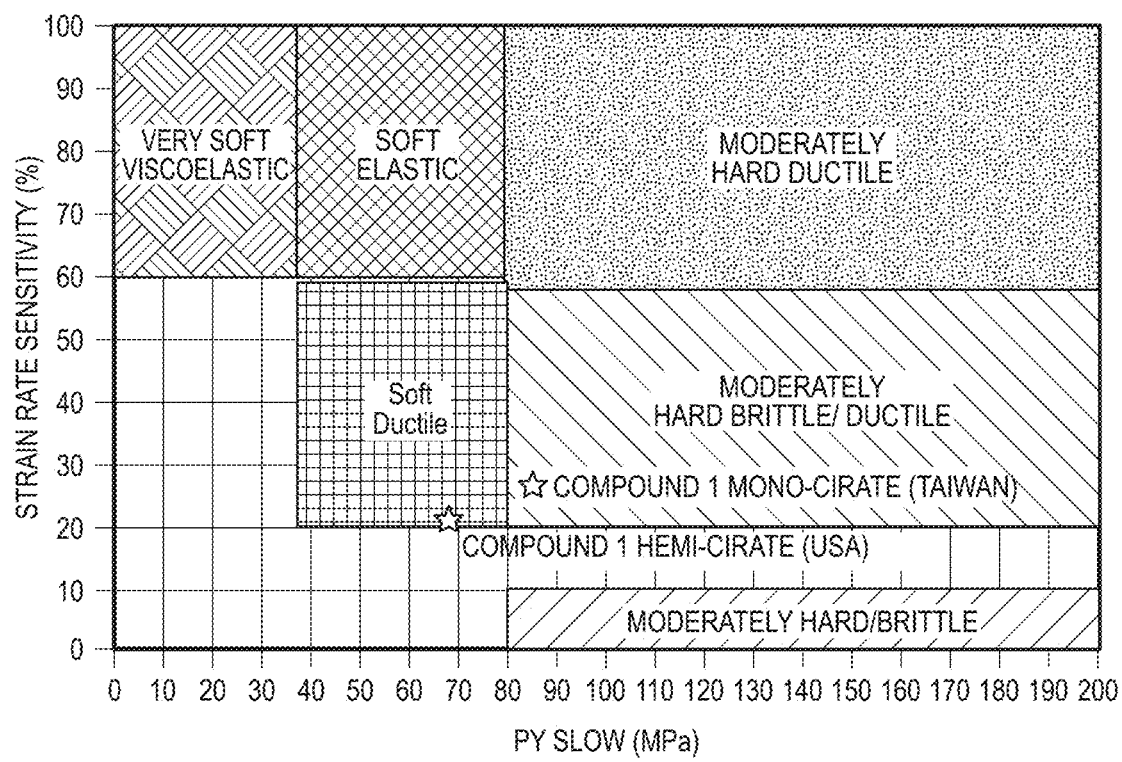
FIG. 21 shows the yield pressure of Compound 1 mono-citrate salt Form A and Compound 1 hemi-citrate salt Form I.

The yield pressure for these 2 batches of Compound 1 salts are compared in FIG. 21. As shown in FIG. 21, Compound 1 mono-citrate salt Form A had a slow speed yield pressure of 84 MPa, while Compound 1 hemi-citrate salt Form I had a yield pressure of 69 MPa. These results classify the mono-citrate salt material as having moderately brittle/ductile compaction properties and the hemi-citrate salt material as having soft ductile compaction properties.

Figure 22:
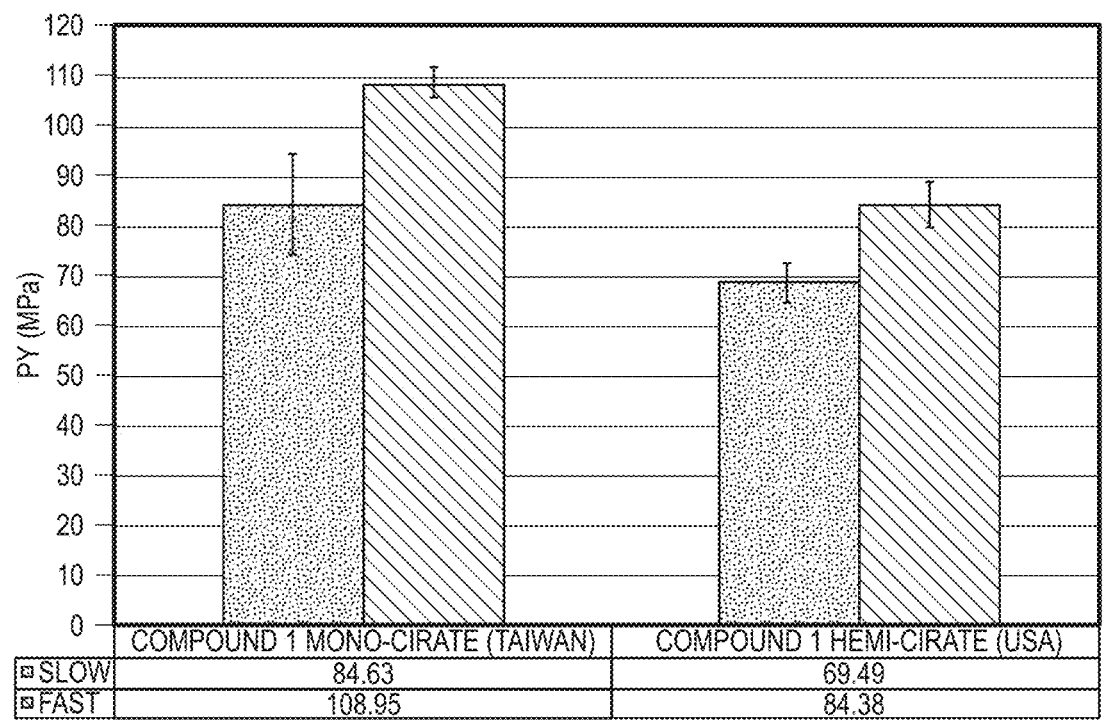
FIG. 22 shows a comparison of the yield pressure results of Compound 1 mono-citrate salt Form A and Compound 1 hemi-citrate salt Form I.

The yield pressure of both batches of Compound 1 salts increased at fast press speed, with the mono-citrate salt to 109 MPa and the hemi-citrate salt to 84 MPa. A comparison of the yield pressure results is shown in FIG. 22.

Strain rate sensitivity (SRS) measures any change in compression behavior at production compression speeds. The SRS was 28.7% for batch Compound 1 mono-citrate salt Form A and 21.4% for batch Compound 1 hemi-citrate salt Form I. This indicates that to achieve the same level of compression at fast speed, a relatively large increase in force is required, and the material is expected to show some speed related change in behavior on scale-up.

It should be noted that Heckel analysis is a measure of deformation, not the formation of a compact. To understand how the dwell time affects bonding, one looks at the compact strength. The compacts produced at slow speed were ejected whole with some chipping to the edges. Crushing strength of the Compound 1 mono-citrate salt Form A batch at slow speed was 15.6-18 kiloponds and at fast speed was 5-12.4 kiloponds. For the Compound 1 hemi-citrate salt Form I batch, the crushing strength at slow speed was 14.2-15.2 kiloponds and at fast speed was 4.4-5.6 kiloponds. Ideally, a 10 mm formulation compact should have a strength of 10-12 kiloponds to be considered low risk. The material is capable of providing bonding strength to the final formulation, so relatively high concentrations are theoretically possible. Compact strength and bonding are reduced at fast speed. As speed increases, there is less time for strong bonds to form and the compacts expand after the force is removed. Bonding strength is therefore influenced by the dwell time. In the formulation, bonding can be increased, for example, with the addition of suitable excipients, to reduce the speed effects and limit lamination.

It should also be noted that the test is designed to over-compress the material; therefore, the strength may be improved at tablet relevant compression forces.

In summary, Compound 1 shows some differences in compression and compaction between the two batches of salts. The crushing strength shows the material can provide strength to the compact, but due to the elasticity, the strength drops at fast speed.

Example 14: Punch Adhesion of Compound 1 Mono-Citrate Salt Form A and Compound 1 Hemi-Citrate Salt Form I The aim of this study was to investigate the adhesion of 2 different salt forms of Compound 1 to standard tooling steel. An instrumented adhesion punch was used to quantify the force between the upper punch surface and the newly formed tablet. The compression properties of the powder were also examined and the compact measurements taken to understand the key indicators of product quality. The test was performed at ambient room temperature. The formulation blends used in this study are shown in Table 15.

TABLE 15

Formulations of Compound 1.

| Material | Mono-Citrate 20 mg | Hemi-Citrate 20 mg |
| --- | --- | --- |
| Compound 1 mono-citrate Form A | 15.020 g |  |
| Compound 1 hemi-citrate Form 1 |  | 12.540 g |
| Lactose Monohydrate (Fast Flow 316) | 23.00 g | 24.52 g |
| Microcrystalline Cellulose (Avicel PH102) | 8.01 g | 8.99 g |
| Crospovidone (Polyplasdone XL10) | 3.00 g | 3.04 g |
| Colloidal Silicon Dioxide (Aerosil 200) | 0.52 g | 0.51g |
| Magnesium stearate | 0.5 g | 0.5 g |
| Total | 50.05 g | 50.10 g |

The instrumented adhesion punch has been designed to measure the force between the upper punch face and the upper surface of the compact. The punch tip is separate to the body of the punch. This tip is attached to a force sensor within the main body of the punch. The compact is compressed in the usual way. After compression, the punch tip remains adhered to sticky surfaces, and as the punch pulls away, a force is measured by the sensor. The greater the pull required to unstick the tablet from the surface, the greater the measurement. The measurement is recorded in volts; however, this can be converted to a force through an amplifier with an appropriate calibration. The K2 channel amplifier was used with a 50N range.

A single ended sine wave was used to mimic production punch movements. A dwell has been inserted into the base of the curve to extend the time period over which the material is in contact with the punch face to maximize the adhesion measurement. The duration of the profile was 0.5 seconds to give a dwell time of 40-45 mS.

For compression, the tooling surface was cleaned with ethanol before starting. Ten compacts were compressed, and the tooling surface evaluated. Photographs were taken of the surface to visually assess the levels of sticking.

The punch faces were cleaned with alcohol at the start, and 10 compacts were compressed per setting. After each set of 10, the punches and die were cleaned and an LVDT calibration performed. The readings start low at the beginning of the test and would be expected to reach an equilibrium amount as the surfaces are coated with the blend. Once the settings have been determined for the first run, the test can be repeated to compare different formulation parameters, temperatures, or punch coating changes. Temperature of the Compaction Simulator was measured using a thermocouple during compaction to monitor tableting conditions. Room temperature and humidity was measured at intervals during the test.

In order to ensure the test conditions were constant, control samples were also compressed. An empty die was used as a baseline check to ensure there was no friction between the punch tips and the die. The equipment was operated with no powder in place, and the forces are expected to be effectively zero. Microcrystalline cellulose (MCC, Avicel PH102) is a material with very low sticking propensity, and thus, it is used as a negative control to determine the values that are low when no sticking is present. Mannitol (Partek 200) is a material with a very high attraction to standard steel, and thus, it is used as a positive control to check that the equipment registers high sticking.

Figure 23:
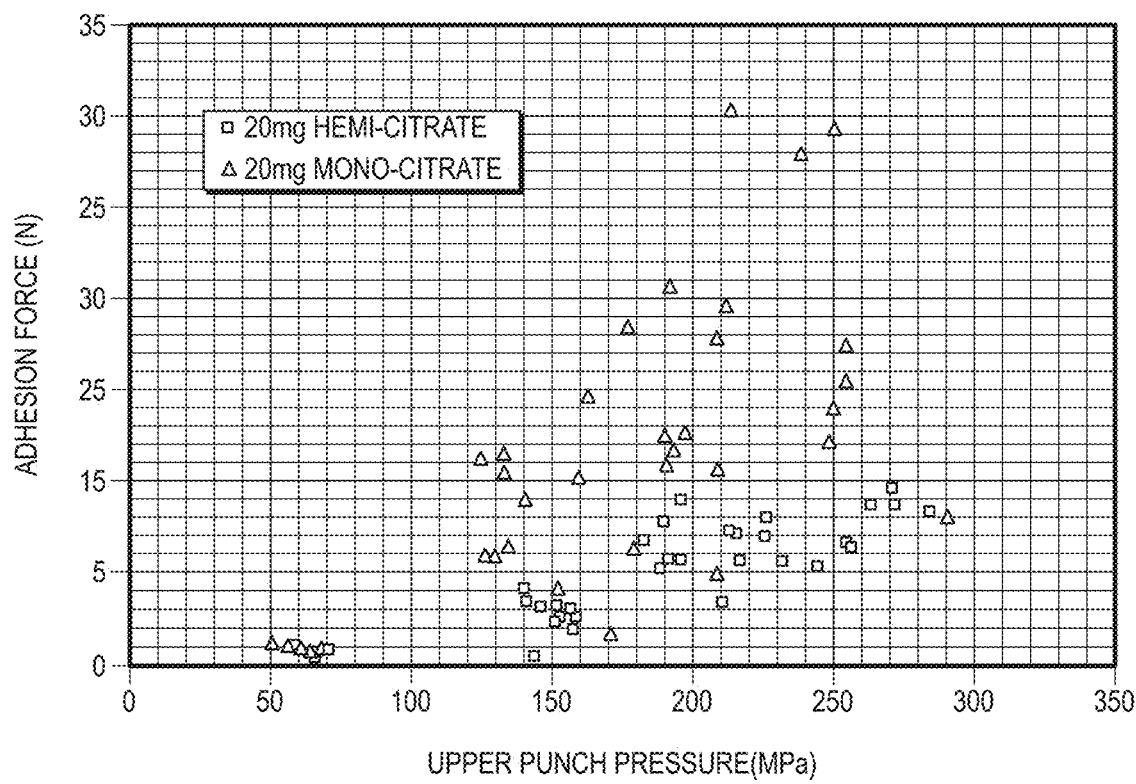
FIG. 23 shows the adhesion force as a function of compaction punch pressure of Compound 1 mono-citrate salt Form A and Compound 1 hemi-citrate salt Form I.

FIG. 23 shows the adhesion force plotted against compaction punch pressure. Adhesion force is the force registered by the instrumented adhesion punch as the punch is pulled away from the tablet surface. The punch used was the 2019 configuration. The results for the control samples performed as expected. Adhesion force for MCC was low and high for Mannitol. The empty die measurements were less than 1 N and can be considered the baseline. At the lowest compression pressure, both materials were similar. As the compaction pressures increased, the interaction with the punch increased, and adhesion force measured increased. The Compound 1 hemi-citrate salt Form I formulation had lower adhesion forces compared to the Compound 1 mono-citrate salt Form A formulation.

Figure 24:
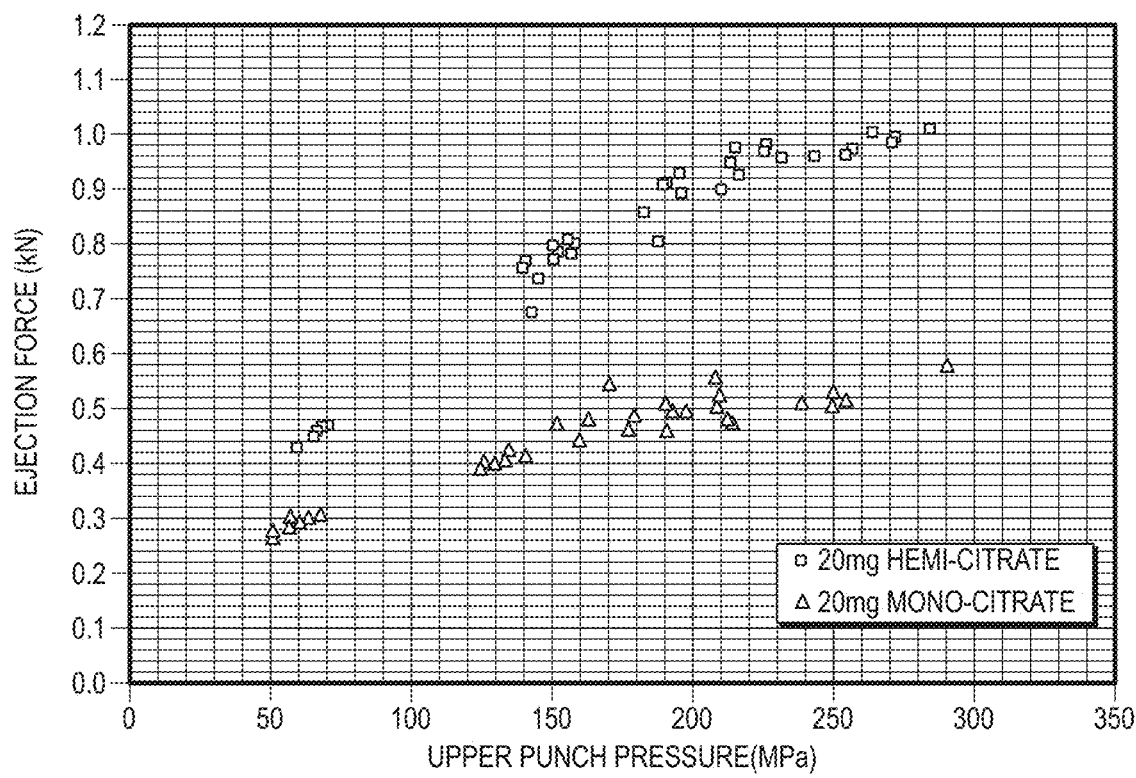
FIG. 24 shows a plot of ejection force of Compound 1 mono-citrate salt Form A and Compound 1 hemi-citrate salt Form I as described in Example 14.

FIG. 24 shows the plot of ejection force in this study. Ejection force is the force on the lower punch as the compact is being ejected. The die is made of standard steel for all compacts, and only the upper punch face is changed for the surface in question. The ejection force of the Compound 1 hemi-citrate salt Form I formulation was higher than that for the Compound 1 mono-citrate salt Form A formulation. Both increased with an increase in compaction pressure. At production relevant compaction forces, the ejection force is higher than ideally desirable.

Figure 25:
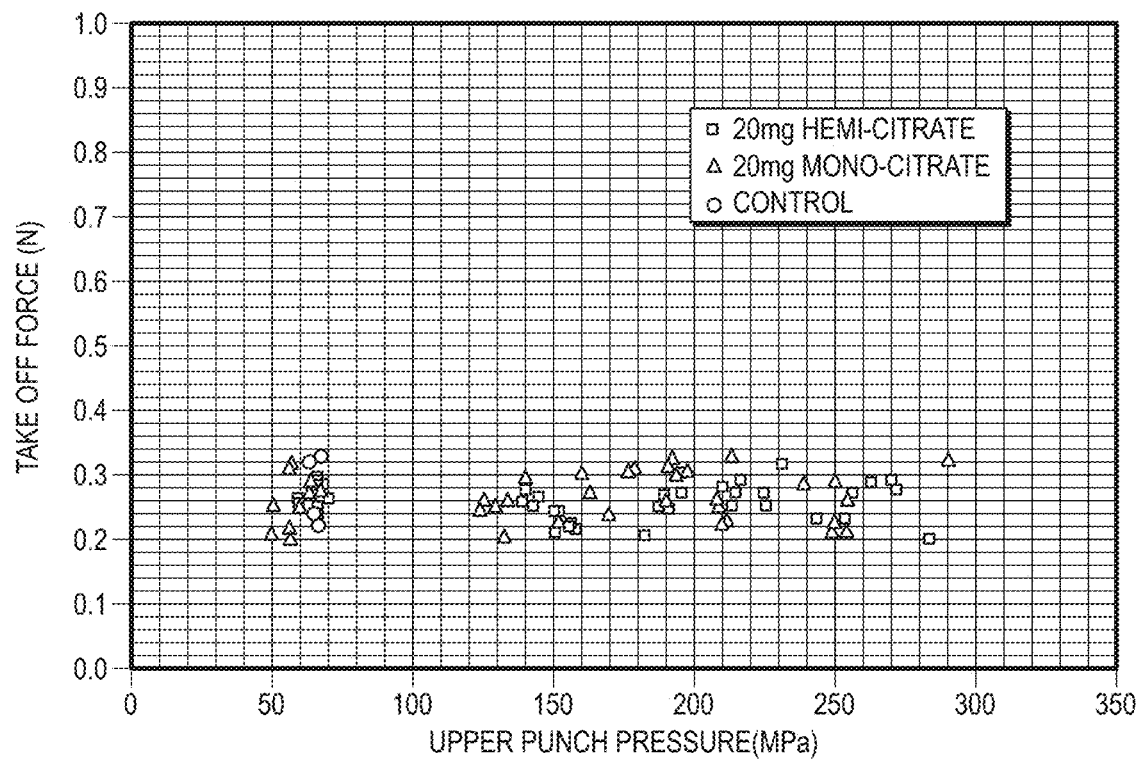
FIG. 25 shows a plot of push-off/take-off force for the Compound 1 mono-citrate salt Form A and Compound 1 hemi-citrate salt Form I formulations tested as described in Example 14.

FIG. 25 shows the plot of push-off/take-off force for the formulations tested in this study. When the tablet is ejected, it rests on the lower punch face until the arm pushes it into the collection chute. The arm is instrumented with a load cell which records the force taken to remove the sample. There is the possibility for false positives, as the load cell can pick up debris on the die table (e.g., loose granules); therefore, one looks for high frequencies of elevated results rather than individual events to indicate sticking. Baseline measurements with a material known to be non-sticking (MCC) are shown for comparison.

The lower punch is made of standard steel. The take-off force was similar to baseline measurements for both formulations. There is no evidence of significant take-off forces for either salt formulation.

Figure 27:
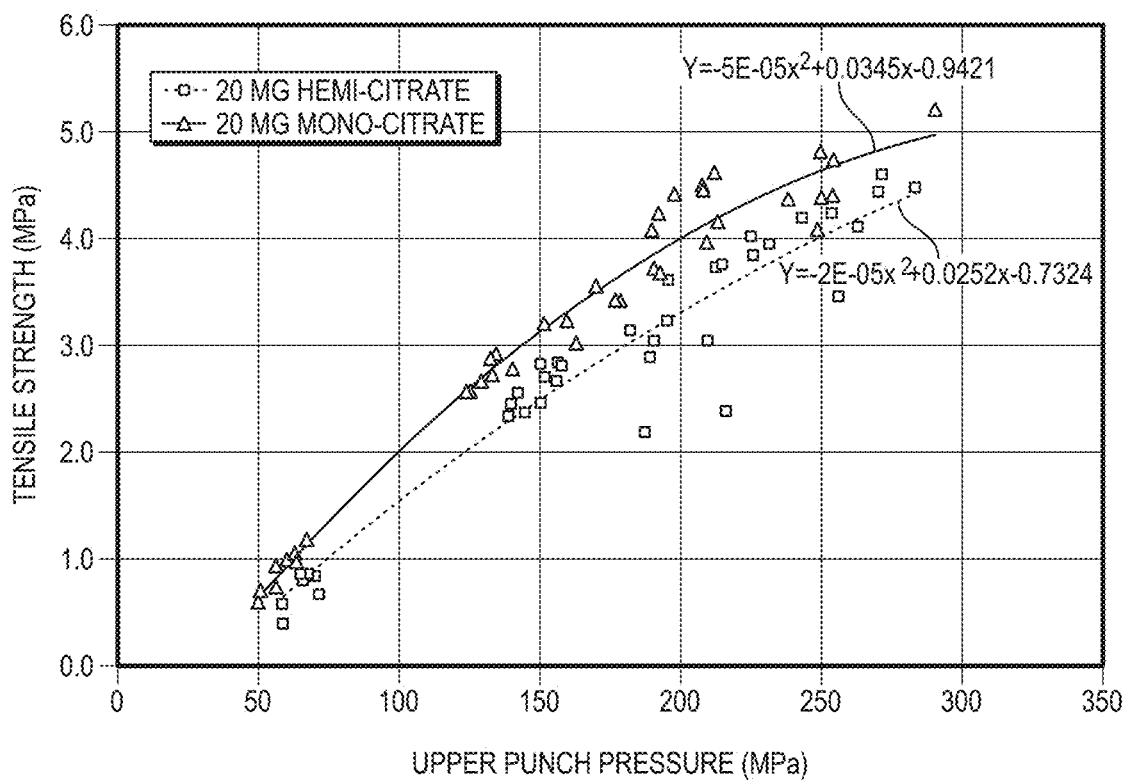
FIG. 27 is a graph showing the tabletability of a 20 mg Compound 1 mono-citrate tablet formulation and a 20 mg Compound 1 hemi-citrate tablet formulation as measured by graphing the tensile strength (MPa) as a function of upper punch pressure (MPa), as described in Example 14.

Tabletability: With respect to tabletability, the formulations were noted to have good tensile strength, exceeding 1.7 MPa, and therefore were considered low risk for tensile strength-related manufacturability issues. As shown in FIG. 27, the Compound 1 mono-citrate salt Form A formulation had a high tensile strength than the Compound 1 hemi-citrate salt Form I formulation. At faster speeds, the formulation strength was similar; however, with a longer dwell time, differences were observed in strength between the two formulations.

Picking Index: The picking index was determined for the formulation blends. Picking index is the ratio between the adhesion strength and the tensile strength. At the interface between the punch and the compact, the particles in this region can either join the compact or stick to the punch face. If the punch face is more attractive than the compact, then picking can occur. If the compact is more attractive, the tablet will have a more perfect, unblemished surface. The two factors exist side-by-side, and picking will occur if the pull towards the punch exceeds the pull from the compacts. To decrease the risk of sticking, one may either increase the tensile strength of the compact or reduce the attraction to the punch face. The tensile strength can be increased by any means known in the art, including, for example, lubricant optimization, reformulation, and/or process changes. The punch attraction can be decreased by any means known in the art, including, for example, lubricant optimization, choosing the coated tooling, and/or controlling the environment.

Figure 28:
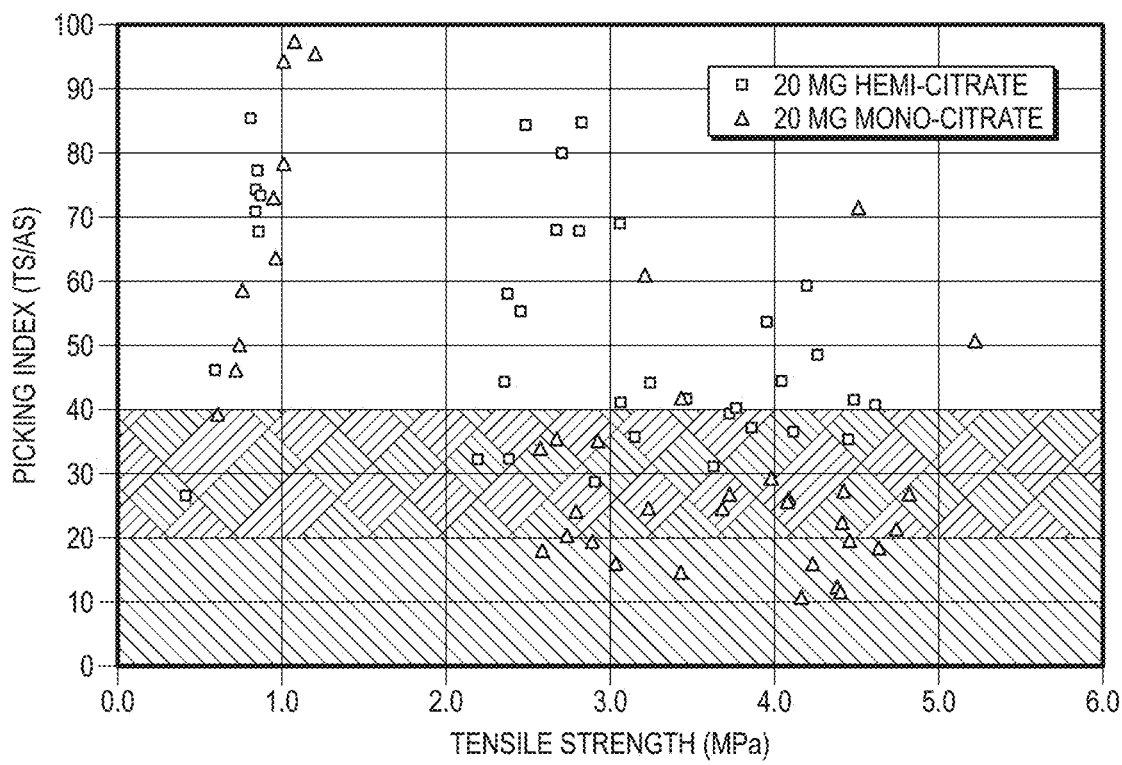
FIG. 28 is a graph showing the picking index of a 20 mg Compound 1 mono-citrate tablet formulation and a 20 mg Compound 1 hemi-citrate tablet formulation as measured by graphing the picking index (TS/AS) as a function of tensile strength (MPa), as described in Example 14.

As shown in FIG. 28, the picking index was plotted as a function of tensile strength. In general, the lower the picking index, the higher the risk of sticking. A picking index less than 20 indicates a high risk of sticking, while a picking index less than 40 indicates a moderate risk of sticking, and a picking index greater than 50 indicates a low risk of sticking. As shown in FIG. 28, there were ten compacts of the 20 mg formulation of the Compound 1 mono-citrate Form A blend in the high risk region (i.e., 0-20), while there were no compacts of the 20 mg formulation of the Compound 1 hemi-citrate Form I blend in the high risk region. This indicates that the Compound 1 hemi-citrate Form I formulation had a lower risk of sticking than the Compound 1 mono-citrate Form A formulation.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as acknowledgment or any form of suggestion that they constitute valid prior art or form part of the common general knowledge in any country in the world.

What is claimed is:

1. A substantially pure hemi-citrate salt of Compound 1 having the formula:

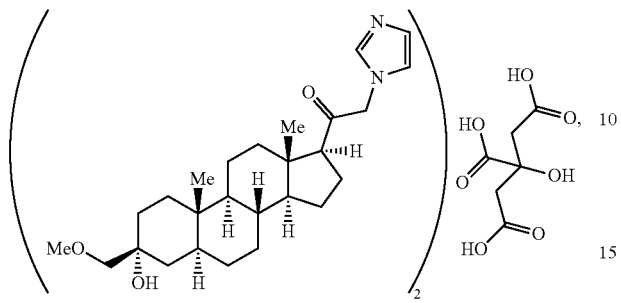

wherein the hemi-citrate salt is at least about 95% pure and contains less than about 5% by weight of a mono-citrate salt of Compound 1.

2. The substantially pure hemi-citrate salt of claim 1, wherein the hemi-citrate salt is a hydrate.

3. The substantially pure hemi-citrate salt of claim 1, wherein the hemi-citrate salt has a water content from about 0% to about 5% by weight.

4. The substantially pure hemi-citrate salt of claim 1, wherein the hemi-citrate salt is a sesquihydrate.

5. The substantially pure hemi-citrate salt of claim 1, wherein the hemi-citrate salt is a crystalline channel hydrate.

6. The substantially pure hemi-citrate salt of claim 5, wherein the crystalline channel hydrate has a water content of about 4.4% by weight and exhibits a differential scanning calorimetry (DSC) thermogram having a first peak value at about 65.2±2.0° C. and a second peak value at about 126.3±2.0° C. or wherein the crystalline channel hydrate exhibits a thermogravimetric analysis (TGA) thermogram with a weight loss of about 0.0% to 4.4% in the temperature range of 25 and 125° C.

7. The substantially pure hemi-citrate salt of claim 1, wherein the hemi-citrate salt is crystalline Form IA of the Compound 1 and exhibits an X-ray powder diffraction (XRPD) pattern comprising peaks at the diffraction angle 2-theta 5.3±0.2, 10.6±0.2, and 15.9±0.2.

8. The substantially pure hemi-citrate salt of claim 7, wherein the crystalline Form IA exhibits an X-ray powder diffraction (XRPD) pattern further comprising at least one of the following peaks at the diffraction angle 2-theta: 14.5±0.2, 17.2±0.2, 17.6±0.2, 21.0±0.2, and 25.5±0.2.

9. The substantially pure hemi-citrate salt of claim 7, wherein the crystalline Form IA exhibits an X-ray powder diffraction (XRPD) pattern further comprising at least three of the following peaks at the diffraction angle 2-theta: 14.5±0.2, 17.2±0.2, 17.6±0.2, 20.5±0.2, 21.0±0.2, and 25.5±0.2.

10. The substantially pure hemi-citrate salt of claim 7, wherein the crystalline Form IA exhibits an X-ray powder diffraction (XRPD) pattern further comprising the following peaks at the diffraction angle 2-theta: 14.5±0.2, 17.2±0.2, 17.6±0.2, 20.5±0.2, 21.0±0.2, and 25.5±0.2.

11. The substantially pure hemi-citrate salt of claim 1, wherein the hemi-citrate salt is crystalline Form IA and exhibits an X-ray powder diffraction (XRPD) pattern that is substantially as shown in FIG. 1.

12. The substantially pure hemi-citrate salt of claim 1, wherein the hemi-citrate salt is crystalline Form IB of Compound 1 and exhibits an X-ray powder diffraction (XRPD) pattern comprising peaks at the diffraction angle 2-theta 5.4±0.2, 10.9±0.2, 14.8±0.2, and 16.3±0.2.

13. The substantially pure hemi-citrate salt of claim 12, wherein the crystalline Form IB exhibits an XRPD pattern further comprising at least one of the following peaks at the diffraction angle 2-theta: 14.5±0.2, 17.1±0.2, 17.5±0.2, 21.0±0.2, and 25.5±0.2.

14. The substantially pure hemi-citrate salt of claim 12, wherein the crystalline Form IB exhibits an X-ray powder diffraction (XRPD) pattern further comprising at least three of the following peaks at the diffraction angle 2-theta: 17.1±0.2, 17.5±0.2, 20.3±0.2, 21.0±0.2, and 25.5±0.2.

15. The substantially pure hemi-citrate salt of claim 12, wherein the crystalline Form IB exhibits an X-ray powder diffraction (XRPD) pattern further comprising the following peaks at the diffraction angle 2-theta: 10.9±0.2, 14.5±0.2, 17.1±0.2, 21.0±0.2, and 25.5±0.2.

16. The substantially pure hemi-citrate salt of claim 1, wherein the hemi-citrate salt is crystalline Form IB and exhibits an X-ray powder diffraction (XRPD) pattern that is substantially as shown in FIG. 2.

17. A pharmaceutical composition comprising the substantially pure hemi-citrate salt of claim 1 and at least one pharmaceutically acceptable excipient.

18. The pharmaceutical composition of claim 17, wherein after the composition is stored at about 40° C. and 75% relative humidity for about 6 months the chemical purity of the Compound 1 in the composition is at least about 98%.

19. The pharmaceutical composition of claim 17, wherein the composition comprises no more than about 0.5% by weight of a C-17 epimer of Compound 1 after the composition is stored at about 40° C. and 75% relative humidity for about 6 months, based on the total weight of Compound 1 in the composition.

20. The pharmaceutical composition of claim 17, further comprising a lubricant, wherein the percentage of the lubricant in the pharmaceutical composition is less than about 4% by weight.

21. The pharmaceutical composition of claim 20, wherein the percentage of lubricant in the pharmaceutical composition is from about 1% to about 2% by weight.

22. The pharmaceutical composition of claim 20, wherein the lubricant is magnesium stearate.

23. The pharmaceutical composition of claim 17, comprising:
about 25% hemi-citrate salt of Compound 1 by weight;
about 2% magnesium stearate by weight; and
about 7% crospovidone by weight.

24. The pharmaceutical composition of claim 23, wherein the composition contains less than 5% of a mono-citrate salt of Compound 1 by weight.

25. A method of preparing a hemi-citrate salt of Compound 1 having the formula:

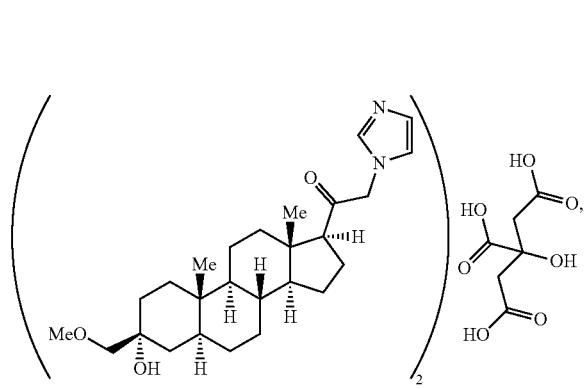

the method comprising:
(a) dissolving a mono-citrate salt of Compound 1 in $C_1$-$C_2$ alcohol to produce a solution; and
(b) adding the solution to water to provide the hemi-citrate salt of Compound 1.

26. A method of preparing a hemi-citrate salt of Compound 1 having the formula:

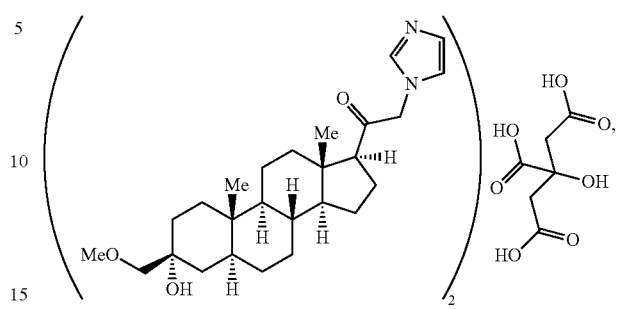

the method comprising:
(a) suspending a mono-citrate salt of Compound 1 in water; and
(b) isolating the hemi-citrate salt of Compound 1.

27. A method of treating a disease or condition comprising administering to a patient in need thereof a therapeutically effective amount of the pharmaceutical composition of claim 21, wherein the disease or condition is selected from depression, epilepsy, bipolar disorder, or anxiety.

28. The method of claim 27, wherein the depression is selected from major depressive disorder, post-partum depression, or treatment resistant depression.

* * * * *